(12) United States Patent
Swager et al.

(10) Patent No.: US 7,393,503 B2
(45) Date of Patent: Jul. 1, 2008

(54) EMISSIVE POLYMERS AND DEVICES INCORPORATING THESE POLYMERS

(75) Inventors: Timothy M. Swager, Newton, MA (US); Jye-Shane Yang, Ping-Chen (TW); Vance Williams, Vancouver (CA); Yijun Miao, Falls Church, VA (US); Claus G. Lugmair, San Jose, CA (US); Igor A. Levitsky, Fall River, MA (US); Jinsang Kim, Ann Arbor, MI (US); Robert Deans, Grafton, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 362 days.

(21) Appl. No.: 11/252,530

(22) Filed: Oct. 17, 2005

(65) Prior Publication Data
US 2006/0120923 A1 Jun. 8, 2006

Related U.S. Application Data

(60) Division of application No. 10/324,064, filed on Dec. 18, 2002, now Pat. No. 7,208,122, which is a continuation of application No. 09/305,379, filed on May 5, 1999, now abandoned.

(60) Provisional application No. 60/084,247, filed on May 5, 1998.

(51) Int. Cl.
*C08G 61/02* (2006.01)

(52) U.S. Cl. .......................... 422/82; 435/6; 435/287.2; 525/54.2

(58) Field of Classification Search .................. 422/82; 524/492; 525/54.2; 435/6, 287.2
See application file for complete search history.

(56) References Cited

U.S. PATENT DOCUMENTS 4,356,429 A 10/1982 Tang (Continued)

FOREIGN PATENT DOCUMENTS

DE 197 44 792 A1 4/1999

(Continued)

OTHER PUBLICATIONS

Zhou et al. Fluorescent Chemosensors Based on Energy Migration in Conjugated Polymers: The Molecular Wire Approach to Increased Sensitivity, 1995, J. Am. Chem. Soc., 117, pp. 12593-12602.*

(Continued)

*Primary Examiner*—Walter D. Griffin
*Assistant Examiner*—Christine T Mui
(74) *Attorney, Agent, or Firm*—Wolf, Greenfield & Sacks, P.C.

(57) ABSTRACT

The present invention relates to a class of luminescent and conductive polymer compositions having chromophores, and particularly solid films of these compositions exhibiting increased luminescent lifetimes, quantum yields and amplified emissions. These desirable properties can be provided through polymers having rigid groups designed to prevent polymer reorganization, aggregation or π-stacking upon solidification. These polymers can also display an unusually high stability with respect to solvent and heat exposures. The invention also relates to a sensor and a method for sensing an analyte through the luminescent and conductive properties of these polymers. Analytes can be sensed by activation of a chromophore at a polymer surface. Analytes include aromatics, phosphate ester groups and in particular explosives and chemical warfare agents in a gaseous state. The present invention also relates to devices and methods for amplifying emissions by incorporating a polymer having an energy migration pathway and/or providing the polymer as a block co-polymer or as a multi-layer.

9 Claims, 39 Drawing Sheets

U.S. PATENT DOCUMENTS

| | | | |
|---|---|---|---|
| 4,687,732 A | 8/1987 | Ward et al. |
| 4,927,768 A | 5/1990 | Coughlin et al. |
| 4,946,890 A | 8/1990 | Meador |
| 4,992,302 A | 2/1991 | Lindmayer |
| 5,155,149 A | 10/1992 | Atwater et al. |
| 5,194,393 A | 3/1993 | Hugl et al. |
| 5,236,808 A | 8/1993 | Smothers |
| 5,244,813 A | 9/1993 | Walt et al. |
| 5,254,633 A | 10/1993 | Han et al. |
| 5,364,797 A | 11/1994 | Olson et al. |
| 5,414,069 A | 5/1995 | Cumming et al. |
| 5,451,683 A | 9/1995 | Barrett et al. |
| 5,511,547 A | 4/1996 | Markle et al. |
| 5,512,490 A | 4/1996 | Walt et al. |
| 5,532,129 A | 7/1996 | Heller |
| 5,540,999 A | 7/1996 | Yamamoto et al. |
| 5,546,889 A | 8/1996 | Wakita et al. |
| 5,554,747 A | 9/1996 | Sharma et al. |
| 5,556,524 A | 9/1996 | Albers |
| 5,563,056 A | 10/1996 | Swan et al. |
| 5,565,322 A | 10/1996 | Heller |
| 5,580,527 A | 12/1996 | Bell et al. |
| 5,585,646 A | 12/1996 | Kossovsky et al. |
| 5,591,787 A | 1/1997 | Schlennert et al. |
| 5,597,890 A | 1/1997 | Jenekhe |
| 5,607,864 A | 3/1997 | Ricchiero et al. |
| 5,629,353 A | 5/1997 | Steckle, Jr. et al. |
| 5,679,773 A | 10/1997 | Holmes |
| 5,700,696 A | 12/1997 | Chandross et al. |
| 5,705,348 A | 1/1998 | Meade et al. |
| 5,709,994 A | 1/1998 | Pease et al. |
| 5,710,187 A | 1/1998 | Steckle, Jr. et al. |
| 5,710,197 A | 1/1998 | Fischer et al. |
| 5,723,218 A | 3/1998 | Haugland et al. |
| 5,869,592 A | 2/1999 | Gagné et al. |
| 5,925,517 A | 7/1999 | Tyagi et al. |
| 6,020,426 A | 2/2000 | Yamaguchi et al. |
| 6,259,277 B1 | 7/2001 | Tour et al. |
| 6,509,110 B1 | 1/2003 | Salbeck et al. |
| 6,556,335 B2 | 4/2003 | Jones et al. |
| 6,589,731 B1 | 7/2003 | Chen et al. |
| 6,605,693 B1 | 8/2003 | Becker et al. |
| 6,713,298 B2 | 3/2004 | McDevitt et al. |
| 6,743,640 B2 | 6/2004 | Whitten et al. |
| 6,783,814 B2 | 8/2004 | Swager et al. |
| 6,962,757 B2 | 11/2005 | Epstein et al. |
| 7,186,355 B2 | 3/2007 | Swager et al. |
| 7,208,122 B2 | 4/2007 | Swager et al. |
| 2002/0040805 A1 | 4/2002 | Swager et al. |
| 2002/0150697 A1 | 10/2002 | Swager et al. |
| 2002/0177136 A1 | 11/2002 | McBranch et al. |
| 2003/0054413 A1 | 3/2003 | Kumaraswamy et al. |
| 2003/0134959 A1 | 7/2003 | Hancock et al. |
| 2004/0043251 A1 | 3/2004 | Epstein et al. |
| 2004/0121337 A1 | 6/2004 | Deans et al. |
| 2004/0175768 A1 | 9/2004 | Kushon et al. |
| 2004/0235184 A1 | 11/2004 | Swager |
| 2004/0241768 A1 | 12/2004 | Whitten et al. |
| 2005/0014160 A1 | 1/2005 | Kumaraswamy et al. |
| 2006/0024707 A1 | 2/2006 | Deans et al. |

FOREIGN PATENT DOCUMENTS

| | | |
|---|---|---|
| DE | 198 06 037 A1 | 9/1999 |
| EP | 0 442 123 | 8/1991 |
| EP | 0 442 123 A1 | 8/1991 |
| EP | 0581058 A1 | 2/1994 |
| EP | 1 011 154 A1 | 6/2000 |
| JP | 06-322078 | 11/1994 |
| WO | WO 89/00593 | 1/1989 |
| WO | WO 95/16681 | 6/1995 |
| WO | WO 99/19419 A1 | 4/1999 |
| WO | WO 99/57222 | 11/1999 |
| WO | WO 00/53655 A1 | 9/2000 |
| WO | WO 01/57140 A1 | 8/2001 |
| WO | WO 02/16463 A2 | 2/2002 |
| WO | WO 03/048226 A2 | 6/2003 |
| WO | WO 2004/005701 A2 | 7/2004 |
| WO | 2006/081345 A1 | 8/2006 |

OTHER PUBLICATIONS

Hoffmeister et al., "Triptycene Polymers," J. Polymer Science 1969, 7, 55-72.

Brabec, Christoph, et al. "Plastic Solar Cells", *Adv. Funct. Mater*, 2001, vol. 11, No. 1, pp. 15-26.

Chemical Structure for Biphenylene. CAS No. 259-79-0.

Chen, Liaohai et al., "Tuning the properties of conjugated polyelectrolytes through surfactant complexation," *J. Am. Chem. Soc.*, 2000, vol. 122 No. 38, pp. 9302-9303.

Chen, Liaohai, et al., "Highly Sensitive Biological and Chemical Sensors Based on Reversible Fluorescence Quenching in a Conjugated Polymer," Proceedings of the National Academy of Sciences of the United States of America, Oct. 26, 1999, vol. 96, No. 22, pp. 12287-12292.

Cotts, Patricia M., et al., "Equilibrium Flexibility of a Rigid Linear Conjugated Polymer," *Macromolecules*, 1996, vol. 29, pp. 7323-7328.

Dagani, Ron, "A Better Sensor for Nerve Gas," C&EN, Mar. 10, 2003, p. 12.

Deans, Robert, et al., "A Poly(*p*-phenyleneethynylene) with a Highly Emissive Aggregated Phase", *J. Am. Chem. Soc.*, 2000, vol. 122, pp. 8565-8566.

Fiesel, Rainer, et al., "A chiral poly(*para*-phenyleneethynylene) (PPE) derivative," *Macromol. Rapid Commun.*, 1998, vol. 19, No. 8, pp. 427-431.

Fiesel, Rainer, et al., "Aggregation-induced CD effects in chiral poly(2,5-dialkoxy-1,4-phenylene)s," *Acta Polym.*, 1998, vol. 49, pp. 445-449.

Fiesel, Rainer, et al., "On the Solid State Aggregation of Chiral Substituted Poly(*para*-phenylene)s (PPPs)," *Synthetic Metals*, 1999, vol. 102, pp. 1457-1458.

Fu, Dian-Kui, et al., "Alternating Poly(PyridylVinylenePhenyleneVinylene)s: Synthesis and Solid State Organizations," *Tetrahedron*, 1997, vol. 53, No. 45, pp. 15487-15494.

Gaylord, Brent S., et al., "DNA detection using water-soluble conjugated polymers and peptide nucleic acid probes," *PNAS*, Aug. 20, 2002, vol. 99, No. 17, pp. 10954-10957.

Gaylord, Brent S., et al., "Water-Soluble Conjugated Oligomers: Effect of Chain Length and Aggregation on Photoluminescence-Quenching Efficiencies," Journal of the American Chemical Society, Jun. 8, 2001, vol. 123, No. 26, pp. 6417-6418, American Chemical Society.

Gaylord, Brent S., et al., "Water-Soluble Conjugated Oligomers: Effect of Chain Length and Aggregation on Photoluminescence-Quenching Efficiencies," *J. Am. Chem. Soc.*, Jun. 8, 2001, vol. 123, No. 26, pp. 6417-6418.

Gaylord, et al., "DNA detection using water-soluble conjugated polymers and peptide nucleic acid probes," PNAS, Aug. 20, 2002, vol. 99, No. 17, pp. 10954-10957.

Goldfinger et al., "Fused polycyclic aromatics via electrophile-induced cyclization reactions: application to the synthesis of graphite ribbons", *J. Am. Chem. Soc.*, 1994, vol. 116, pp. 7895-7896.

Halkyard, Carrie E., et al., "Evidence of Aggregate Formation for 2,5-Dialkylpoly (*p*-phenyleneethynylenes) in Solution and Thin Films," Macromolecules, Nov. 25, 1998, vol. 31, No. 25, pp. 8655-8659, American Chemical Society.

Halkyard, Carrie E., et al., "Evidence of Aggregate Formation for 2,5-Dialkylpoly (*p*-phenyleneethynylenes) in Solution and Thin Films," *Macromolecules*, Nov. 25, 1998, vol. 31, No. 25, pp. 8655-8659.

Harrison, Benjamin S., et al., "Amplified Fluorescence Quenching in a Poly(*p*-phenylene)-Based Cationic Polyelectrolyte," Journal of the American Chemical Society, Aug. 16, 2001, vol. 122, No. 35, pp. 8561-8562, American Chemical Society.

Harrison, Benjamin S., et al., "Amplified Fluorescence Quenching in a Poly(p-phenylene)-Based Cationic Polyelectrolyte," *J. Am. Chem. Soc.*, Aug. 16, 2001, vol. 122, No. 35, pp. 8561-8562.

Heeger, Peter S., et al., "Making Sense of Polymer-Based Biosensors," Proceedings of the National Academy of Sciences of the United States of America, Oct. 26, 1999, vol. 96, No. 22, pp. 12219-12221.

Heeger, Peter S., et al., "Making Sense of Polymer-Based Biosensors," Proceedings of the National Academy of Sciences of the United States of America, Oct. 26, 1999, vol. 96, No. 22, pp. 12219-12221.

Höger, Sigurd, et al., "Synthesis, Aggregation, and Adsorption Phenomena of Shape-Persistent Macrocycles with Extraannular Polyalkuly Substituents," *J. Am. Chem. Soc.*, May 22, 2001, vol. 123, No. 24, pp. 5651-5659.

Institute for Soldier Nanotechnologies, (http://web.mit.edu/isn/industryday/index.html).

Jones, R.M., el al., "Superquenching and Its Applications in J-Aggregated Cyanine Polymers," Langmuir 2001, vol. 17, pp. 2568-2571.

Jones, Robert M., et al., "Superquenching and Its Application in J-Aggregated Cyanine Polymers," *Langmuir*, Apr. 4, 2001, vol. 17, No. 9, pp. 2568-2571.

Kim, et al., "Ultrafast Energy-Transfer Dynamics between Block Copolymer and π-Conjugated Polymer Chains in Blended Polymeric Systems," Chemistry of Materials, vol. 13(8), pp. 266-2674.

Kim, J., et al., "Nanoscale Fibrils and Grids: Aggregated Structures from Rigid-Rod Conjugated Polymers," Macromolecules, vol. 32, No. 5, pp. 1500-1507, 1999.

Kim, Jinsang, et al., "Control of conformational and interpolymer effects in conjugated polymers," *Nature*, Jun. 28, 2001, vol. 411, pp. 1030-1034.

Kim, Jinsang, et al., "Directing Energy Transfer within Conjugated Polymer Thin Films," *J. Am. Chem. Soc.*, Nov. 21, 2001, vol. 123, No. 46, pp. 11488-11489.

Kim, Jinsang, et al., "Ion-Specific Aggregation in Conjugated Polymers: Highly Sensitive and Selective Fluorescent Ion Chemosensors," *Agnew Chem. Int. Ed.*, 2000, vol. 39, No. 21, pp. 3868-3872.

Kim, Jinsang, et al., "Nanoscale Fibrils and Grids: Aggregated Structures from Rigid-Rod Conjugated Polymers," *Macromolecules*, vol. 32, No. 5, pp. 1500-1507, 1999.

Kim, Jinsang, et al., "Structural Control in Thin Layers of Poly)P-phenyleneethynylene)s: Photophysical Studies of Langmuir and Langmuir-Blodgett Films," *J. Am. Chem. Soc.*, Jul. 3, 2002, vol. 124, No. 26, p. 7710-7718.

Kim, Yong Hee, et al., "Ultrafast Energy-Transfer Dynamics between Block Copolymer and π-Conjugated Polymer Chains in Blended Polymeric Systems," *Chemistry of Materials*, vol. 13(8), pp. 266.

Köhler, Bernhard, et al., "Novel Chiral Macrocycles Containing Two Electronically Interacting Arylene Chromophores," *Chem. Eur. J.*, 2001, vol. 7, No. 14, pp. 3000-3004.

Kraft, Arno, et al., "Electroluminescent Conjugated Polymers—Seeing Polymers in a New Light," *Agnew. Chem. Int. Ed.* 1998, 37, 402-428.

Kraft, et al., "Electroluminescent Conjugated Polymers—Seeing Polymers in a New Light," Agnew. Chem. Int. Ed. 1998, 37, 402-428.

Kushon, et al., "Detection of DNA Hybridization via Fluorescent Polymer Superquenching," The ACS Journal of Surfaces and Colloids, Oct. 1, 2002, vol. 18., No. 20.

Kushon, Stuart A., et al., "Detection of DNA Hybridization via Fluorescent Polymer Superquenching," *Langmuir*, The ACS Journal of Surfaces and Colloids, Oct. 1, 2002, vol. 18, No. 20, pp. 7245-7249.

Laibin, Luo, et al., "Thermodynamic Stabilization Mechanism of Block Copolymer Vesicles," Journal of the American Chemical Society, 2001, vol. 123, No. 5, pp. 1012-1013, American Chemical Society.

Langveld, B.M.W., et al., "Circular Dichroism Circular Polarization of Photoluminescence of Highly Ordered Poly{3,4-di[(S)-2-methylbutoxy]thiophene}," *J. Am. Chem. Soc.*, 1996, vol. 118, No. 20, pp. 4908-4909.

Levitsky, I.A., et al., "Energy Migration in a Poly(phenylene ethynylene): Determination of Interpolymer Transport in Anistropic Langmuir-Blodgett Films," J.Am.Chem.Soc., vol. 121, No. 7, pp. 1466-1472, 1999.

Levitsky, Igor A., et al., "Energy Migration in a Poly(phenylene ethynylene): Determination of Interpolymer Transport in Anisotropic Langmuir-Blodgett Films," *J. Am. Chem. Soc.*, 1999, vol. 121, No. 7, pp. 1466-1472.

Levitsky, Igor A., et al., "Mass and Energy Transport in Conjugated Polylmer Langmuir-Blodgett Films; Conductivity, Fluorescence, and UV-Vis Studies," *Macromolecules*, Mar. 27, 2001, vol. 34, No. 7, pp. 2315-2319.

Li, Mei, et al., "Novel Surfactant-Free Stable Colloidal Nanoparticles Made of Randomly Carboxylated Polystyrene Ionomers," Macromolecules, 1997, vol. 30, No. 7, pp. 2201-2203, American Chemical Society.

Li, Mei, et al., "Novel Surfactant-Free Stable Colloidal Nanoparticles Made of Randomly Carboxylated Polystyrene Ionomers," *Macromolecules*, 1997, vol. 30, No. 7, pp. 2201-2203.

Luo, Laibin, et al., "Thermodynamic Stabilization Mechanism of Block Copolymer Vesicles," *J. Am. Chem. Soc.*, 2001, vol. 123, No. 5, pp. 1012-1013.

McQuade, D. Tyler et al., "Conjugated Polymer-Based Chemical Sensors," *Chem. Rev.*, 2000, vol. 100, No. 7, pp. 2537-2574.

McQuade, D. Tyler, et al., "Two-Dimensional Conjugated Polymer Assemblies: Interchain Spacing for Control of Photophysics," *J. Am. Chem. Soc.*, 2000, vol. 122, No. 24, pp. 5885-5886.

Miao, Yi-Jun, et al., "Fluorescence Sensory Polymers Containing Rigid Non-planar Aromatic Scaffolds," Proceedings of the 1997 Boston meeting, vol. 39, No. 2, pp. 1081-1082, Aug. 23-27, 1998, Polym. Prepr. Div. Polym. Chem. Am .Chem .Soc.; Polymer Preprints, Division of Polymer Chemistry, American Chemical Society, Aug. 1998 ACS, Washington D.C.

Miao, Y-J, et al., "Fluorescence Sensory Polymers Containing Rigid Non-planar Aromatic Scaffolds," Proceedings of the 1997 Boston meeting, vol. 39, No. 2, pp. 1081-1082, Aug. 23-27, 1998, Polym. Prepr.Div.Polym.Chem.Am.Chem.Soc.; Polymer Preprints, Division of Polymer Chemistry, American Chemical Society, Aug. 1998 ACS, Washington, D.C.

Mitschke, Ullrich et al., "The electroluminescence of organic materials," *J. Mater. Chem.*, 2000, vol. 10, pp. 1471-1507.

Moon, Joong Ho, et al., "Capture and detection of a quencher labeled oligonucleotide by poly)phenylene ethynylene) particles," *Chem. Commun.*, Jan. 2003, vol. 1, pp. 104-105.

Norvez, S., et al., "Epitaxygens: mesomorphic properties of triptycene derivatives," *Liquid Chemicals*, 1993, vol. 14, No. 5, pp. 1389-1395.

Oda, Masao, et al., "Chiroptical properties of chiral-substituted polyfluorenes," *Synthetic Metals*, 2000, vol. 111-112, pp. 575-577.

Oda, Masao, et al., "Circularly Polarized Electroluminescence from Liquid-Crystalline Chiral Polyfluorenes," *Advanced Materials*, 2000, vol. 12, No. 5, pp. 362-365.

Peeters, Emiel, et al., "Circularly Polarized Electroluminescence from a Polymer Light-Emitting Diode," *J. Am. Chem. Soc.*, 1997, vol. 119, No. 41, pp. 9909-9910.

Peng, et al., "Efficient Light Harvesting by Sequential Energy Transfer across Aggregates in Polymers of Finite Conjugational Segments with short Aliphatic Linkages," J. Am. Chem. Soc., 2001, vol. 123, pp. 11388-11397.

Peng, Kang-Yung, et al., "Efficient Light Harvesting by Sequential Energy Transfer across Aggregates in Polymers of Finite Conjugational Segments with Short Aliphatic Linkages," *J. Am. Chem. Soc.*, 2001, vol. 123, pp. 11388-11397.

Place, Ileana, et al., "Stabilization of the Aggregation of Cyanine Dyes at the Molecular and Nanoscopic Level," Langmuir, Jul. 28, 2000, vol. 16, No. 23, pp. 9042-9048, American Chemical Society.

Place, Ileane, et al., "Stabilization of the Aggregation of Cyanine Dyes at the Molecular and Nanoscopic Level," *Langmuir*, Jul. 28, 2000, vol. 16, No. 23, pp. 9042-9048.

Pschirer, Neil G., et al., "Poly(fluorenyleneethynylene)s by Alkyne Metathesis: Optical Properties and Aggregation Behavior," *Macromolecules*, May 9, 2000, vol. 33, No. 11, pp. 3961-3963.

Pschirer, Niel G., et al.,"Poly(fluorenyleneethynylene)s by Alkyne Metathesis: Optical Properties and Aggregation Behavior," Macromolecules, May 9, 2000, vol. 33, No. 11, pp. 3961-3963, American Chemical Society.

Sigurd, Höger, et al., "Synthesis, Aggregation, and Adsorption Phenomena of Shape-Persistent Macrocycles with Extraannular Polyalkuly Substituents," Journal of the American Chemical Society, May 22, 2001, vol. 123, No. 24, pp. 5651-5659, American Chemical Society.

Snow A. W., et al., "Synthesis and Evaluation of Hexafluorodimethylcarbinol Functionalized Polymers as Microsensor Coatings," Journal of Applied Polymer Science, 1991, vol. 43, pp. 1659-1671.

Snow, A. W., et al., "Synthesis and Evaluation of Hexafluorodimethylcarbinol Functionalized Polymers as Microsensor Coatings," Journal of Applied Polymer Science, vol. 43, pp. 1659-1671, 1991.

Swager, T.M., "The Molecular Wire Approach to Sensory Signal Amplification," Acc.Chem.Res., vol. 31, No. 5, pp. 201-207, 1998.

Swager, T.M., et al., "Fluorescence Studies of Poly(p-phenyleneethynylene)s: The Effect of Anthracene Substitution," J.Phys.Chem., vol. 99, No. 14, pp. 4886-4893, 1995.

Swager, Timothy M., "The Molecular Wire Approach to Sensory Signal Amplification," Acc. Chem. Res., 1998, vol. 31, No. 5, pp. 201-207.

Swager, Timothy M., et al., "Fluorescence Studies of Poly(p-phenyleneethynylene)s: The Effect of Anthracene Substitution," J. Phys .Chem., 1995, vol. 99, No. 14, pp. 4886-4893.

Tan, Chunyan, et al., "Photophysics, aggregation and amplified quenching of a water-soluble poly(phenylene ethynylene)," Chem. Commun., 2002, pp. 446-447.

Tan, et al., "Photophysics, aggregation and amplified quenching of a water-soluble poly(phenylene ethynylene)," Chem. Commun., 2002, pp. 446-447.

Van Houten, K.A., et al., "Rapid Luminescent Detection of Phosphate Esters in Solution and the Gas Phase Using (dppe)Pt{$S_2C_2$(2-pyridyl)($CH_2CH_2OH$)}," J..Am.Chem.Soc., vol. 120, No. 47, pp. 12359-12360, 1998.

Van Houten, Kelly A., et al., "Rapid Luminescent Detection of Phosphate Esters in Solution and the Gas Phase Using (dppe)Pt{S2C2(2-pyridyl)(CH2CH2OH)}," J. Am. Chem. Soc., 1998, vol. 120, No. 47, pp. 12359-12360.

Walters, et al., "Photophysical Consequences of Conformation and Aggregation in Dilute Solutions of $\pi$-Conjugated Oligomers," Langmuir, 1999, vol. 15, pp. 5676-5680.

Walters, Keith A., et al., "Photophysical Consequences of Conformation and Aggregation in Dilute Solutions of $\pi$-Conjugated Oligomers," Langmuir, 1999, vol. 15, pp. 5676-5680.

Weder, C. & Wrighton, M.S., Efficient Solid-State Photoluminescence in New Poly(2,5-dialkoxy-p-phenyleneethynylene)s Macromolecules, vol. 29, No. 15, pp. 5157-5165, 1996.

Weder, Christoph, et al., "Efficient Solid-State Photoluminescence in New Poly(2,5-dialkoxy-p-phenyleneethynylene)s," Macromolecules, 1996, vol. 29, No. 15, pp. 5157-5165.

Wu, Chi, et al., "Novel Nanoparticles Formed via Self-Assembly of Poly(ethylene glycol-b-sebacic anhydride) and Their Degradation in Water," Macromolecules, Oct. 31, 2000, vol. 33, No. 24, pp. 9040-9043, American Chemical Society.

Wu, Chi, et al., "Novel Nanoparticles Formed via Self-Assembly of Poly(ethylene glycol-b-sebacic anhydride) and Their Degradation in Water," Macromolecules, Oct. 31, 2000, vol. 33, No. 24, pp. 9040-9043.

Yang, J-S. & Swager, T.M., "Florescent Porous Polymer Films as TNT Chemosensors: Electronic and Structural Effects," J.Am.Chem. Soc., vol. 120, No. 46, pp. 11864-11873, 1998.

Yang, Jye-Shane, et al., "Anomalous crystal packing of iptycene secondary diamides leading to novel chain and channel networks," Tetrahedron Letters, Oct. 7, 2000, vol. 41, Issue 41, pp. 7911-7915.

Yang, Jye-Shane, et al., "Fluorescent Porous Polymer Films as TNT Chemosensors: Electronic and Structural Effects," J. Am. Chem. Soc., 1998, vol. 120, No. 46, pp. 11864-11873.

Yang, Jye-Shane, et al., "Porous Shape Persistent Fluorescent Polymer Films: An Approach to TNT Sensory Materials," J. Am. Chem. Soc., Jun. 3, 1998, vol. 120, No. 21, pp. 5321-5322.

Zhang, Guangzhao, et al., "Formation of Novel Polymeric Nanoparticles," Accounts of Chemical Research, Jan. 6, 2001, vol. 34, No. 3, pp. 249-256, American Chemical Society.

Zhang, Guangzhao, et al., "Formation of Novel Polymeric Nanoparticles," Accounts of Chemical Research, Jan. 6, 2001, vol. 34, No. 3, pp. 249-256.

Zhang, Shi-Wei, et al., "Fluorescent Detection of Chemical Warfare Agents: Specific Ratiometric Chemosensors," J. Am. Chem. Soc., vol. 125, pp. 3420-3423.

Zhang, Shi-Wei, et al., "Fluorescent Detection of Chemical Warfare Agents: Functional Group Specific Ratiometric Chemosensors," Supporting Information, (http://pubs.acs.org/subscribe/journals/jacsat/suppinfo/ja029265z/ja029265zsi20030125_030500.pdf).

Zhou, Q. & Swager, T.M., "Methodology for Enhancing the Sensitivity of Fluorescent Chemosensors: Energy Migration In Conjugated Polymers," Journal of the American Chemical Society, vol. 117, No. 26, pp. 7017-7018, 1995.

Zhou, Q. and Swager, T.M., "Fluorescent Chemosensors Based on Energy Migration in Conjugated Polymers: The Molecular Wire Approach to Increased Sensitivity," J.Am.Chem.Soc., vol. 117, No. 50, pp. 12593-12602, 1995.

Zhou, Qin, et al. "Fluorescent Chemosensors Based on Energy Migration in Conjugated Polymers: The Molecular Wire Approach to Increased Sensitivity," J. Am. Chem. Soc., 1995, vol. 117, No. 50, pp. 12593-12602.

Zhou, Qin, et al., "Methodology for Enhancing the Sensitivity of Fluorescent Chemosensors: Energy Migration In Conjugated Polymers," J. Am. Chem. Soc., 1995, vol. 117, No. 26 pp. 7017-7018.

Achyuthan et al., "Fluorescence Superquenching of Conjugated Polyelectrolytes: Applications for Biosensing and Drug Discovery," J. Mat. Chem. 2005, 15, 2648.

Bergstedt et al., "Superquenching of Fluorescent Polyelectrolytes and its Applications for Chemical and Biological Sensing," Proc. SPIE 2001, 4279, 94.

Brabec et al. "Plastic Solar Cells," Adv. Funct. Mater. 2001, 11(1), 15.

Chen et al., "Surfactant-induced Modification of Quenching of Conjugated Polymer Fluorescence by Electron Acceptors: Applications for Chemical Sensing," Chem. Phys. Lett. 2000, 330, 27.

Chen et al., "Highly sensitive biological and chemical sensors based on reversible fluorescence quenching in a conjugated polymer," PNAS 1999, 96(22), 12287.

Chen et al.,"Tuning the Properties of Conjugated Polyelectrolytes through Surfactant Complexation," J. Am. Chem. Soc. 2000, 122, 9302-9303.

Cotts et al., "Equilibrium Flexibility of a Rigid Linear Conjugated Polymer," Macromolecules 1996, 29, 7323.

Dagani, "A Better Sensor for Nerve Gas," C&E News, Mar. 10, 2003, 12.

Deans et al., "A Poly(p-phenyleneethynylene) with a Highly Emissive Aggregated Phase," J. Am. Chem. Soc. 2000, 122, 8565.

Fan et al., "High-Efficiency Fluorescence Quenching of Conjugated Polymers by Proteins," J. Am. Chem. Soc. 2002, 124, 5642.

Fan et al., "Photoluminescence Quenching of Water-Soluble, Conjugated Polymers by Viologen Derivatives: Effect of Hydrophobicity," Langmuir 2003, 19, 3554. Published on Web, Mar. 19, 2003.

Fan et al., "Beyond Superquenching: Hyper-Efficient Energy Transfer from Conjugated Polymers to Gold Nanoparticles," PNAS 2003, 100(11), 6297.

Fiesel, et al., "On the Solid State Aggregation of Chiral Substituted Poly(para-phenylene)s (PPPs)," Synthetic Metals 1999, 102, 1457.

Fiesel et al., "Aggregation-induced CD effects in chiral poly(2,5-dialkoxy-1,4-phenylene)s," Acta Polym. 1998, 49, 445.

Fiesel et al., "A chiral poly(para-phenyleneethynylene) (PPE) derivative," Macromol. Rapid Commun. 1998, 19(8), 427.

Fu et al., "Alternating Poly(PyridylVinylenePhenyleneVinylene)s: Synthesis and Solid State Organizations," Tetrahedron 1997, 53(45), 15487.

Gaylord et al., "DNA Hybridization Detection with Water-Soluble Conjugated Polymers and Chromophore-Labeled Single-Stranded DNA," J. Am. Chem. Soc. 2003, 125, 896.

Gaylord et al., "SNP Detection Using Peptide Nucleic Acid Probes and Conjugated Polymers: Applications in Neurodegenerative Disease Identification," PNAS 2005, 102(1), 34.

Gaylord et al., "DNA detection using water-soluble conjugated polymers and peptide nucleic acid probes," PNAS 2002, 99(17), 7245.

Gaylord et al., "Water-Soluble Conjugated Oligomers: Effect of Chain Length and Aggregation on Photoluminescence-Quenching Efficiencies," J. Am. Chem. Soc. 2001, 123(26), 6418.

Goldfinger et al., "Fused Polycyclic Aromatics via Electrophile-Induced Cyclization Reactions: Application to the Synthesis of Graphite Ribbons," J. Am. Chem. Soc. 1994, 116, 7895.

Halkyard et al., "Evidence of Aggregate Formation for 2,5-Dialkylpoly (p-phenyleneethynylenes) in Solution and Thin Films," Macromolecules 1998, 31(25), 8655.

Harrison et al., "Amplified Fluorescence Quenching in a Poly(p-phenylene)-Based Cationic Polyelectrolyte," J. Am. Chem. Soc. 2001, 122(35), 8561.

Heeger et al., "Making sense of polymer-based biosensors," PNAS 1999, 96(22), 12219.

Höger et al., "Synthesis, Aggregation, and Adsorption Phenomena of Shape-Persistent Macrocycles with Extraannular Polyalkyl Substituents," J. Am. Chem. Soc. 2001, 123(24), 5651.

Jones et al., "Building highly sensitive dye assemblies for biosensing from molecular building blocks," PNAS 2001, 98(26), 14769.

Jones et al., "Superquenching and Its Applications in J-Aggregated Cyanine Polymers," Langmuir 2001, 17, 2568.

Jones et al., "Tuning of Superquenching in Layered and Mixed Fluorescent Polyelectrolytes," J. Am. Chem. Soc. 2001, 123, 6726.

Jones et al., "Building Highly Sensitive Dye Assemblies for Biosensing from Molecular Building Blocks," PNAS 2001, 98(26), 14769.

Kim et al., "Nanoscale Fibrils and Grids: Aggregated Structures from Rigid-Rod Conjugated Polymers," Macromolecules 1999, 32(5), 1500.

Kim et al. et al., "Ion-Specific Aggregation in Conjugated Polymers: Highly Sensitive and Selective Fluorescent Ion Chemosensors," Angew. Chem. Int. Ed. 2000, 39(21), 3868.

Kim et al., "Control of conformational and interpolymer effects in conjugated polymers," Nature 2001, 411, 1030.

Kim et al., "Directing Energy Transfer within Conjugated Polymer Thin Films," J. Am. Chem. Soc. 2001, 123(46), 11488.

Kim et al., "Structural Control in Thin Layers of Poly)P-phenyleneethynylene)s: Photophysical Studies of Langmuir and Langmuir-Blodgett Films," J. Am. Chem. Soc. 2002, 124(26), 7710.

Kim et al., "Ultrafast Energy-Transfer Dynamics between Block Copolymer and π-Conjugated Polymer Chains in Blended Polymeric Systems," Chem. Mater. 2001, 13(8), 2666.

Köhler et al., "Novel Chiral Macrocycles Containing Two Electronically Interacting Arylene Chromophores," Chem. Eur. J., 2001, 7(14), 3000.

Kraft et al., "Electroluminescent Conjugated Polymers—Seeing Polymers in a New Light," Angew. Chem. Int. Ed. 1998, 37, 402.

Kumaraswamy et al., "Fluorescent-Conjugated Polymer Superquenching Facilitates Highly Sensitive Detection of Proteases," PNAS 2004, 101(24), 7511.

Kushon et al., "Detection of DNA Hybridization via Fluorescent Polymer Superquenching," Langmuir 2002, 18(20), 7245.

Kushon et al., "Detection of Single Nucleotide Mismatches via Fluorescent Polymer Superquenching," Langmuir 2003, 19, 6456.

Langveld et al., "Circular Dichroism and Circular Polarization of Photoluminescence of Highly Ordered Poly{3,4-di[(S)-2-methylbutoxy]thiophene}," J. Am. Chem. Soc. 1996, 118(20), 4908.

Levitsky et al., "Energy Migration in a Poly(phenylene ethynylene): Determination of Interpolymer Transport in Anisotropic Langmuir-Blodgett Films," J. Am. Chem. Soc. 1999, 121(7), 1466.

Levitsky et al., "Mass and Energy Transport in Conjugated Polymer Langmuir-Blodgett Films; Conductivity, Fluorescence, and UV-Vis Studies," Macromolecules 2001, 34(7), 2315.

Li et al., "Novel Surfactant-Free Stable Colloidal Nanoparticles Made of Randomly Carboxylated Polystyrene Ionomers," Macromolecules 1997, 30(7), 2201.

Liu et al., "Homogeneous Fluorescence-Based DNA Detection with Water-Soluble Conjugated Polymers," Chem Mater. 2004, 16, 4467.

Liu et al., "Optimization of the Molecular Orbital Energies of Conjugated Polymers for Optical Amplification of Fluorescent Sensors," J. Am. Chem. Soc. 2006, 128, 1188.

Liu et al., "Methods for Strand-Specific DNA Detection with Cationic Conjugated Polymers Suitable for Incorporation into DNA Chips and Microarray," PNAS 2005, 102(3), 589.

Lu, et al., "Superquenching in Cyanine Pendant Poly($_L$-lysine) Dyes: Dependence on Molecular Weight, Solvent, and Aggregation," J. Am. Chem. Soc. 2002, 124(3), 483.

Lu et al., "Surface-Enhanced Superquenching of Cyanine Dyes as J-Aggregates on Laponite Clay Nanoparticles," Langmuir 2002, 18, 7706.

Lu et al., "Biocidal Activity of a Light-Absorbing Fluorescent Conjugated Polyelectrolyte," Langmuir 2005, 21, 10154.

Lu et al., "'Cyanine Pendant' Polymers on Nanoparticles and in Solution; Superquenching and Sensing Applications," Polym. Mat. Sci. Eng. 2002, 86, 17.

Lu et al., "Self-Assembled 'Polymers' on Nanoparticles: Superquenching and Sensing Applications," Polymer Preprints, 2002, 43, 124.

Luo et al., "Thermodynamic Stabilization Mechanism of Block Copolymer Vesicles," J. Am. Chem. Soc. 2001, 123(5), 1012.

McQuade et al., "Two-Dimensional Conjugated Polymer Assemblies: Interchain Spacing for Control of Photophysics," J. Am. Chem. Soc. 2000, 122(24), 5885.

McQuade et al., "Conjugated Polymer-Based Chemical Sensors," Chem. Rev. 2000, 100(7), 2537.

Miao et al., "Fluorescence Sensory Polymers Containing Rigid Nonplanar Aromatic Scaffolds," Proceedings of the 1997 Boston meeting, vol. 39, No. 2, pp. 1081-1082, Aug. 23-27, 1998, Polym. Prepr. Div. Polym. Chem. Am .Chem .Soc.; Polymer Preprints, Dvision of Polymer Chemistry, American Chemical Society, Aug. 1998 ACS, Washington D.C.

Mitschke et al., "The electroluminescence of organic materials," J. Mater. Chem. 2000, 10, 1471.

Moon et al., "Capture and detection of a quencher labeled oligonucleotide by poly)phenylene ethynylene) particles," Chem. Commun. 2003, 1, 104.

Norvez et al., "Epitaxygens: mesomorphic properties of triptycene derivatives," Liquid Chemicals 1993, 14(5), 1389.

Oda et al., "Circularly Polarized Electroluminescence from Liquid-Crystalline Chiral Polyfluorenes," Adv. Mater. 2000, 12(5), 362.

Oda et al., "Chiroptical properties of chiral-substituted polyfluorenes," Synthetic Metals 2000, 111-112, 575.

Peng et al., "Efficient Light Harvesting by Sequential Energy Transfer across Aggregates in Polymers of Finite Conjugational Segments with Short Aliphatic Linkages," J. Am. Chem. Soc. 2001, 123, 11388.

Peeters et al., "Circularly Polarized Electroluminescence from a Polymer Light-Emitting Diode," J. Am. Chem. Soc. 1997, 119(41), 9909.

Place et al., "Stabilization of the Aggregation of Cyanine Dyes at the Molecular and Nanoscopic Level," Langmuir 2000, 16(23), 9042.

Pschirer et al., "Poly(fluorenyleneethynylene)s by Alkyne Metathesis: Optical Properties and Aggregation Behavior," Macromolecules 2000, 33(11), 3961.

Rininsland et al., "High-Throughput Kinase Assays with Protein Substrates Using Fluorescent Polymer Superquenching," MBC Biotech. 2005, 5, 16.

Rininsland et al., "Metal Ion-Mediated Polymer Superquenching for Highly Sensitive Detection of Kinase and Phosphatase Activities," PNAS 2004, 101(43), 15295.

Snow et al., "Synthesis and Evaluation of Hexafluorodimethylcarbinol Functionalized Polymers as Microsensor Coatings," J. Applied Polymer Science 1991, 43, 1659.

Swager et al., "Fluorescence Studies of Poly(p-phenyleneethynylene)s: The Effect of Anthracene Substitution," J. Phys .Chem. 1995, 99(14), 4886.

Swager, "The Molecular Wire Approach to Sensory Signal Amplification," Acc. Chem. Res. 1998, 31(5), 201.

Tan et al., "Photophysics, aggregation and amplified quenching of a water-soluble poly(phenyleneethynylene)," Chem. Commun. 2002, 446.

Van Houten et al., "Rapid Luminescent Detection of Phosphate Esters in Solution and the Gas Phase Using (dppe)Pt{S2C2(2-pyridyl)(CH2CH2OH)}," J. Am. Chem. Soc. 1998, 120(47), 12359.

Walters et al., "Photophysical Consequences of Conformation and Aggregation in Dilute Solutions of π-Conjugated Oligomers," Langmuir 1999, 15, 5676.

Wang et al., "Fluorescein Provides a Resonance Gate for FRET from Conjugated Polymers to DNA Intercalated Dyes," J. Am. Chem. Soc. 2004, 126, 5446.

Wang et al., "Photoluminescence Quenching of Conjugated Macromolecules by Bipyridinium Derivatives in Aqueous Media: Charge Dependence," Langmuir 2001, 17, 1262.

Wang et al., "Photoluminescence of Water-Soluble Conjugated Polymers: Origin of Enhanced Quenching by Charge Transfer," Macromolecules 2000, 33, 5153.

Wang et al., "Biosensors from Conjugated Polyelectrolyte Complexes," PNAS 2002, 99(1), 49.

Weder et al., "Efficient Solid-State Photoluminescence in New Poly(2,5-dialkoxy-p-phenyleneethynylene)s," Macromolecules 1996, 29(15), 5157.

Whitten et al., "From Superquenching to Biodetection: Building Sensors Based on Fluorescent Polyelectrolytes," Chapter 4, *Optical Sensors and Switches*, New York: Marcel Dekker, 2001.

Wu et al., "Novel Nanoparticles Formed via Self-Assembly of Poly-(ethylene glycol-b-sebacicanhydride) and Their Degradation in Water," Macromolecules 2000, 33(24), 9040.

Xia et al., "Applications of Fluorescent Polymer Superquenching to High Throughput Screening Assays for Protein Kinases," Assay and Drug Dev. Tech. 2004, 2, 183.

Xia et al., "A High-Throughput Screening Assay for Kinases and Phosphatases via Metal Ion-Mediated Fluorescent Polymer Superquenching," American Laboratory 2004, 36, 15.

Yang et al., "Fluorescent Porous Polymer Films as TNT Chemosensors: Electronic and Structural Effects," J. Am. Chem. Soc. 1998, 120(46), 11864.

Yang et al., "Porous Shape Persistent Fluorescent Polymer Films: An Approach to TNT Sensory Materials," J. Am. Chem. Soc. 1998, 120(21), 5321.

Yang et al., "Anomalous crystal packing of iptycene secondary diamides leading to novel chain and channel networks," Tet. Lett. 2000, 41(41), 7911.

Zhang et al., "Formation of Novel Polymeric Nanoparticles," Acc. Chem. Res. 2001, 34(3), 249.

Zhang et al., "Fluorescent Detection of Chemical Warfare Agents: Specific Ratiometric Chemosensors," J. Am. Chem. Soc., vol. 125, pp. 3420-3423.

Zhang et al., "Fluorescent Detection of Chemical Warfare Agents: Functional Group Specific Ratiometric Chemosensors," Supporting Information, (http://pubs.acs.org/subscribe/journals/jacsat/suppinfo/ja029265z/ja029265zsi20030125_030500.pdf).

Zhou et al. "Fluorescent Chemosensors Based on Energy Migration in Conjugated Polymers: The Molecular Wire Approach to Increased Sensitivity," J. Am. Chem. Soc. 1995, 117(50), 12593.

Zhou et al., "Methodology for Enhancing the Sensitivity of Fluorescent Chemosensors: Energy Migration In Conjugated Polymers," J. Am. Chem. Soc. 1995, 117(26), 7017.

Institute for Soldier Nanotechnologies, (http://web.mit.edu/isn/industryday/index.html).

* cited by examiner

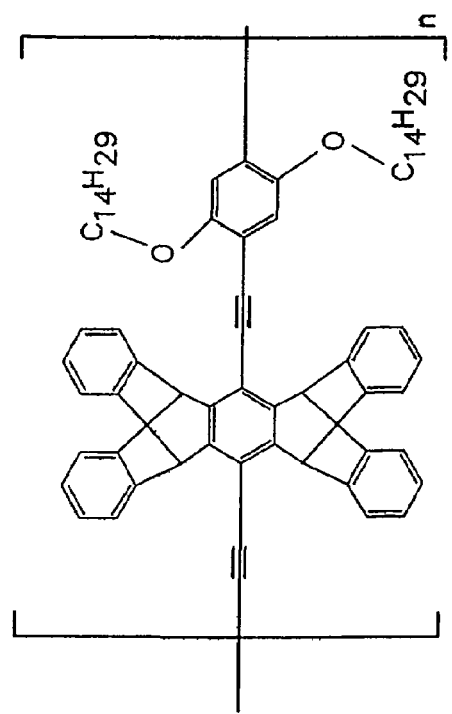
FIG. 6a(2)
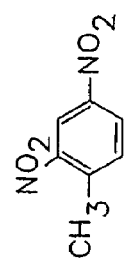
FIG. 6a(3)
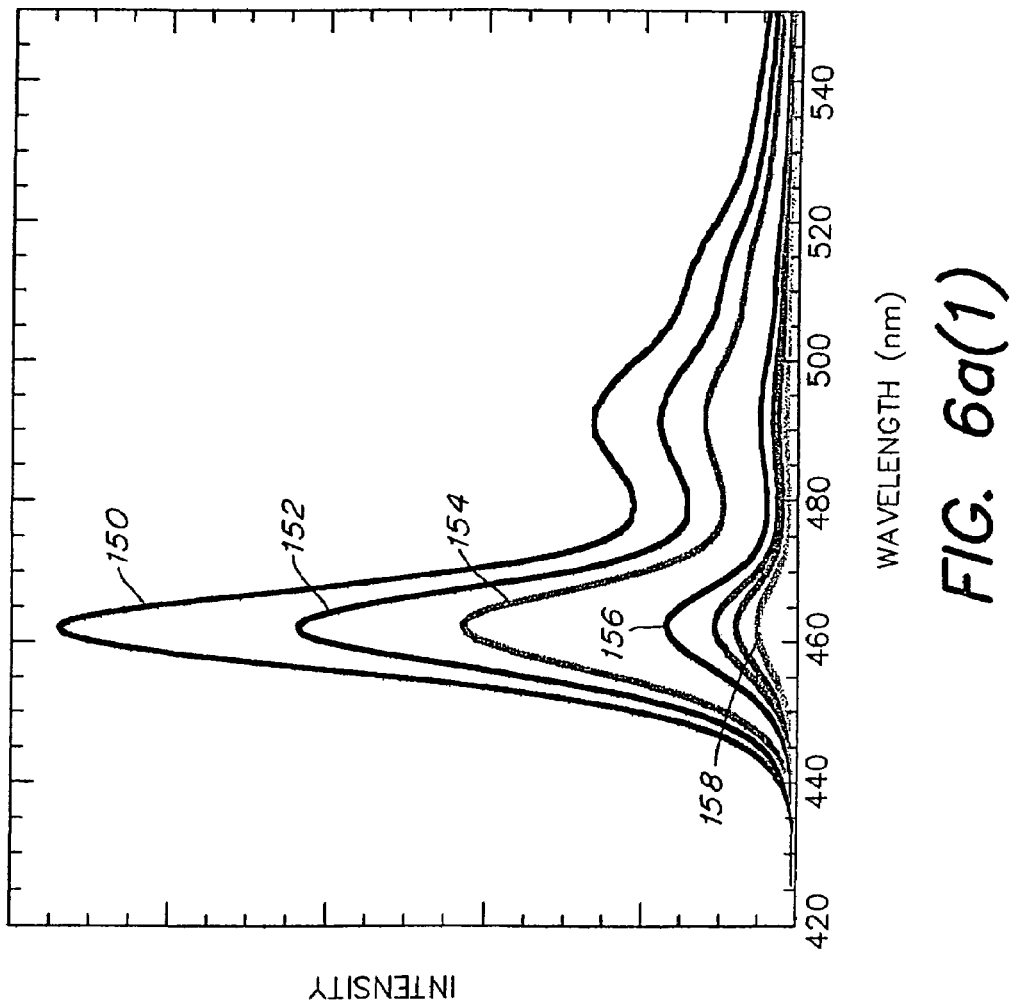
FIG. 6a(1)

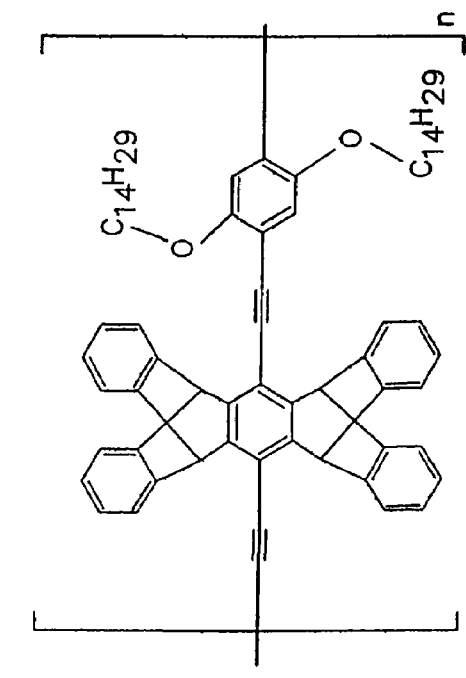
FIG. 6b(2)
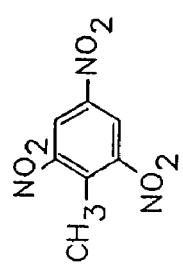
FIG. 6b(3)
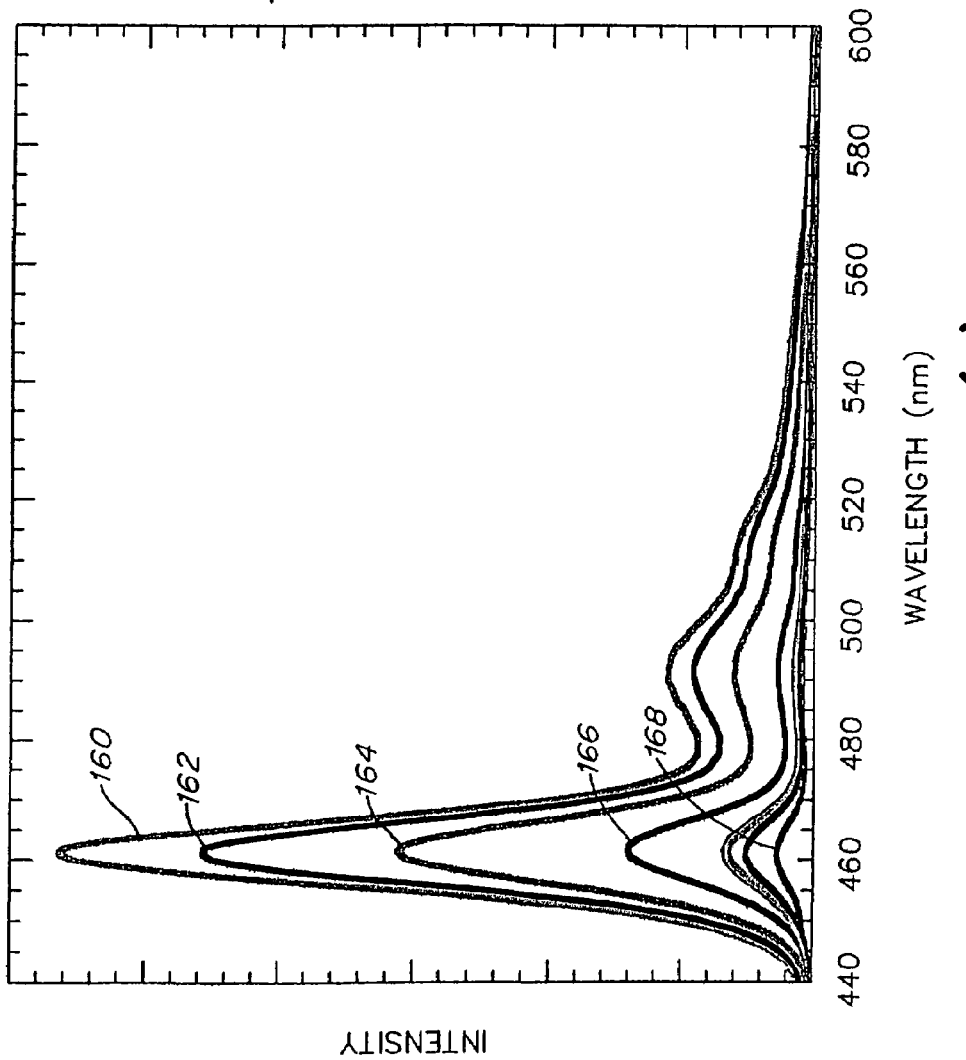
FIG. 6b(1)

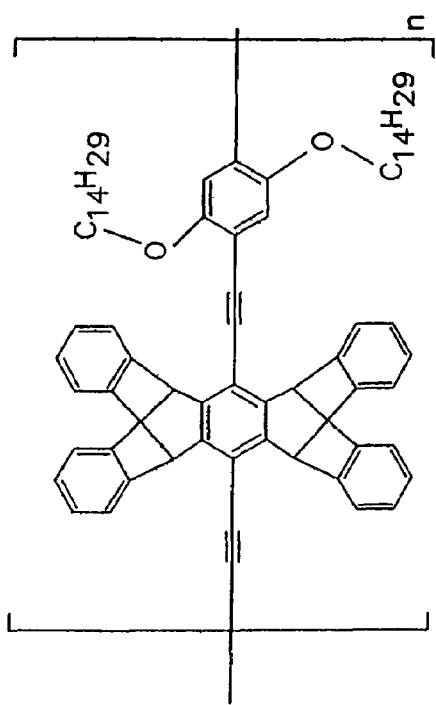
FIG. 6c(2)
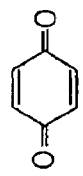
FIG. 6c(3)
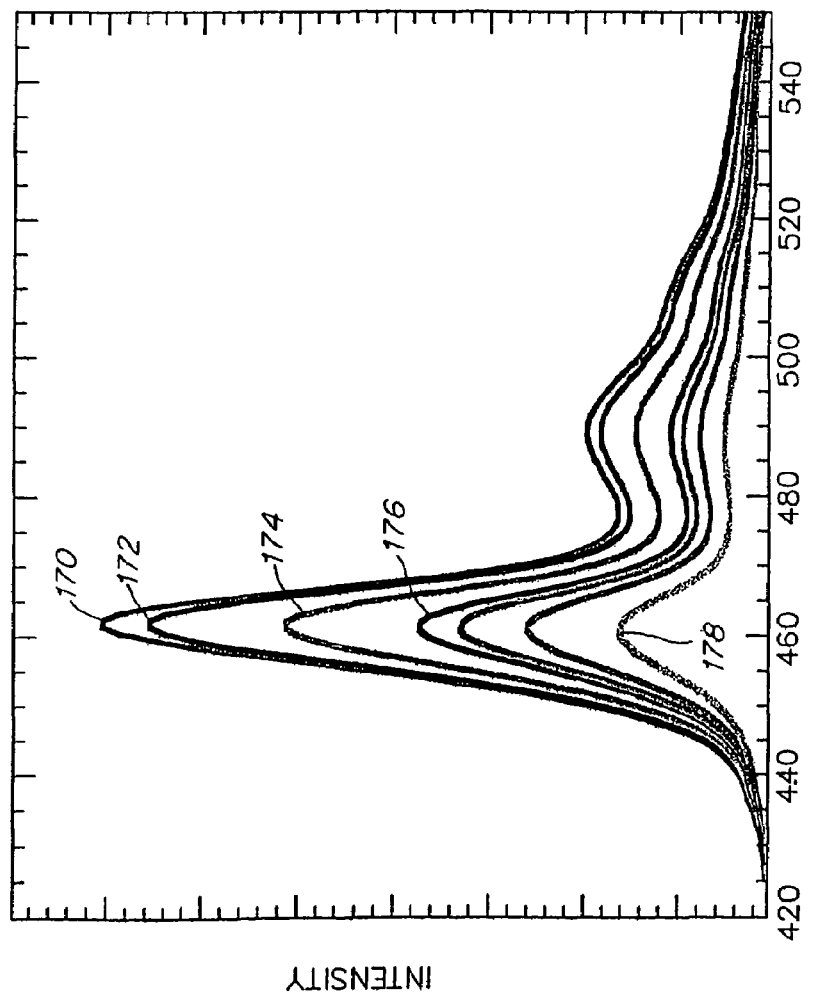
FIG. 6c(1)

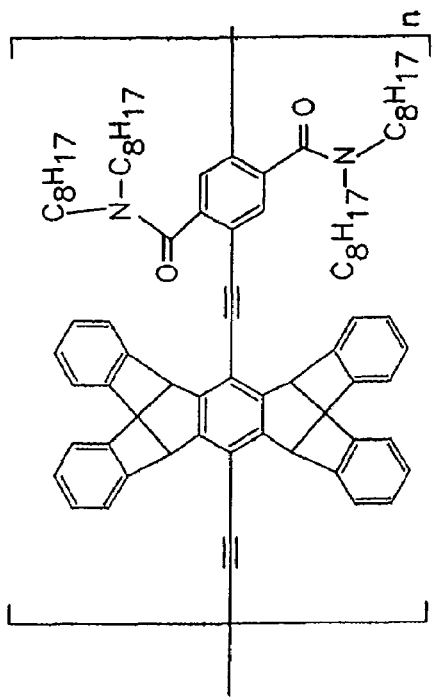
FIG. 6d(2)
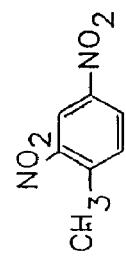
FIG. 6d(3)
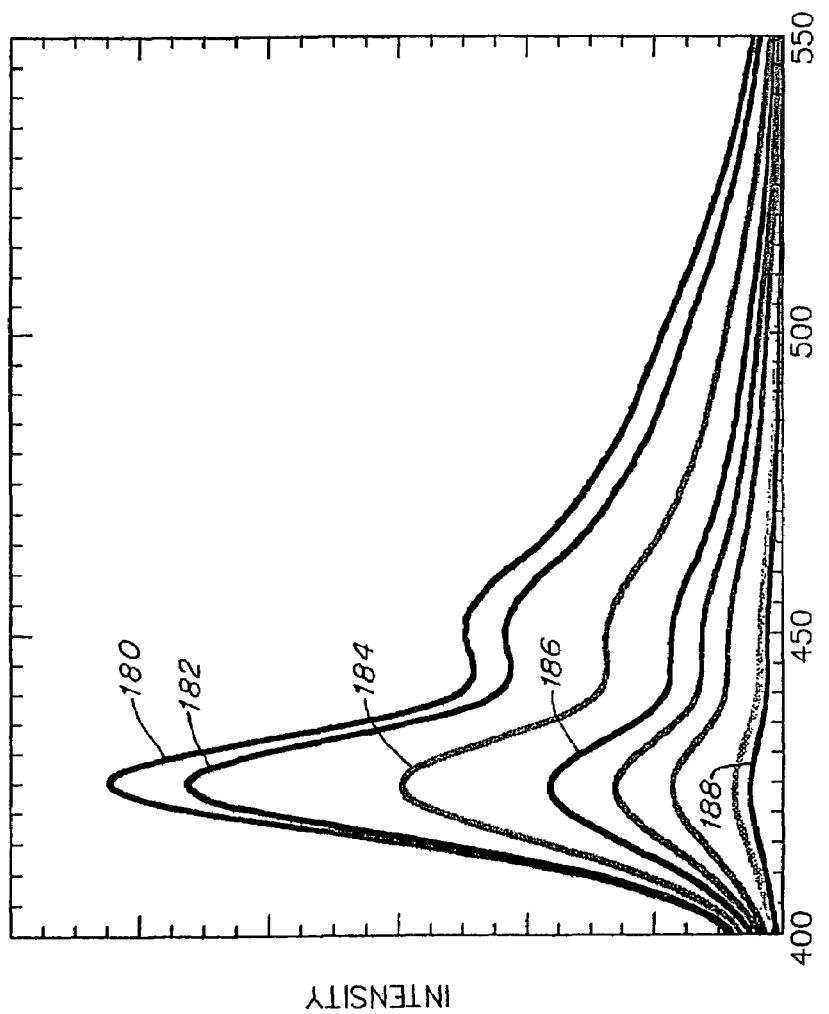
FIG. 6d(1)

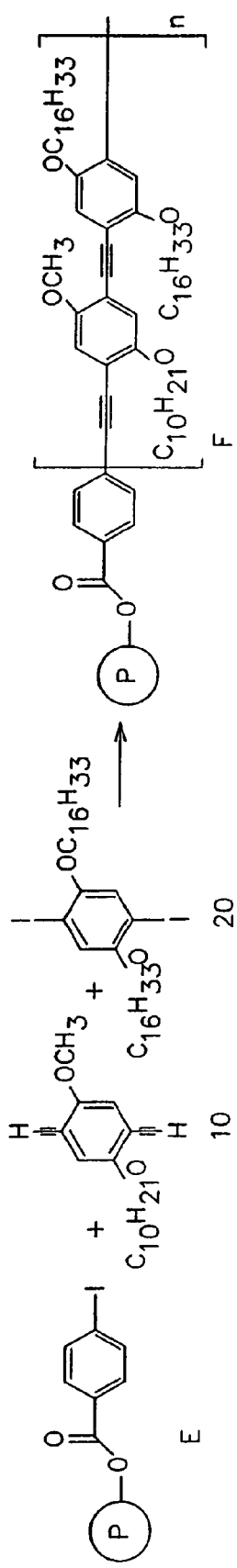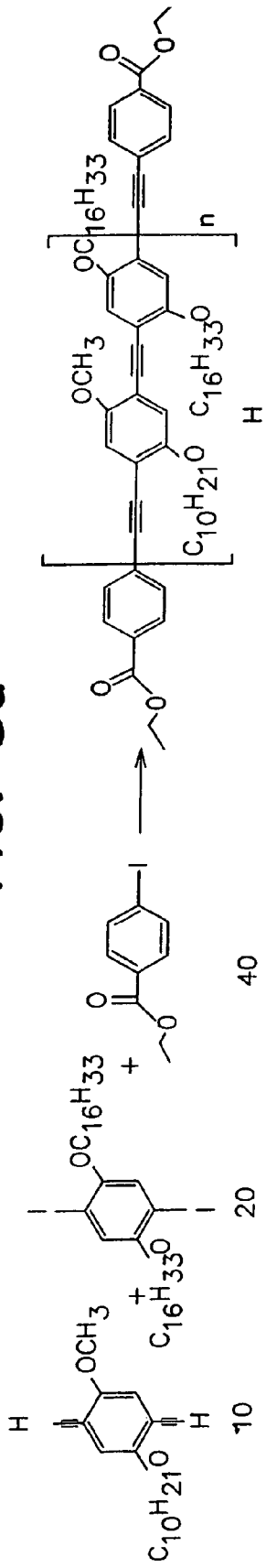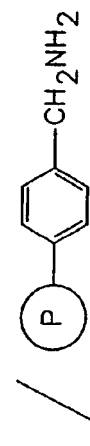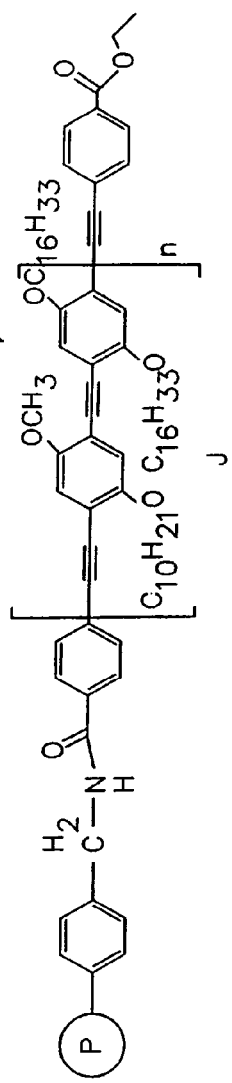
FIG. 8a
FIG. 8b

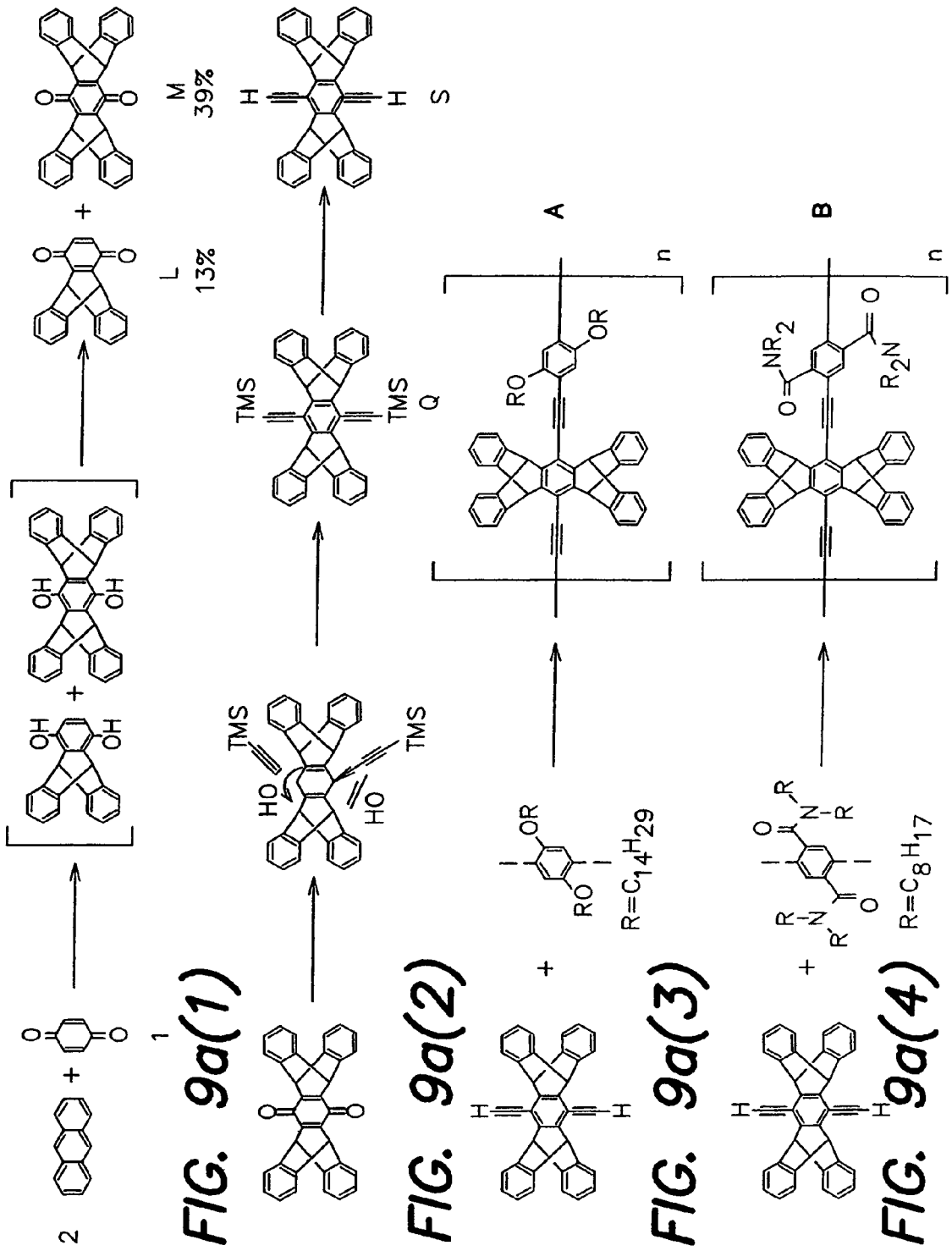
FIG. 9a(1)
FIG. 9a(2)
FIG. 9a(3)
FIG. 9a(4)

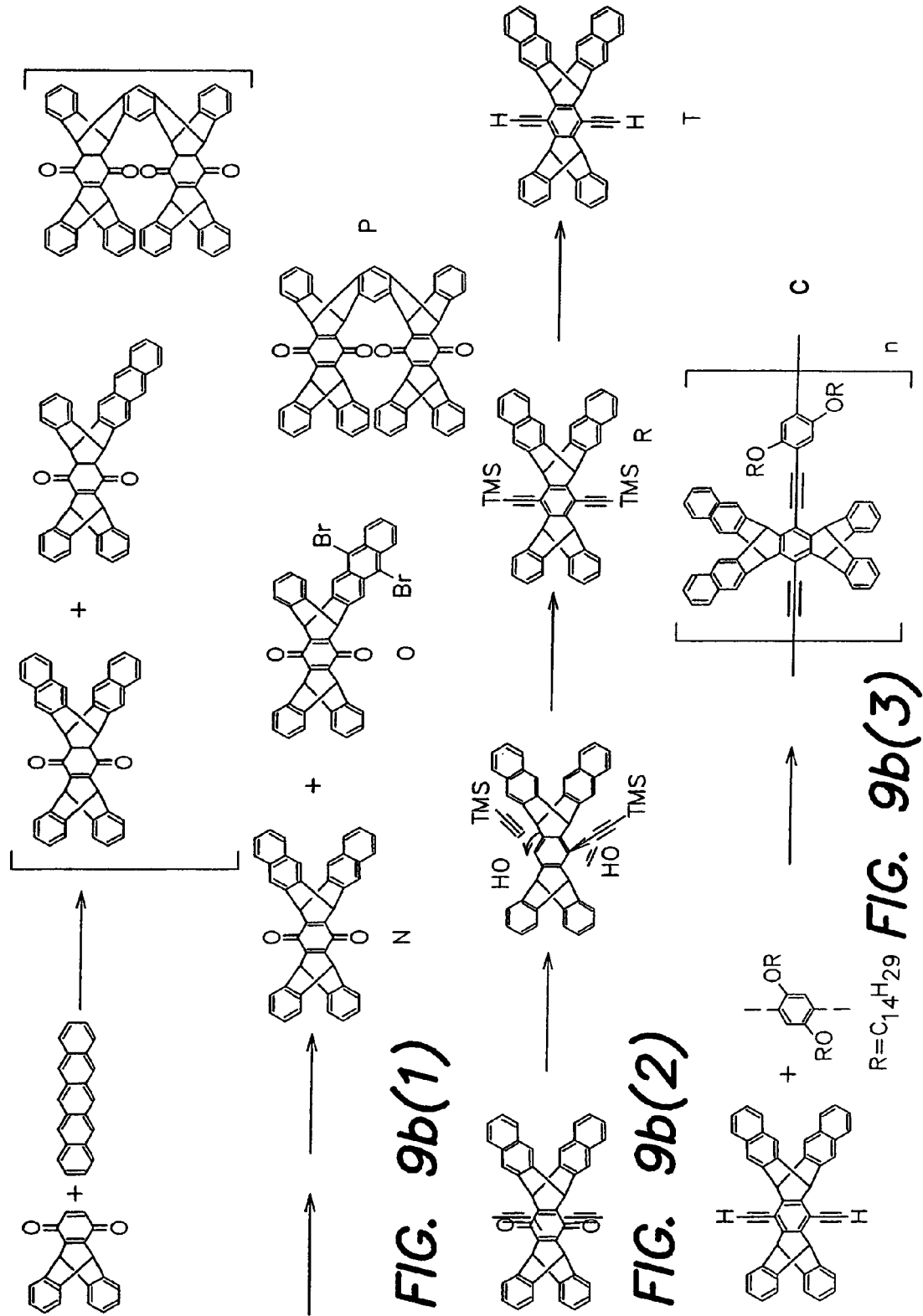
FIG. 9b(1)   FIG. 9b(2)   FIG. 9b(3)

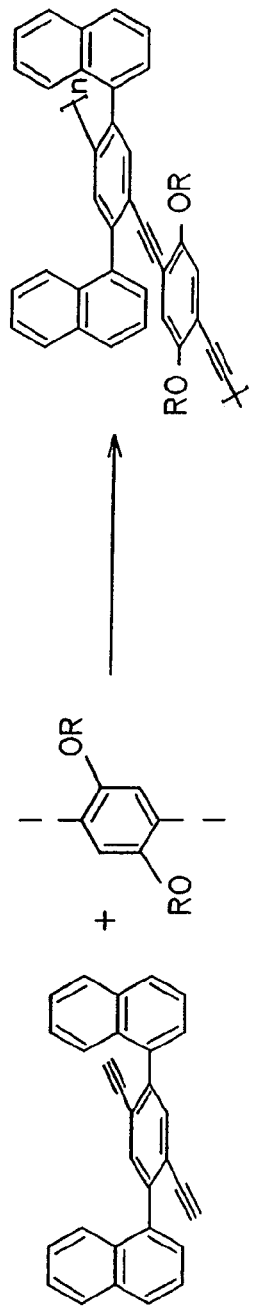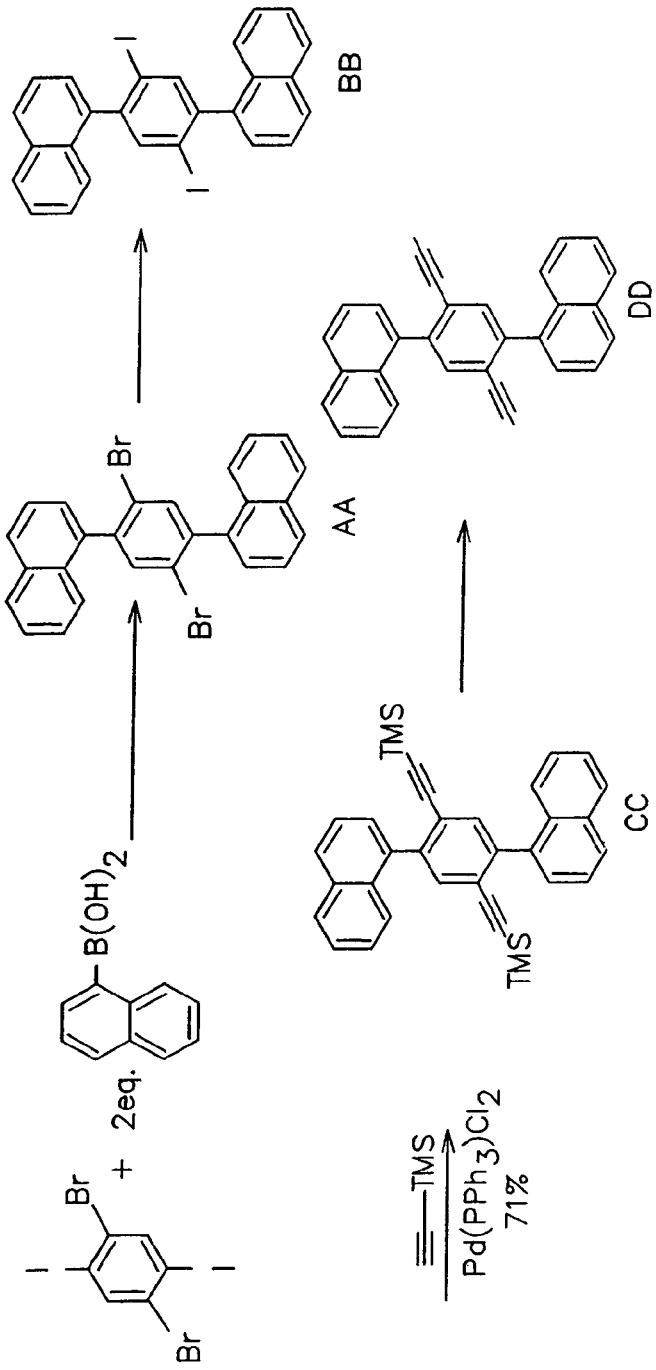
FIG. 10a
FIG. 10b

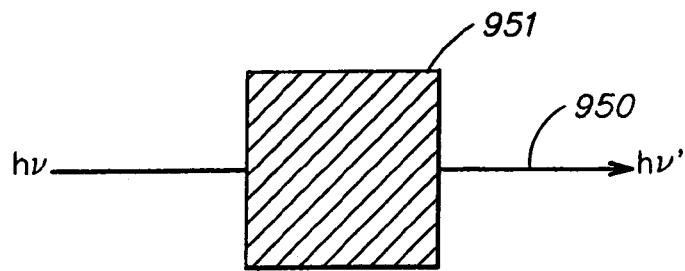
FIG. 11a(1)
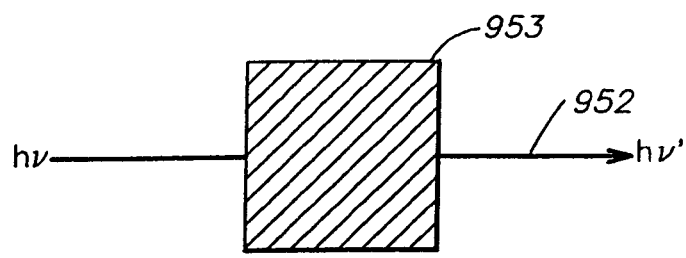
FIG. 11a(2)
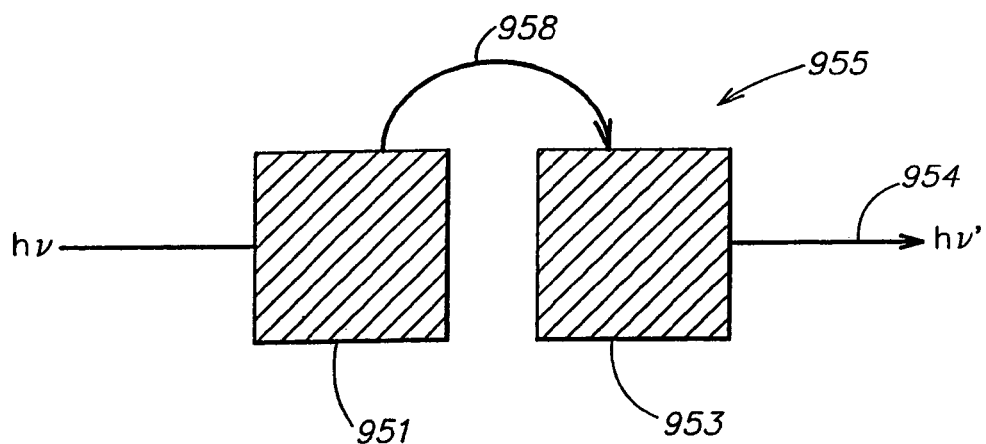
FIG. 11a(3)

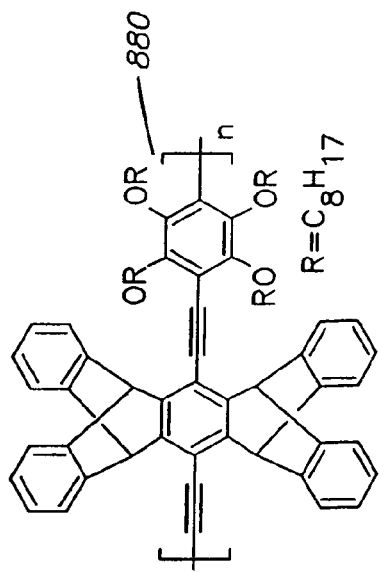
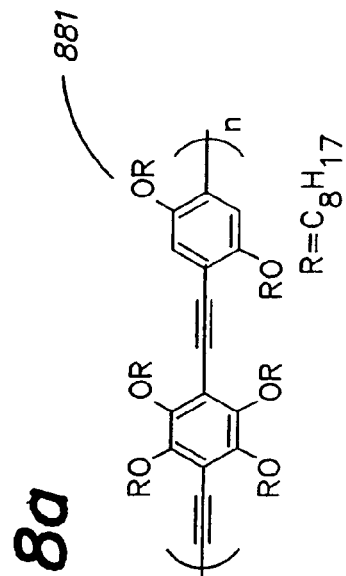
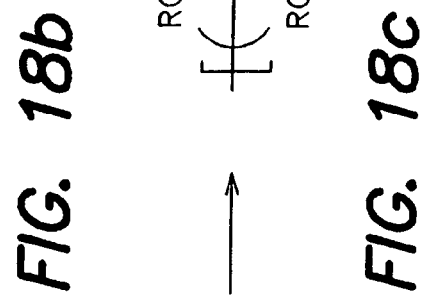
FIG. 18a  FIG. 18b  FIG. 18c
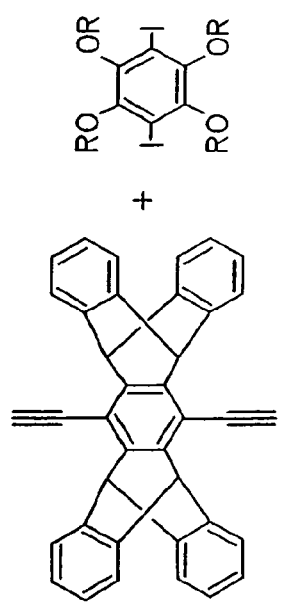
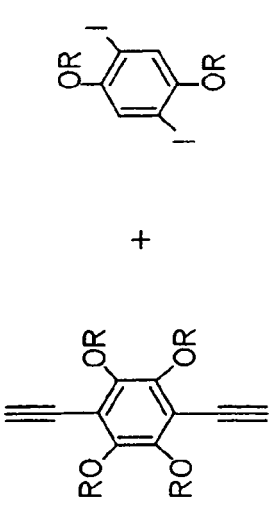
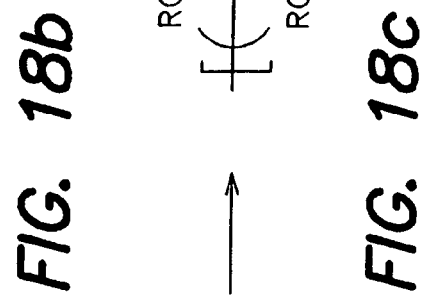

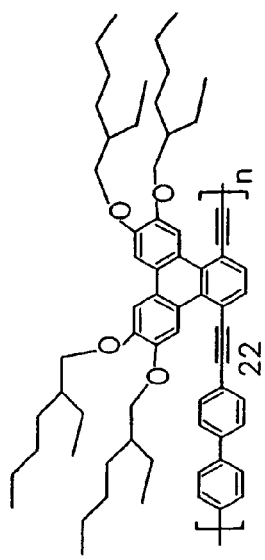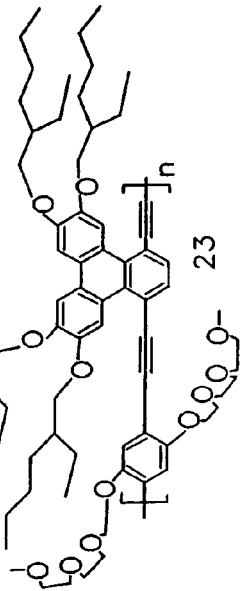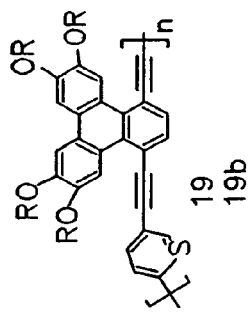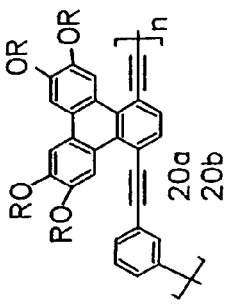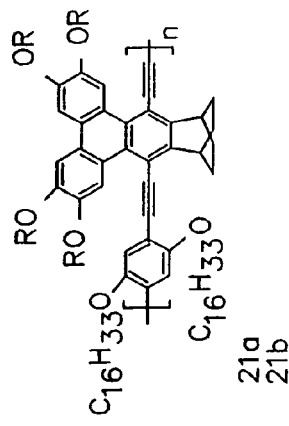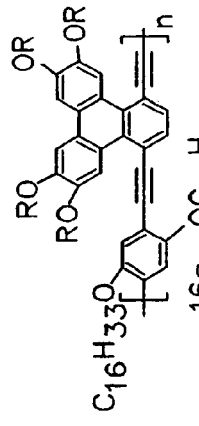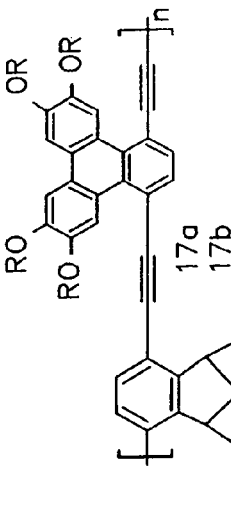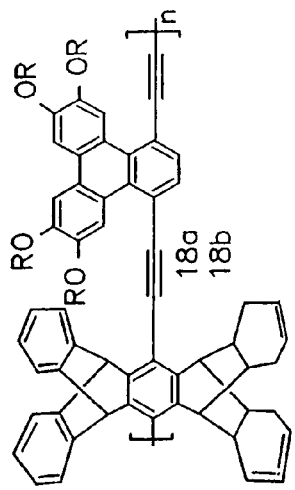
FIG. 32a  FIG. 32b  FIG. 32c
FIG. 32d  FIG. 32e  FIG. 32f
FIG. 32g  FIG. 32h

EMISSIVE POLYMERS AND DEVICES INCORPORATING THESE POLYMERS

RELATED APPLICATION

This application is a divisional of U.S. patent application Ser. No. 10/324,064, filed Dec.18, 2002, now U.S. Pat. No. 7,208,122 entitled "Emissive Polymers and Devices Incorporating These Polymers," by Timothy M. Swager et al., which application is a continuation of U.S. patent application Ser. No. 09/305,379, filed May 5, 1999, now abandoned entitled "Emissive Polymers and Devices Incorporating These Polymers," by Timothy M. Swager, et al., which application claims the benefit under Title 35 U.S.C. §119(e) of U.S. provisional application Ser. No. 60/084,247, filed May 5, 1998, entitled "Shape Persistent Polymers with High Fluorescence and Stability," by Timothy M. Swager et al., Each of these applications is incorporated herein by reference.

This invention was made with government support under Contract Number DABT63-97-C-0008 awarded by the Army and Grant Number N00014-97-1-0174 awarded by the Navy. The government has certain rights to this invention.

FIELD OF THE INVENTION

The present invention relates to a class of luminescent and conductive polymer compositions, and particularly solid films of these compositions exhibiting increased luminescent lifetimes, quantum yields and amplified emissions. The invention also relates to a sensor and a method for sensing an analyte through the luminescent and conductive properties of these polymers.

BACKGROUND OF THE INVENTION

There is a high demand for chemical sensor devices for detecting low concentration levels of analytes present in the liquid and gaseous phase. Specificity to particular analytes is also generally desired.

Chemical sensor devices often involve luminescent materials because luminescence lifetimes and intensities can be sensitive to the presence of external species or analytes. Fluorescent polymeric materials are particularly advantageous for sensor devices because the resulting fluorescence and other physical properties can be optimized and/or tailored for particular analytes through chemical structure changes of the polymer.

Charge conducting polymers are usually fluorescent polymers. Such polymers are capable of delocalizing charge throughout a substantial portion of the polymer by π-conjugation. The π-conjugated portion comprises a set of orbitals that can function as a valence band. The polymers can be doped with species that either donate or accept electron density, and an energy difference between the valence band and conduction band is referred to as a band gap. Moreover, other energy levels may be available in the band gap or in higher energy levels having antibonding character.

Because charge delocalization results in the formation of various high lying energy levels, a variety of excited state structures are available upon absorption of energy by the conducting polymer. The luminescence yields of these excited state structures depend highly on polymer structure. The luminescence can be quenched by the presence of species capable of absorbing the energy contained by the polymer, resulting in the polymer returning to a ground state. The species can be an external species or internally located within the polymer, such as a side-group. One example of such quenching by internal species is through a π-stacking mechanism. Atoms involved in the π-conjugation can be positioned on top of other groups having geometrically accessible π-orbitals, forming a pathway for energy transfer.

Luminescent polymers are disclosed in U.S. Pat. No. 5,414,069 which describes an electroluminescent polymer having a main chain and a plurality of side chains. The main chain contains methylene or oxide groups and the side chains contain the electroluminescent groups such that the electroluminescent groups are not conjugated with one another. One method of modulating electroluminescent properties is by varying the spacing between the electroluminescent groups.

U.S. Pat. No. 5,597,890 relates to π-conjugated polymers that form exciplexes with electron donor or acceptor components. The polymer has a main chain of unsaturated units such as carbon-carbon double and triple bonds and aromatic groups. The side chains include single ring aryl groups.

Thus there remains a need to design polymers having maximal luminescent lifetimes for use in sensory devices, in particular where the luminescent properties are sensitive to the presence of specific analytes.

SUMMARY OF THE INVENTION

The present invention relates to polymeric compositions capable of emitting radiation and exhibiting increased luminescent lifetimes and quantum yields. These compositions can be tailored to prevent π-stacking or interactions with acceptor species that can quench the luminescence. The polymers have sufficient rigidity through design of the polymer backbone and/or side groups which not only optimizes optical properties but imparts enhanced polymer stability. The invention also provides devices such as sensors which incorporate films of these polymeric compositions.

One aspect of the invention provides a sensor comprising a film including a polymer. The polymer includes a chromophore and the polymer is capable of emitting radiation with a quantum yield of at least about 0.05 times that of a quantum yield of the polymer in solution.

Another aspect of the present invention provides a method for amplifying an emission. The method comprises providing an article comprising a polymer having an energy migration pathway and a chromophore. The article is exposed to a source of energy to form an excitation energy. The excitation energy is allowed to travel through the migration pathway and to transfer to the chromophore, causing an emission that is greater than an emission resulting from a polymer free of an energy migration pathway.

Another aspect of the present invention provides a method for amplifying an emission. The method involves providing an article comprising a polymer having an energy migration pathway. The polymer has reduced π-stacking. The article is exposed to a source of energy from an excitation energy. The excitation energy is allowed to travel through the migration pathway to cause an emission that is greater than an emission resulting from a polymer free of an energy migration pathway.

Another aspect of the present invention provides a sensor. The sensor comprises an article having at least one layer including a polymeric composition and a chromophore. The article further comprises an activation site where the chromophore is capable of activation by an analyte at the activation site. The sensor also comprises an energy migration pathway within the polymeric composition where energy can be transferred from the pathway to the activation site.

Another aspect of the present invention provides a sensor comprising a polymer capable of emission. The emission is variable and sensitive to an electric field of a medium surrounding the sensor.

Another aspect of the present invention provides a sensor comprising a polymer capable of emission. The emission is variable and sensitive to a dielectric constant of a medium surrounding the sensor.

Another aspect of the present invention provides an amplification device. The device comprises a polymer having an energy migration pathway capable of transporting an excitation energy. The device further comprises a chromophore in electronic communication with the energy migration pathway where the chromophore is capable of emitting an enhanced radiation.

Another aspect of the invention provides a polymeric composition. The composition comprises a conjugated π-backbone, the π-backbone comprising a plane of atoms. A first group and a second group is attached to the π-backbone, the first group having a first fixed height above the plane and the second group having a second fixed height below the plane. A sum of the first and second heights is at least about 4.5 Å.

Another aspect of the invention provides a sensor which includes a polymeric article comprising the structure:

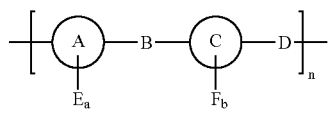

A and C are aromatic groups and B and D are selected from the group consisting of a carbon-carbon double bond and a carbon-carbon triple bond. Any hydrogen on aromatic group A and C can be replaced by E and F respectively, a and b being integers which can be the same or different and a=0-4, b=0-4 such that when a=0, b is nonzero and when b=0, a is nonzero, and at least one of E and F includes a bicyclic ring system having aromatic or non-aromatic groups optionally interrupted by O, S, $NR^1$ and $C(R^1)_2$ wherein $R^1$ is selected from the group consisting of hydrogen, $C_1$-$C_{20}$ alkyl, $C_1$-$C_{20}$ alkoxy and aryl. The value n is less than about 10,000. The sensor further comprises a source of energy applicable to the polymeric composition to cause emission of radiation and a device for detecting the emission.

Another aspect of the invention provides a method for detecting the presence of an analyte. The method provides a polymeric article comprising the structure:

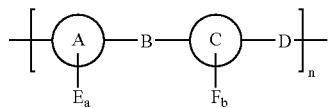

A and C are aromatic groups and B and D are selected from the group consisting of a carbon-carbon double bond and a carbon-carbon triple bond. Any hydrogen on aromatic group A and C can be replaced by E and F respectively, a and b being integers which can be the same or different and a=0-4, b=0-4 such that when a=0, b is nonzero and when b=0, a is nonzero, and at least one of E and F includes a bicyclic ring system having aromatic or non-aromatic groups optionally interrupted by O, S, $NR^1$ and $C(R^1)_2$ wherein $R^1$ is selected from the group consisting of hydrogen, $C_1$-$C_{20}$ alkyl, $C_1$-$C_{20}$ alkoxy and aryl. The value n is less than about 10,000. The method further includes exposing the polymeric composition to a source of energy to cause a first emission of radiation. The polymeric composition is then exposed to a medium suspected of containing an analyte, causing a second emission of radiation. The method involves detecting a difference between the first emission and the second emission.

Another aspect of the invention provides a field-effect transistor including an insulating medium having a first side and an opposing second side and a polymeric article positioned adjacent the first side of the insulating medium. A first electrode is electrically connected to a first portion of the polymeric article and a second electrode is electrically connected to a second portion of the polymeric article. Each electrode is positioned on the first side of the insulating medium, and the first electrode is further connected to the second electrode by an electrical circuit external of the polymeric structure. A gate electrode is positioned on the second side of the insulating medium in a region directly opposite the polymeric article where the gate electrode is also connected to a voltage source. A source of electromagnetic radiation is positioned to apply the electromagnetic radiation to the article. At least one species is associated with the article. The at least one species, upon exposing the polymeric article to the electromagnetic radiation, is a component of an excited state structure.

Other advantages, novel features, and objects of the invention will become apparent from the following detailed description of the invention when considered in conjunction with the accompanying drawings, which are schematic and which are not intended to be drawn to scale. In the figures, each identical or nearly identical component that is illustrated in various figures is represented by a single numeral. For purposes of clarity, not every component is labeled in every figure, nor is every component of each embodiment of the invention shown where illustration is not necessary to allow those of ordinary skill in the art to understand the invention.

BRIEF DESCRIPTION OF THE DRAWINGS

FIG. 8 shows a schematic synthesis of (a) the polymerization of poly(phenyleneethynylene) on phenyliodide functionalized resin; (b) ethyl ester end functionalized poly(phenyleneethynylene);

FIG. 9 shows a schematic synthesis of (a) polymer A and polymer B; (b) polymer C;

FIG. 10 shows a schematic synthesis of (a) polymer synthesis with monomer DD; (b) monomer 1,4-Dinaphthyl-2,5-diacetylidebenzene (DD);

FIG. 11A schematically shows amplified emission of two polymers in series;

FIG. 32 shows examples of triphenylene-based polymer structures; and

DETAILED DESCRIPTION

Figure 1:
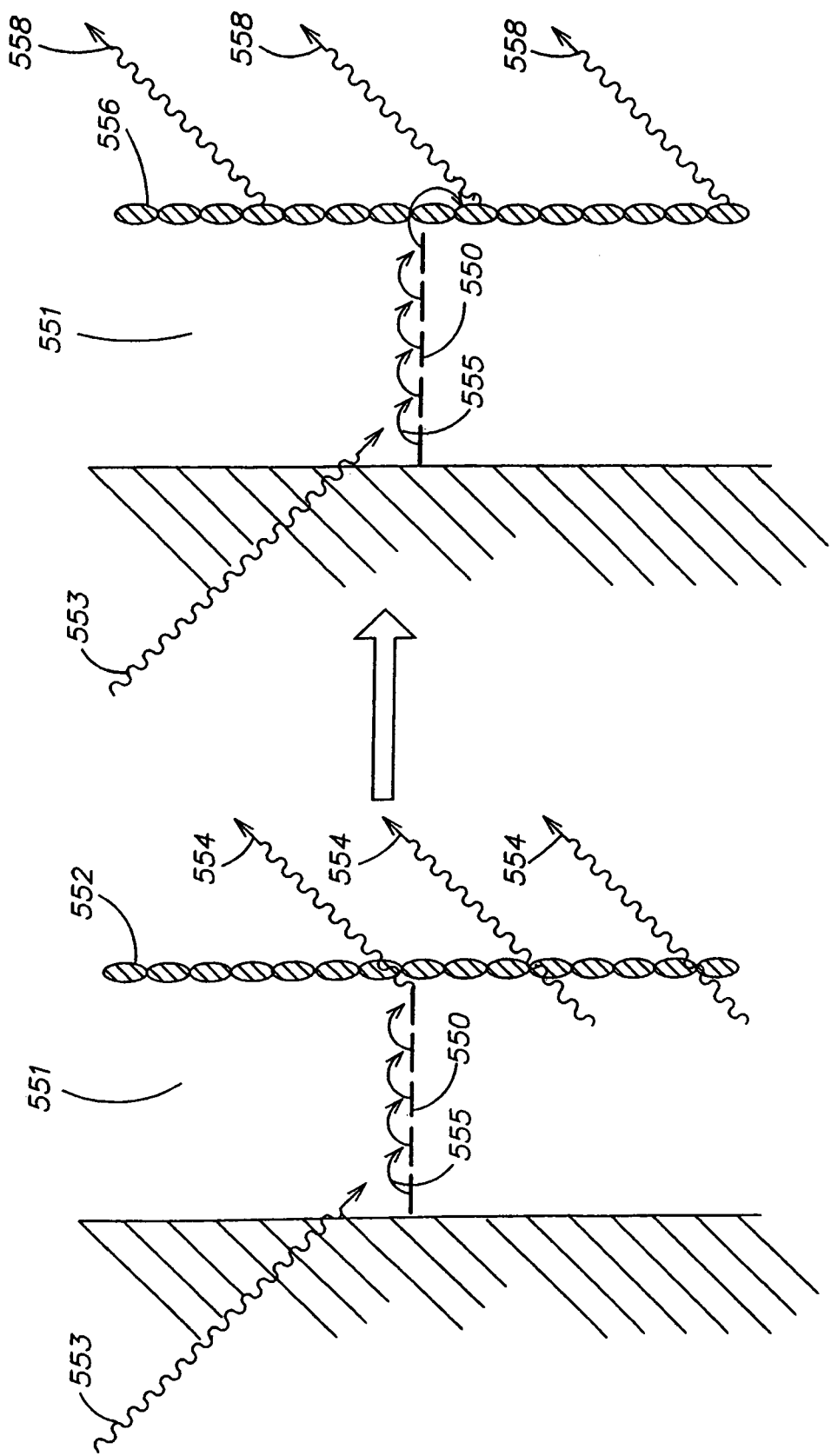
FIG. 1 shows a schematic of a film comprising a polymer having a chromophore positioned on a surface of the polymer.

The present invention relates to polymer films exhibiting enhanced optical properties such as luminescent lifetimes, amplified emissions, enhanced stabilities and devices such as sensors which incorporate these polymer films.

One aspect of the invention provides a sensor comprising a film. A "sensor" refers to any device or article capable of detecting an analyte. In one embodiment, the film comprises a polymer where the polymer includes a chromophore. Polymers are extended molecular structures comprising a backbone which optionally contain pendant side groups, where "backbone" refers to the longest continuous bond pathway of the polymer. A "chromophore" refers to a species that can either absorb or emit electromagnetic radiation. In a preferred embodiment, the chromophore is capable of absorbing or emitting radiation in the UV-visible range, i.e. absorbed or emitted energy involving excited electronic states. In one embodiment, the chromophore is a conjugated group. A "conjugated group" refers to an interconnected chain of at least three atoms, each atom participating in delocalized $\pi$-bonding.

A polymer including a chromophore can absorb a quantum of electromagnetic radiation to cause the polymer to achieve an excited state structure. In one embodiment, the polymer is an emissive polymer capable of emitting radiation. Radiation can be emitted from a chromophore of the polymer. In one embodiment, the emitted radiation is luminescence, in which "luminescence" is defined as an emission of ultraviolet or visible radiation. Specific types of luminescence include "fluorescence" in which a time interval between absorption and emission of visible radiation ranges from $10^{-12}$ to $10^{-7}$ s. "Chemiluminescence" refers to emission of radiation due to a chemical reaction, whereas "electrochemiluminescence" refers to emission of radiation due to electrochemical reactions. If the chromophore is a conjugated group, the extent of delocalized bonding allows the existence of a number of accessible electronic excited states. If the conjugation is so extensive so as to produce a near continuum of excited states, electronic excitations can involve a valence band, the highest fully occupied band, and a conduction band.

Typically, fluorescence is "quenched" when a chromophore in an excited state is exposed to an "acceptor" species that can absorb energy from the excited state chromophore. The excited state chromophore returns to a ground state due to nonradiative processes (i.e. without emitting radiation), resulting in a reduced quantum yield. A "quantum yield" refers to a number of photons emitted per adsorbed photon. Thus, the excited state chromophore can function as a "donor" species in that it transfers energy to the acceptor species. The acceptor species can be an external molecule such as another polymer or an internal species such as another portion of the same polymer.

In particular, when a polymer includes conjugated portions, the polymer can undergo a phenomena known as "$\pi$-stacking," which involves cofacial interactions between $\pi$-orbitals of the conjugated portions. If the polymer includes a conjugated chromophore, a $\pi$-stacking arrangement can facilitate energy transfer between donor and acceptor species and increase the likelihood of quenching. The capability for $\pi$-stacking is considerably enhanced when the polymer is in the solid state, i.e. not in solution.

It is an advantageous feature of the present invention to provide a polymer including a chromophore, where the polymer has a molecular structure that reduces $\pi$-stacking interactions, resulting in increased quantum yields and/or luminescence lifetimes. It is particularly advantageous that these enhanced properties can be achieved when the polymer is provided as a solid state material, e.g. a film. In one embodiment, the film comprising a polymer including a chromophore has a quantum yield of at least about 0.05 times the quantum yield of the polymer in solution, more preferably at least about 0.1 times the quantum yield of the polymer in solution, more preferably at least about 0.15 times the quantum yield of the polymer in solution, more preferably at least about 0.2 times the quantum yield of the polymer in solution, more preferably at least about 0.25 times the quantum yield of the polymer in solution, more preferably at least about 0.3 times the quantum yield of the polymer in solution, more preferably at least about 0.4 times the quantum yield of the polymer in solution, and more preferably still about 0.5 times the quantum yield of the polymer in solution.

In one embodiment, the polymer backbone includes at least one chromophore. Preferably, the backbone includes a plurality of chromophores optionally interrupted by conjugated or non-conjugated groups. In one embodiment, the polymer backbone includes a plurality of chromophores interrupted by non-conjugated groups. Non-conjugated groups include saturated units such as a chain of alkyl groups optionally interrupted by heteroatoms. In one embodiment, the polymer backbone includes a chromophore attached as a pendant group. The backbone can be either conjugated or non-conjugated.

In one embodiment, at least a portion of the polymer is conjugated, i.e. the polymer has at least one conjugated portion. By this arrangement, electron density or electronic charge can be conducted along the portion where the electronic charge is referred to as being "delocalized." Each p-orbital participating in conjugation can have sufficient overlap with adjacent conjugated p-orbitals. In one embodiment, the conjugated portion is at least about 30 Å in length. In another embodiment, the entire backbone is conjugated and the polymer is referred to as a "conjugated polymer." Polymers having a conjugated π-backbone capable of conducting electronic charge are typically referred to as "conducting polymers." In the present invention the conducting polymers can either comprise chromophore monomeric units, or chromophores interspersed between other conjugated groups. Typically, atoms directly participating in the conjugation form a plane, the plane arising from a preferred arrangement of the p-orbitals to maximize p-orbital overlap, thus maximizing conjugation and electronic conduction. An example of a conjugated π-backbone defining essentially a plane of atoms are the carbon atoms of a polyacetylene chain.

In one embodiment, the polymer is selected from the group consisting of polyarylenes, polyarylene vinylenes, polyarylene ethynylenes and ladder polymers, i.e. polymers having a backbone that can only be severed by breaking two bonds. Examples of such polymers include polythiophene, polypyrrole, polyacetylene, polyphenylene and substituted derivatives thereof. Examples of ladder polymers are:

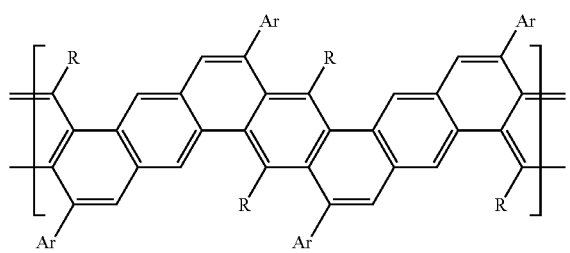

-continued

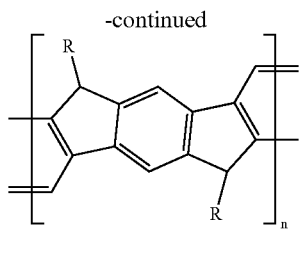

(R = C$_{12}$H$_{25}$)
(Ar = 4-ROPh)

In these examples, monomeric units can combine to form a chromophore. For example, in polythiophene, the chromophore comprises about thiophene groups.

By reducing the extent of luminescence quenching, luminescence lifetimes are increased and thus excitation energy can travel along a longer pathway in the polymer. The pathway is referred to as an "energy migration pathway" which can efficiently transport excitation energy, preferably electronic excitation energy. In one embodiment, the pathway has a length of at least about 30 Å. In one embodiment, the pathway comprises a series of electronic energy states accessible to the excitation energy.

A chromophore can have different functions in a polymer. For example, physical characteristics of a chromophore can be affected by detection of an analyte. This type of chromophore is referred to as a "reporter chromophore" which reports the detection of an analyte. A reporter chromophore can be bonded to the polymer or can be an external molecule. A chromophore in the polymer can also function to transport excitation energy along the polymer and can be referred to as a "transporter chromophore."

Accompanying this advantageous feature of longer pathways and lifetimes is enhanced amplification of emission. It has been established that amplification in a polymer is related to a distance over which excitation energy can travel. Thus, another aspect of the present invention provides a method for amplifying an emission. The method involves providing an article having a polymeric composition having an energy migration pathway and a chromophore. In one embodiment, the chromophore can be a reporter chromophore. The energy migration pathway can be conjugated. Exposing the article to a source of energy forms an excitation energy which is allowed to travel through the migration pathway. In one embodiment, migration is enhanced if it occurs in a direction where a HOMO-LUMO gap continually decreases. Energy can transfer from the pathway to a chromophore to cause an emission of radiation. In one embodiment, the reporter chromophore can be bonded to the polymer as a portion of the backbone or as a pendant side group. In another embodiment, the reporter chromophore is a molecule external to the polymer.

In one embodiment, the emission from a reporter chromophore is greater than an emission from a reporter chromophore in a polymer that is free of an energy migration pathway. Polymers that are "free of an energy migration pathway" typically refer to polymers that are incapable of efficiently transporting excitation energies, e.g. polymers having a completely carbon-based saturated backbone lacking pendant chromophores.

Energy transfer from the pathway to the reporter chromophore is facilitated if the chromophore has a HOMO-LUMO gap less than at least a portion of the pathway. To enhance amplification, preferably the reporter chromophore has a HOMO-LUMO gap less than a substantial portion of the pathway, to maximize a distance that the excitation energy travels before transfer to the reporter chromophore.

An example of a film comprising polymer of the present invention is provided in FIG. 1 which shows polymer 551 having an energy migration pathway 550. Exposing the polymer to a source of energy 553 results in an excitation energy that can travel along an energy migration pathway 550. To "travel along an energy migration pathway" refers to a process by which excitation energy can transfer between accessible energy states. Arrows 555 indicate a direction of travel, and typically this direction is dictated by a continual decrease of a HOMO-LUMO gap of the energy states in the migration pathway. Emission from the polymer, indicated by arrows 554, can result. Polymer 551 has a chromophore that allows this emission of radiation.

Another aspect of the present invention provides an amplification device. The device comprises a polymer having an energy migration pathway capable of transporting an excitation energy. As described above, the polymer can be exposed to a source of energy which is absorbed by the polymer as an excitation energy. The excitation energy can travel through the migration pathway and transfer to a chromophore in electronic communication with the energy migration pathway, whereby an enhanced radiation is emitted from the chromophore. An excitation energy can transfer from the migration pathway to the chromophore if the chromophore is in electronic communication with the pathway, i.e. the chromophore has accessible energy states by which excitation energy traveling through the migration pathway can transfer. By this device, the emission of any number of polymers can be enhanced.

Another aspect of the present invention provides reduced π-stacking interactions through the incorporation of rigid groups on the polymer. "Rigid groups" refers to groups that do not easily rotate about a bond axis, preferably a bond that binds the rigid group to the polymer. In one embodiment, the rigid group rotates no more than about 180°, preferably no more than about 120° and more preferably no more than about 60°. Certain types of rigid groups can provide a polymer with a backbone separated from an adjacent backbone at a distance of at least about 4.5 Å and more preferably at least about 5.0 Å. In one embodiment, the rigid groups are incorporated as pendant groups.

Figure 23:
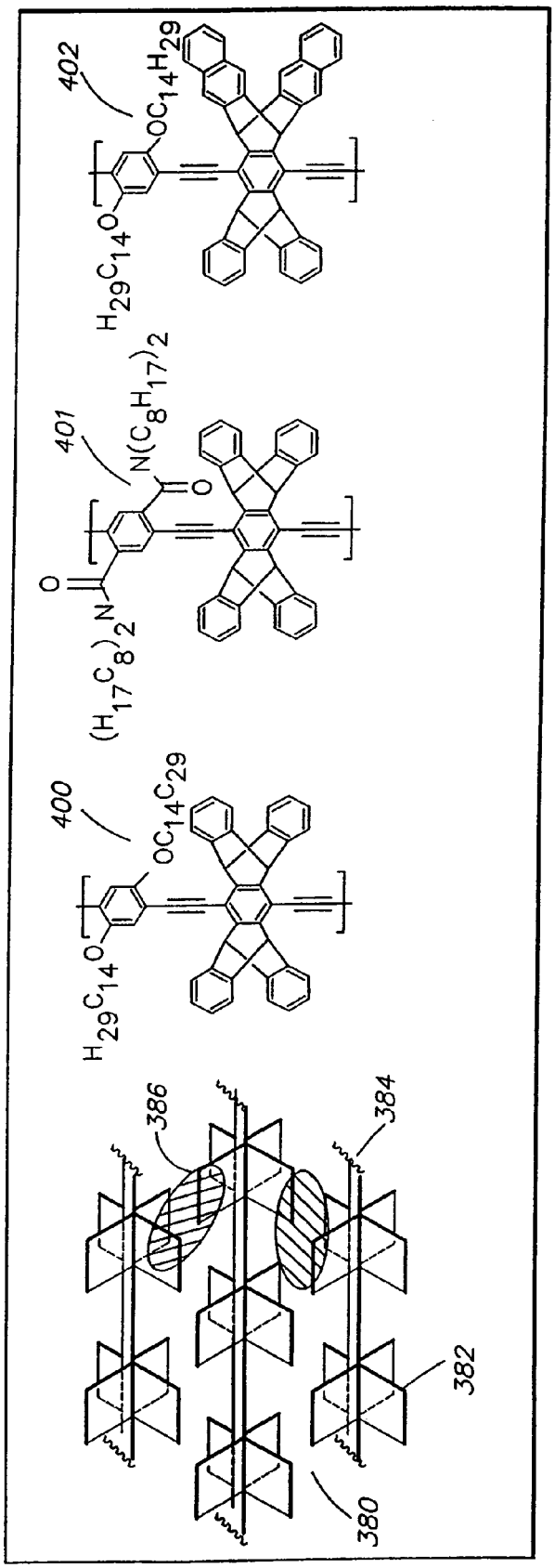
FIG. 23 shows a schematic of a polymer having rigid groups that reduce $\pi$-stacking interactions between polymer backbones.

The effect of rigid groups can be schematically illustrated in FIG. 23. Rigid group 382 can be appended onto a polymer backbone 384. The rigid groups prevent substantial interaction between polymer backbones 384 such that cavities 380 are produced. In addition to preventing or reducing the amount of π-stacking, cavities 380 can allow an area for the entry of analytes 386.

In one embodiment, a polymeric composition is provided having a conjugated π-backbone, the π-backbone comprising essentially a plane of atoms. A first group and a second group are attached to the π-backbone of the polymeric composition. Both the first and second groups have at least some atoms that are not planar with the plane of atoms such that the atoms can be positioned either below or above the conjugated plane of atoms. It is a feature of the invention that these heights are fixed, the term "fixed height" defined as a height of an atom that is not planar with the plane of atoms where the atom is free of substantial rotational motion, as described above.

Figure 2:
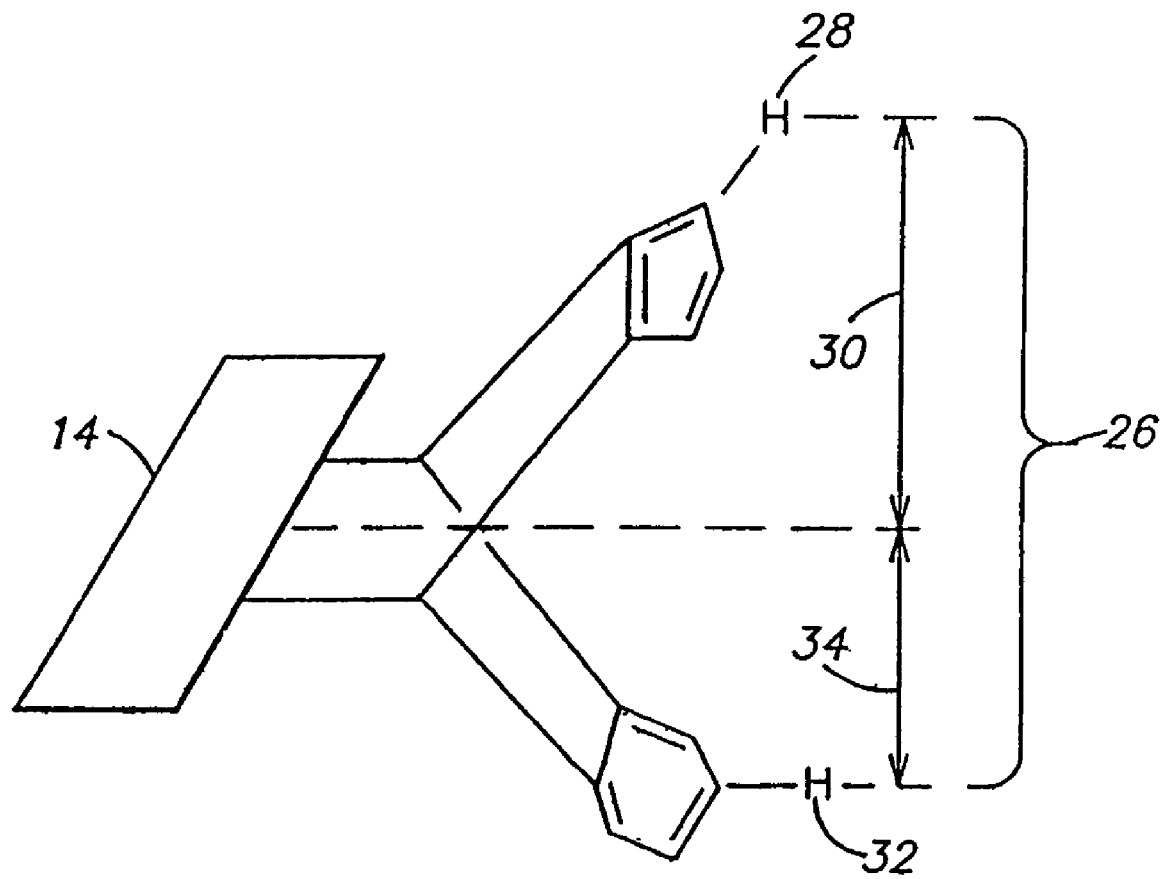
FIG. 2 shows a schematic of a rigid side group having fixed heights above and below a π-backbone plane.
Figure 3A:
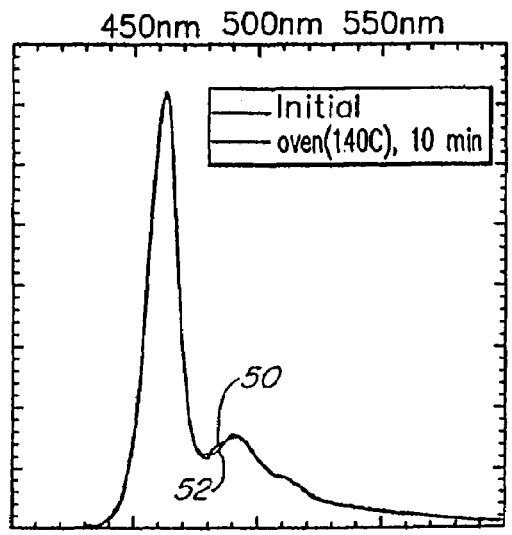
FIG. 3 shows fluorescence spectra of (a) polymer A before and after heating polymer A to 140° C. for 10 minutes; (b) polymer A before and after washing polymer A to methanol for min; (c) polymer X before and after heating polymer X to 140° C. for five minutes; (d) polymer X before and after washing polymer X with methanol for 5 min.
Figure 3B:
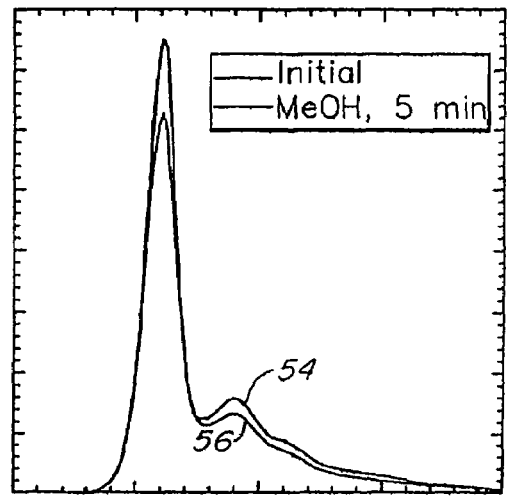
Figure 3C:
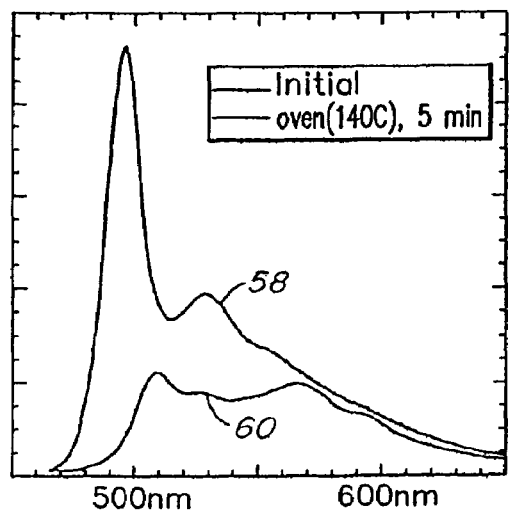
Figure 3D:
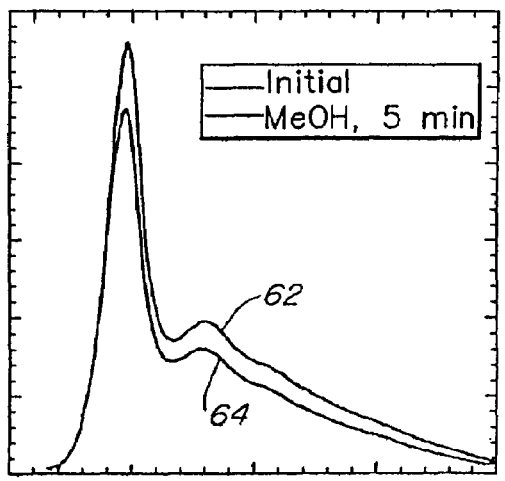

FIG. 2 shows an example of a "fixed height" where side group 26 is bonded to the backbone in a manner that restricts rotational motion. In this example, hydrogen atoms 26 and 28 define a fixed height relative to plane 14. The fixed height of sidegroup 26 is defined by hydrogen atom 28, having a fixed height above the plane 30 and hydrogen 32 having a fixed height below the plane 34. In one embodiment, a sum of the fixed heights is at least about 4.5 Å and more preferably at least about 5.0 Å.

It is another feature of the invention that the polymeric composition is rigid with respect to relative orientation between polymers. Typically, polymers have a nonordered structure. Upon polymerization or solidification, the polymer can orient in a random arrangement. This arrangement can change over time, or upon exposure to heat or a solvent that does not dissolve the polymer. In one embodiment, the compositions of the present invention are rigid to the extent that the polymer arrangement does not substantially change over time, upon exposure to solvent or upon heating to a temperature of no more than 150° C. That is, the rigidity of the side group defining a fixed height does not change and the height is not affected. In one embodiment, the exposure to solvent or heating step occurs over a period of time of about 5 min., preferably over a period of time of about 10 min., more preferably about 15 min., more preferably about 30 min., and more preferably still about 1 h. In one embodiment, the composition is characterized by a first optical spectrum having at least one maximum or maxima. The composition is then exposed to a solvent or heated to a temperature of less than about 140° C. and a second optical spectrum is obtained. A maximum or maxima in the first spectrum differ by no more than about 15 nm from a corresponding maximum or maxima in the second spectrum, preferably the maxima differ by no more than about 10 nm and more preferably the maxima differ by no more than about 5 nm. In another embodiment, maxima in the second spectrum have an intensity change of less than about 10% relative to the maxima in the first spectrum, and preferably the intensity change is less than about 15% relative to the maxima in the first spectrum.

An advantage of the present invention is illustrated in FIG. 3. FIG. 3 compares various spectra of polymers A (shown below) and polymer X (which does not have sufficient rigidity, shown below) in the solid state. In FIG. 3(a), an initial fluorescence spectrum 50 of polymer A is obtained. Polymer A is then heated to 140° C. for 10 minutes and spectrum 52 is obtained. The fluorescence maxima values and fluorescence intensities are nearly identical, providing evidence that any reorganization between polymer chains or chemical reorganization within each chain is insubstantial. In FIG. 3(b), a similar comparison is made between an initial spectrum 54 and spectrum 56 for a polymer A, spectrum 56 being obtained after exposing the polymer to a solvent such as methanol for 5 min. In this example, the exposing involves washing the polymer with methanol. The absorption maxima of spectrum 54 have the same frequencies as the corresponding maxima in 56, and the intensities in 56 decrease by only about 10%, again showing the reorganizational stability to solvent exposure. In contrast, a comparison of an initial spectrum 58 of planar model polymer X is shown in FIG. 3(c) which shows a substantial differences from fluorescence spectrum 60, taken after heating the polymer to 140° C. for only five minutes. Not only do the fluorescence maxima occur at different frequencies but the intensities decrease significantly. In FIG. 3(d), the intensities of fluorescence spectrum 62 of polymer X decrease by 15% in spectrum 64 which was obtained after washing polymer X with methanol for about 5 min.

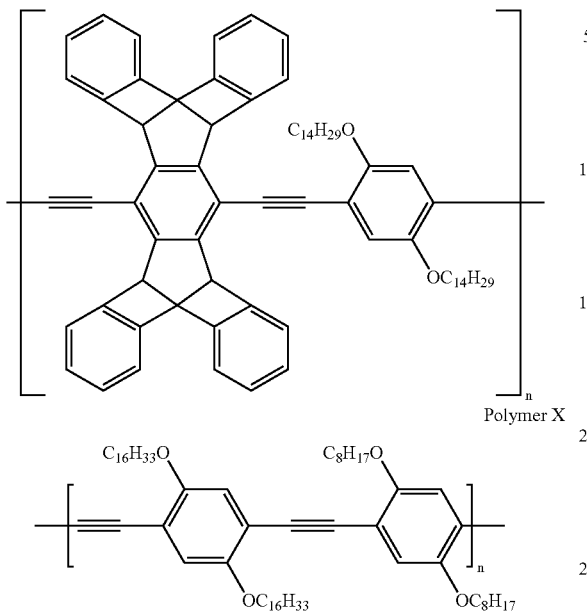

Polymer A

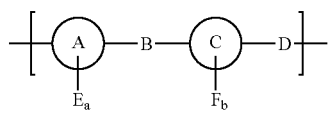

Polymer X

Figure 4A:
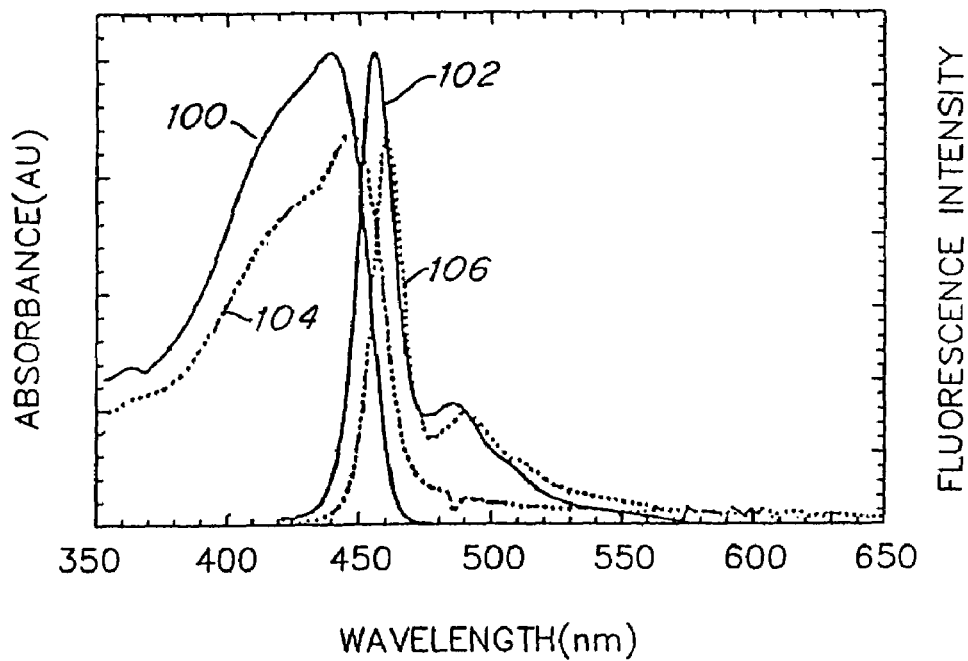
FIG. 4 shows solid state and solution absorption and emission spectra for (a) polymer A; (b) polymer X.
Figure 4B:
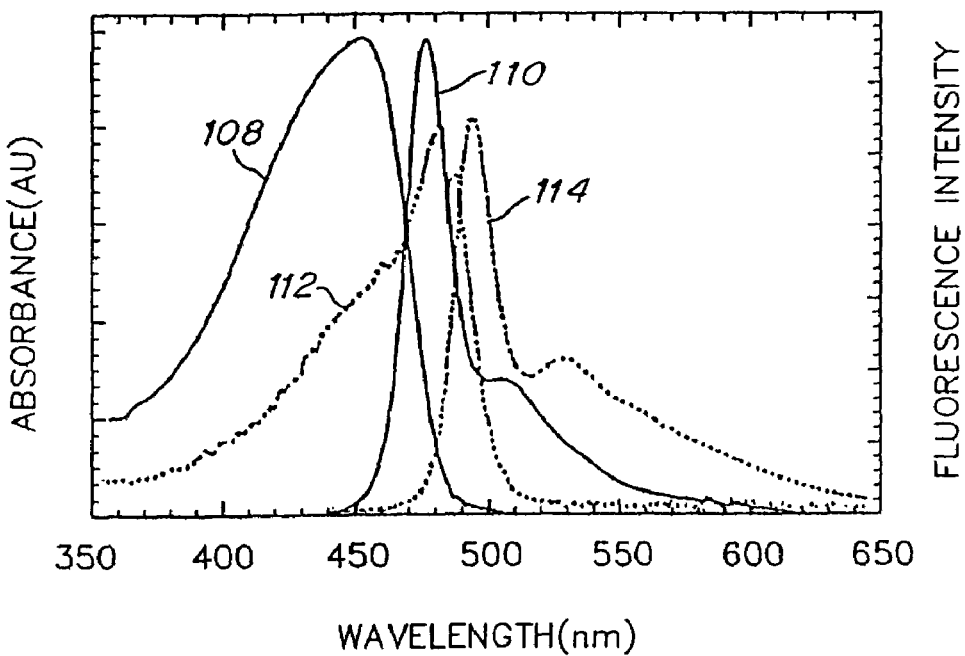

FIG. 4 shows a comparison of solution and solid state absorption and emission spectra for a polymer allowing π-stacking interactions that can quench luminescence, rendering the polymer ineffective for the uses of the invention, versus a polymer of the invention having sufficient rigidity to prevent π-stacking interactions. In FIG. 4(a) absorption and emission spectra 100 and 102 respectively, are obtained for polymer A in solution. Polymer A has a rigid structure with respect to chain reorganization, such that absorption and emission spectra 104 and 106 respectively, obtained for polymer A as a film, show little decrease in intensity. In contrast, FIG. 4(b) shows solution absorption and emission spectra 108 and 110 respectively for polymer X which does not have a rigid structure in accordance with the features of the invention. The film absorption and emission spectra, 112 and 114 respectively, show significant wavelength shifts and a substantial decrease in intensity (the intensity of spectrum 114 has actually been normalized to an increased intensity to better illustrate the spectral characteristics and actually has a smaller intensity than shown in FIG. 4(b)).

Another aspect of the invention provides a polymeric composition comprising the structure:

A and C are aromatic groups. Specifically, an aromatic group is a cyclic structure having a minimum of three atoms with a cyclic, conjugated π-system of p-orbitals, the p-orbitals being occupied with 4n+2 electrons, n being a positive integer. B and D are selected from the group consisting of a carbon-carbon double bond and a carbon-carbon triple bond. E and F are attached to aromatic groups A and C respectively and a and b are integers which can be the same or different, a=0-4 and b=0-4 such that when a=0, b is nonzero and when b=0, a is nonzero. At least one of E and F includes a bicyclic ring system having aromatic or non-aromatic groups optionally interrupted by heteroatoms or heteroatom groups such as O, S, N, $NR^1$, $CR^1$ and $C(R^1)_2$ wherein $R^1$ can be selected from the group consisting of hydrogen, $C_1$-$C_{20}$ alkyl, $C_1$-$C_{20}$ alkoxy and aryl. Preferably n is less than about 10,000. In one embodiment, at least one of E and F comprise the first and second groups having first and second fixed heights above the π-backbone plane. The preferred features of the composition allow the polymer to have extensive π-conjugation throughout the polymer. In a preferred embodiment, the polymer is a conducting polymer.

In one embodiment, the polymeric composition has a structure where $E_a$ is shown attached to the π-backbone:

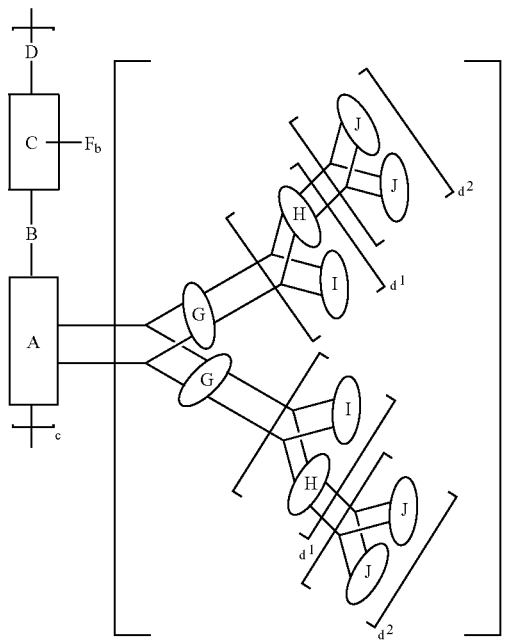

G, H, I, and J are aromatic groups, d=1, 2, and $d^1$=0, 1, such that when $d^1$=0, $d^2$=0 and when $d^1$=1, $d^2$=0, 1. Preferably, c is less than about 10,000.

In a preferred embodiment, G and H may be the same or different, and each can be selected from the aromatic group consisting of:

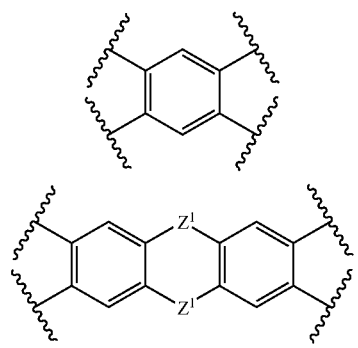

-continued

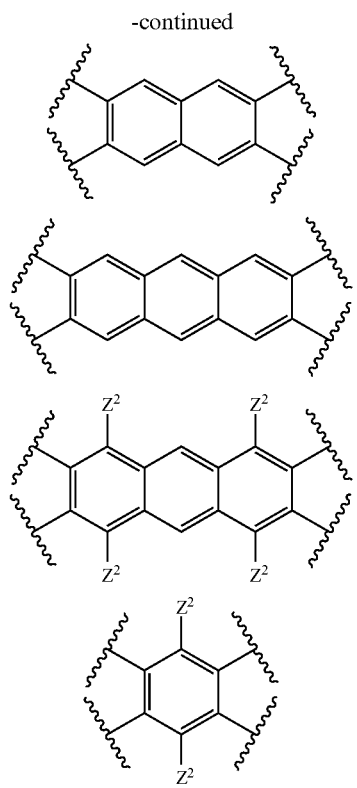

I and J may be the same or different and each can be selected from the group consisting of:

-continued

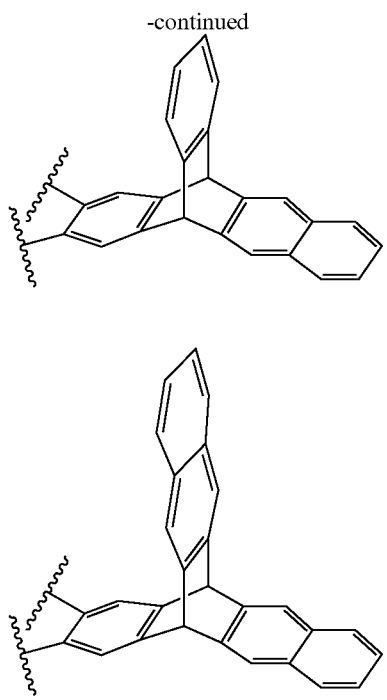

Any hydrogen in G, H, I and J can be substituted by $R^2$ where $R^2$ can be selected from the group consisting of $C_1$-$C_{20}$ alkyl, aryl, $C_1$-$C_{20}$ alkoxy, phenoxy, $C_1$-$C_{20}$ thioalkyl, thioaryl, $C(O)OR^3$, $N(R^3)(R^4)$, $C(O)N(R^3)(R^4)$, F, Cl, Br, $NO_2$, CN, acyl, carboxylate and hydroxy. $R^3$ and $R^4$ can be the same or different and each can be selected from the group consisting of hydrogen, $C_1$-$C_{20}$ alkyl, and aryl. $Z^1$ can be selected from the group consisting of O, S and $NR^8$ where $R^8$ can be selected from the group consisting of hydrogen, $C_1$-$C_{20}$ alkyl, and aryl. $Z^2$ can be selected from the group consisting of F, Cl, $OR^3$, $SR^3$, $NR^3R^4$ and $SiR^8R^3R^4$.

In one embodiment, A is selected from the group consisting of:

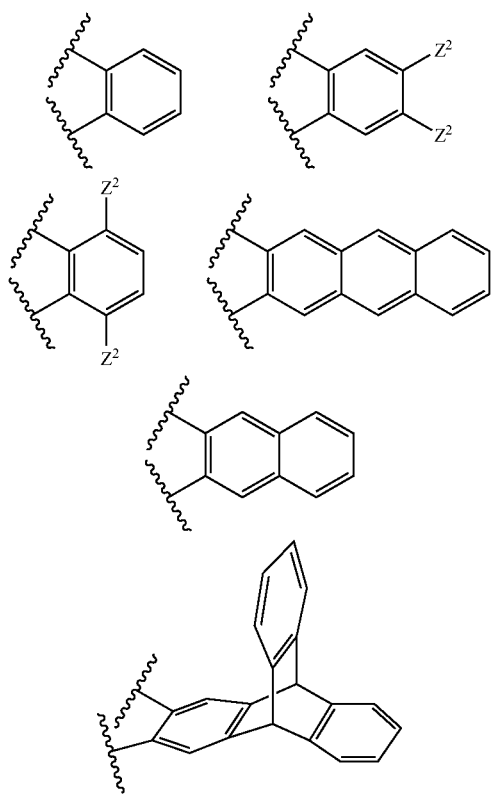

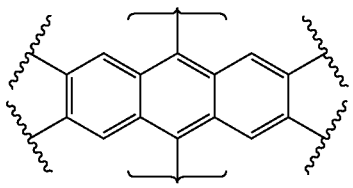

-continued

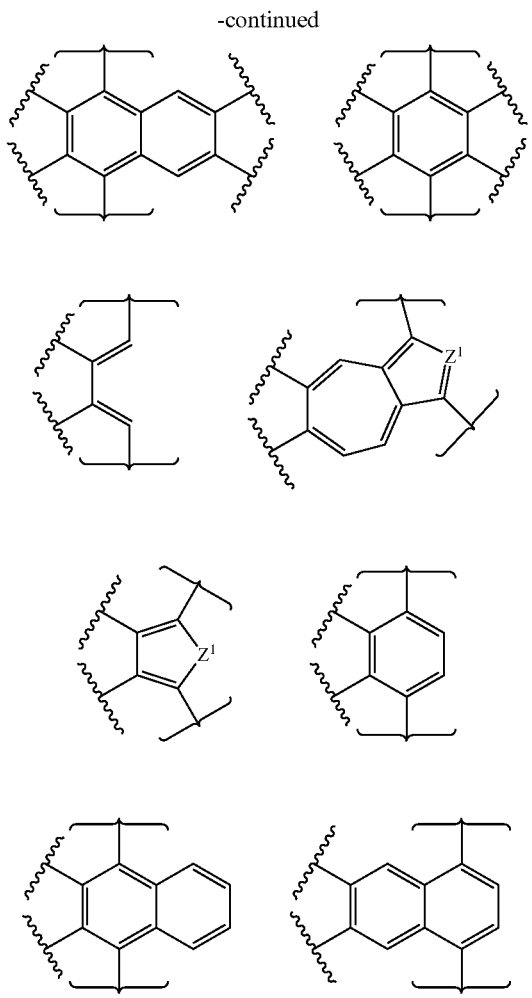

Any hydrogen in A can be substituted by $R^5$ where $R^5$ can be selected from the group consisting of $C_1$-$C_{20}$ alkyl, aryl, $C_1$-$C_{20}$ alkoxy, phenoxy, $C_1$-$C_{20}$ thioalkyl, thioaryl, C(O)OR$^6$, N($^6$)(R$^7$), C(O)N(R$^6$)(R$^7$), F, Cl, Br, NO$_2$, CN, acyl, carboxylate, hydroxy. $R^6$ and $R^7$ can be the same or different and each can be selected from the group consisting of hydrogen, $C_1$-$C_{20}$ alkyl, and aryl. $Z^1$ can be selected from the group consisting of O, S and NR$^8$ where $R^8$ can be selected from the group consisting of hydrogen, $C_1$-$C_{20}$ alkyl, and aryl. Preferably, A is selected from the group consisting of:

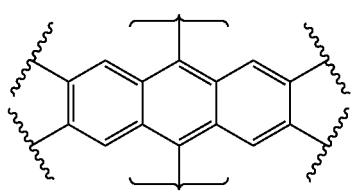

-continued

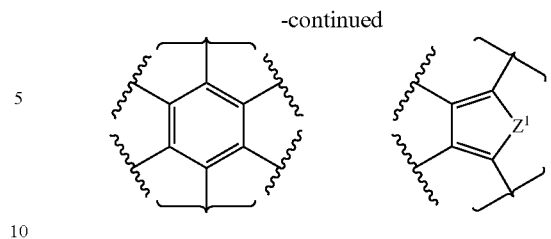

In one embodiment, B and D can be the same or different and each can be selected from the group consisting of:

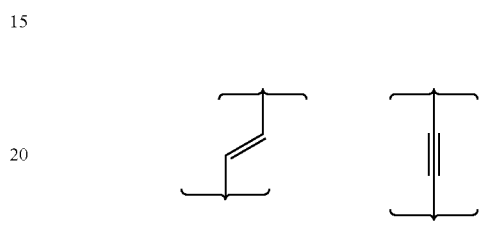

Any hydrogen in B and D can be substituted by $R^9$ where $R^9$ can be selected from the group consisting of $C_1$-$C_{20}$ alkyl, aryl, $C_1$-$C_{20}$ alkoxy, phenoxy, $C_1$-$C_{20}$ thioalkyl, thioaryl, C(O)OR$^{10}$N(R$^{10}$)(R$^{11}$), C(O)N(R$^{10}$)(R$^{11}$), F, Cl, Br, NO$_2$, CN, acyl, carboxylate, hydroxy. $R^{10}$ and $R^{11}$ can be the same or different and each can be selected from the group consisting of hydrogen, $C_1$-$C_{20}$ alkyl, and aryl. Preferably, B and D are:

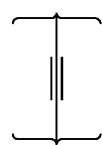

In one embodiment, C is selected from the aromatic group consisting of:

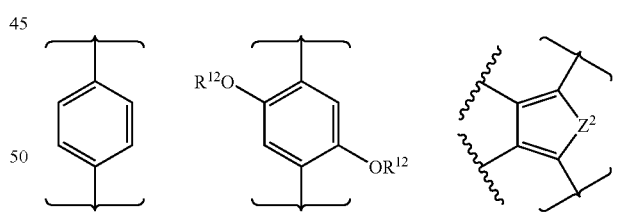

$R^{12}$ can be selected from the group consisting of hydrogen, $C_1$-$C_{20}$ alkyl and aryl. Any hydrogen in C can be substituted by R$^{13}$ where R$^{13}$ can be selected from the group consisting of $C_1$-$C_{20}$ alkyl, aryl, $C_1$-$C_{20}$ alkoxy, phenoxy, $C_1$-$C_{20}$ thioalkyl, thioaryl, C(O)OR$^{14}$, N(R$^{14}$)(R$^{15}$), C(O)N(R$^{14}$)(R$^{15}$), F, Cl, Br, NO$_2$, CN, acyl, carboxylate, hydroxy. $R^{14}$ and $R^{15}$ can be the same or different and each can be selected from the group consisting of hydrogen, $C_1$-$C_{20}$ alkyl, and aryl. $Z^2$ can be selected from the group consisting of O, S and NR$^{16}$ where $R^{16}$ can be selected from the group consisting of hydrogen, $C_1$-$C_{20}$ alkyl, and aryl.

Examples of particularly preferred polymeric compositions having the structural features in accordance with the invention include:

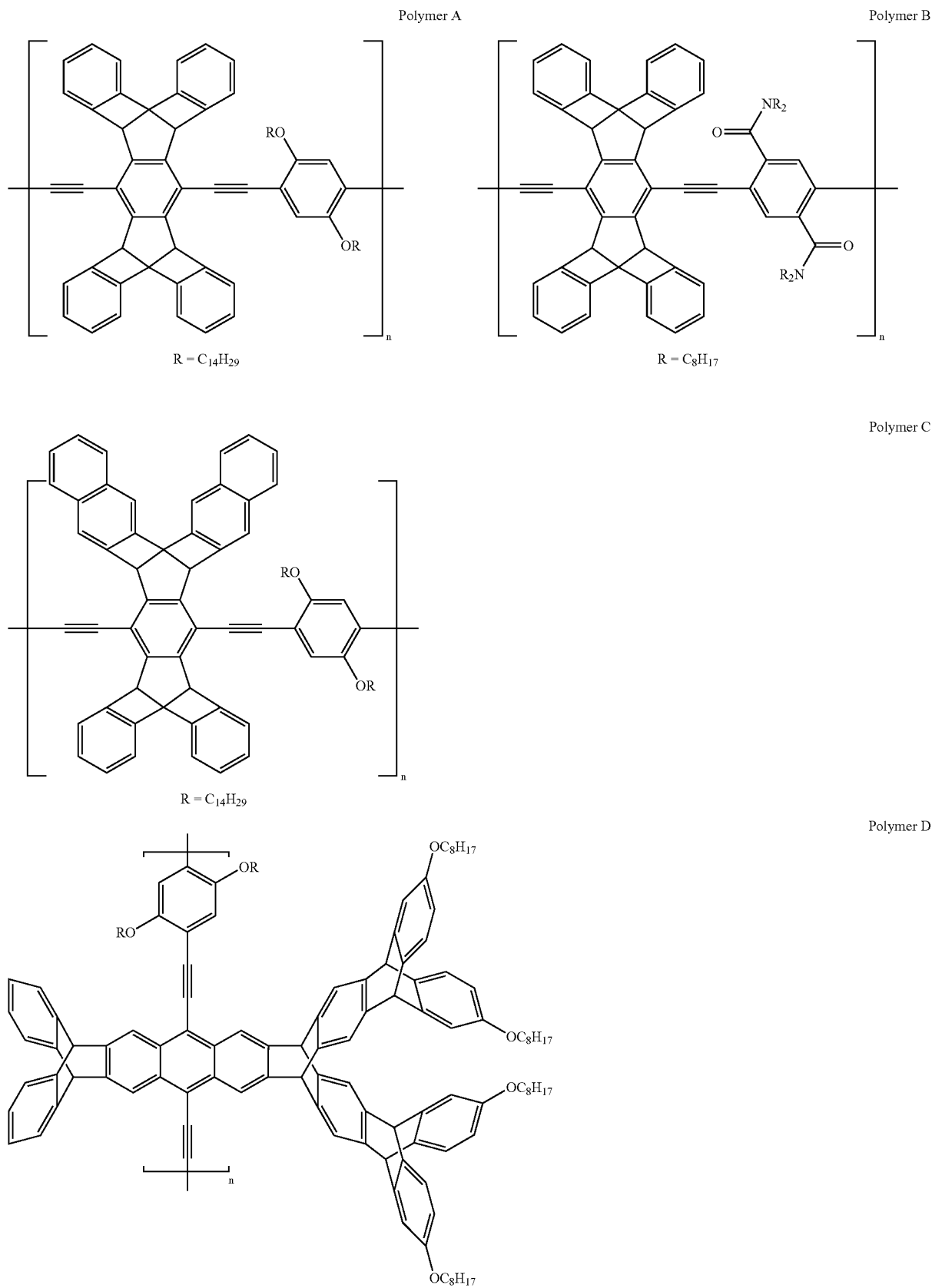

-continued

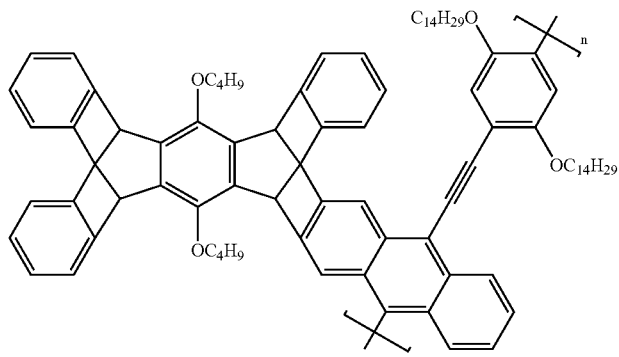

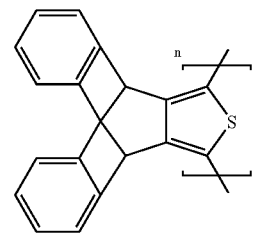

Figure 5A:
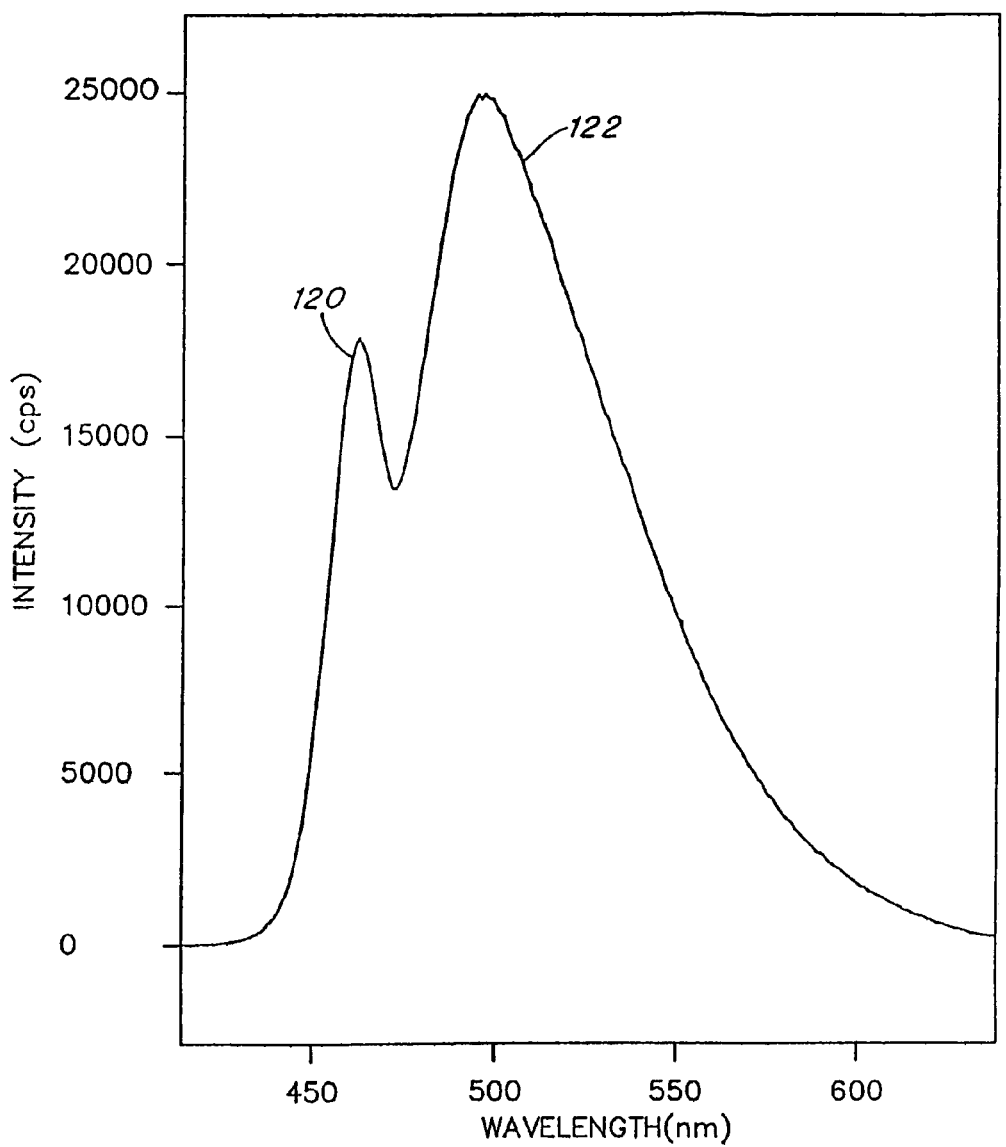
FIG. 5 shows emission spectra for polymer C and an exciplex band including polymer C.
Figure 5B:
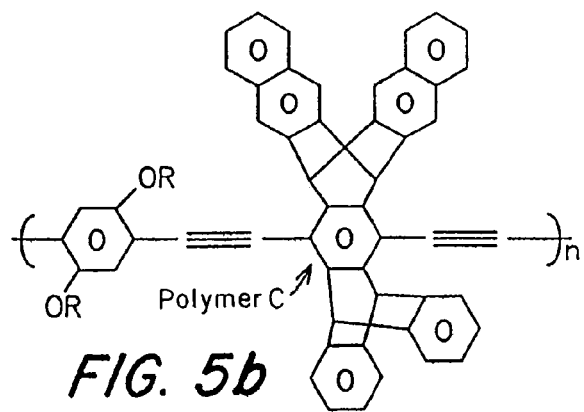

In one embodiment, at least one of G, H, I and J includes a naphthalene group that is a component of an exciplex structure. An "exciplex" is defined as an excited state transient dimer formed between a donor species and an acceptor species. The excited state is formed by photoexcitation of either the donor or the acceptor. Exciplexes can represent an intermediate in a charge transfer process from a donor to an acceptor species. FIG. 5 shows an emission spectrum of a thin film with an exciplex feature 122 for polymer C. The normal solution spectrum is shown by curve 120 which does not have an exciplex feature.

In one embodiment, E is selected from the group consisting of:

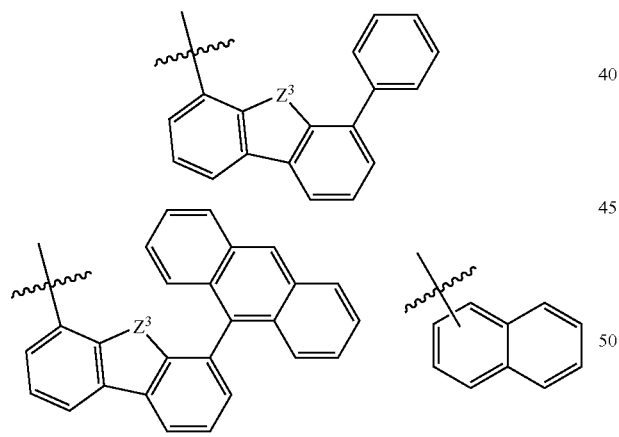

Any hydrogen in E can be substituted by $R^{17}$ where $R^{17}$ can be selected from the group consisting of $C_1$-$C_{20}$ alkyl, aryl, $C_1$-$C_{20}$ alkoxy, phenoxy, $C_1$-$C_{20}$ thioalkyl, thioaryl, C(O)$OR^{18}N(R^{18})(R^{19})$, C(O)N($R^{18}$)($R^{19}$), F, Cl, Br, I, $NO_2$, CN, acyl, carboxylate, hydroxy. $R^{18}$ and $R^{19}$ can be the same or different and each can be selected from the group consisting of hydrogen, $C_1$-$C_{20}$ alkyl, and aryl. $Z^3$ can be selected from the group consisting of O, S and $NR^{20}$ where $R^{20}$ can be selected from the group consisting of hydrogen, $C_1$-$C_{20}$ alkyl, and aryl.

In one embodiment, the polymeric composition comprises the structure:

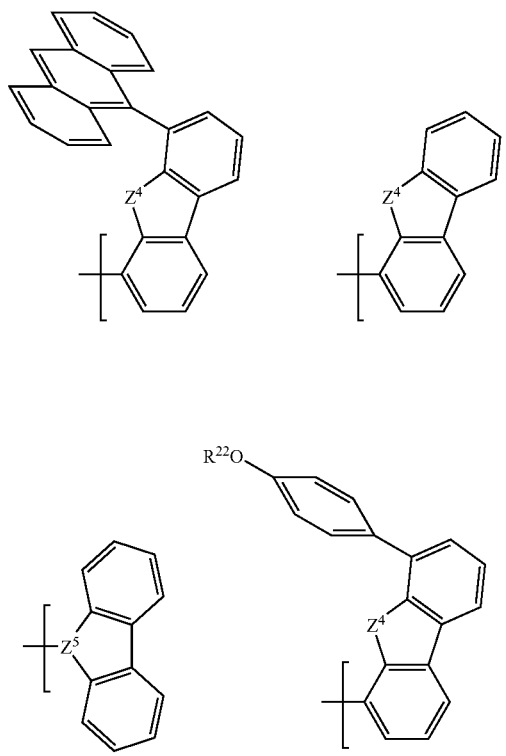

Q can be selected from the group consisting of:

-continued

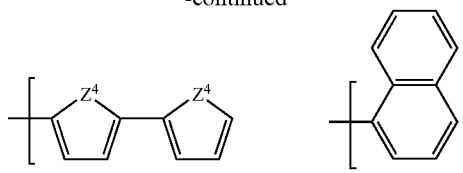

$R^{22}$ can be selected from the group consisting of hydrogen, $C_1$-$C_{20}$ alkyl and aryl. Any hydrogen in Q can be substituted by $R^{22}$, $R^{22}$ can be selected from the group consisting of $C_1$-$C_{20}$ alkyl aryl, $C_1$-$C_{20}$ alkoxy, phenoxy, $C_1$-$C_{20}$ thioalkyl, thioaryl, $C(O)OR^{23}$, $N(R^{23})(R^{24})$, $C(O)N(^{24})(R^{25})$, F, Cl, Br, I, $NO_2$, CN, acyl, carboxylate, hydroxy. $R^{23}$ and $R^{24}$ can be the same or different and each can be selected from the group consisting of hydrogen, $C_1$-$C_{20}$ alkyl, and aryl. $Z^4$ can be selected from the group consisting of O, S and $NR^{25}$, $Z^5$ can be selected from the group consisting of N and $CR^{25}$ and $R^{25}$ can be selected from the group consisting of hydrogen, $C_1$-$C_{20}$ alkyl, and aryl. Preferably, n is less than about 10,000.

In one embodiment, the polymeric composition comprises the structure:

$R^{26}$ can be selected from the group consisting of hydrogen, $C_1$-$C_{20}$ alkyl and aryl. Q is defined as above.

Other specific examples of polymeric compositions having features in accordance with the invention include:

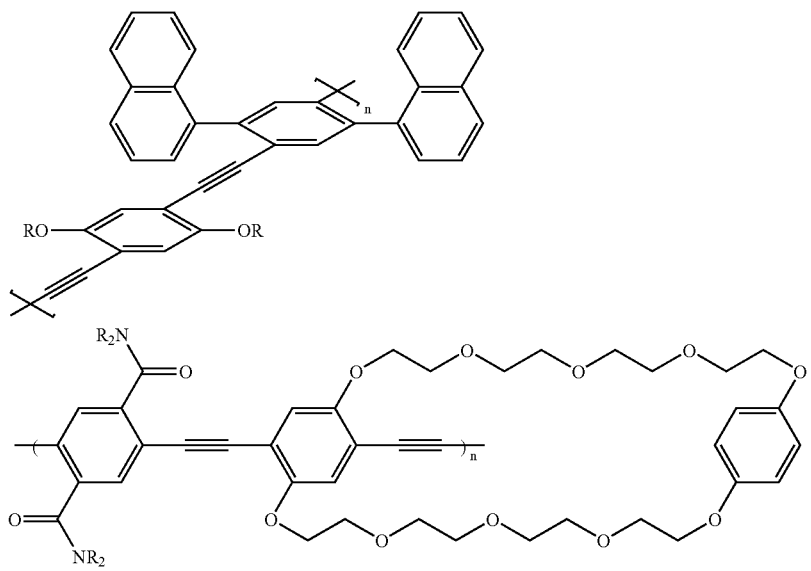

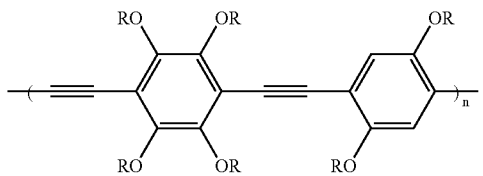

R = (CH$_2$)$_n$H, n = 1–16

In another embodiment, the polymeric compositions include triphenylene groups. FIG. 28 shows examples of triphenylene containing polymers 470-478.

Figure 29:
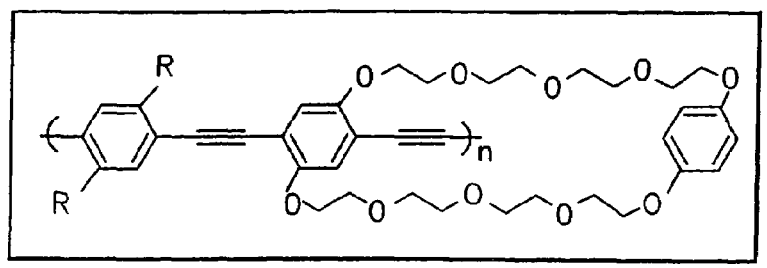
FIG. 29 shows an example of a cyclophane polymer structure.

Sensors comprising polymeric films also include cyclophane polymer types as shown in FIG. 29.

Another aspect of the invention provides a sensor that can include polymeric compositions of the invention. The polymeric compositions of the present invention have significant fluorescent yields. Because the fluorescence can be quenched in the presence of an acceptor molecule, the decrease in intensity can serve as a method for determining the presence or absence of an analyte. The sensor comprises a polymeric composition comprising the structure:

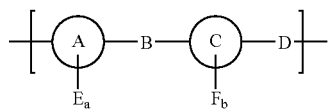

A, B, C, D, E, F, a and b are defined as above.

The sensor also includes a source of energy applicable to the polymeric composition to cause radiation emission. The energy can be selected from the group consisting of electromagnetic radiation, electrical energy and chemical energy. Preferably, the energy is of a frequency that can be absorbed by the polymer, resulting in an emission of radiation. In particular, when the electromagnetic energy is absorbed by the polymeric composition, luminescence occurs. Electroluminescence occurs when the composition absorbs electrical energy and chemiluminescence results when the composition absorbs chemical energy. The sensor also includes a device for detecting the emission, such as a photomultiplier, a photodiode or a charge coupled device.

In one embodiment, the sensor also includes an article to provide enhanced rigidity, sensitivity, selectivity, stability, or a combination of any number of these features, to the polymeric composition in the sensor. The article is typically positioned adjacent the polymer and can be selected from the group consisting of beads, nanoparticles, polymer fibers, waveguides and a film. The article can have a composition selected from the group consisting of a biological species, a polymer, a ceramic, a conductor and a semiconductor. Preferred biological species include a peptide, an oligonucleotide, an enzyme, an antibody, a fluorescent peptide, a fluorescent oligonucleotide and a fluorescent antibody. Examples polymers include polystyrene, polyethylene oxide, polyethylene, polysiloxane, polyphenylene, polythiophene, poly(phenylene-vinylene), polysilane, polyethylene terephthalate and poly(phenylene-ethynylene). The semiconductor and conductor can be selected from the group consisting of solids and nanoclusters. Preferred semiconductor materials include Group II/VI, Group III/V and Group IV semiconductors such as CDS, CdSe, InP, GaAs, Si, Ge and porous silicon. A preferred conductor is colloidal gold. Preferred ceramics include glass, quartz, titanium oxide and indium tin oxide.

Figure 33:
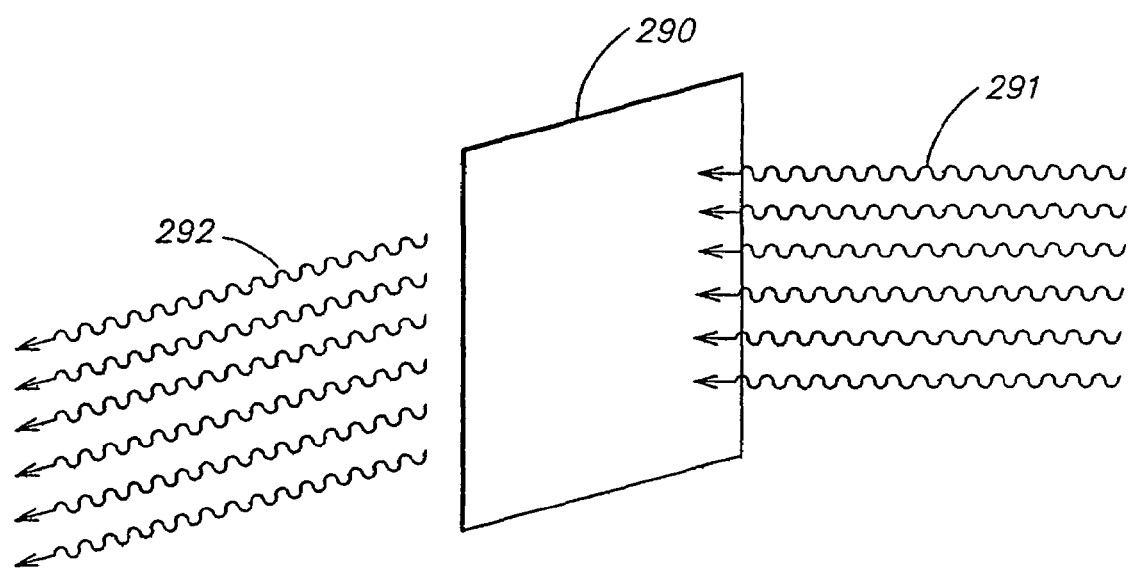
FIG. 33 shows a device comprising a transparent support coated with a polymer film capable of amplifying emission through sequential emission end re-absorption cycles.

In one embodiment, the article is capable of further enhancing the emission of a polymer. For example, a sensor can be provided comprising a polymer positioned adjacent a waveguide. Light emitted by the polymer in one can area can be captured by internal reflection in the substrate and then reabsorbed and re-emitted in a different region of the sensor. This process can occur many times before reaching a detector, resulting in a sensor with enhanced sensitivity. Sequential emission and reabsorption cycles increase the probability that an excitation will be quenched or trapped by an analyte. An example of a device that can achieve this effect is shown in FIG. 33 where a transparent support 290 is coated with a polymer film of the present invention. The polymer film is excited by a source of energy 291 on one side of transparent support 290 and emission 292 is detected from an edge on an opposite side of transparent support 290. A further optimization of this device can be achieved by using a waveguide. Excitations in this device can be initiated at one terminus of the waveguide and most of the light emerging from an opposite terminus will hav undergone multiple emission and re-absorption cycles.

Another aspect of the invention provides a method for detecting the presence of an analyte. The method involves providing a composition comprising the structure:

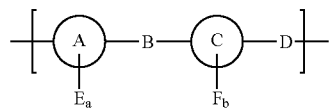

A, B, C, D, E, F, a and b are defined as above. The polymeric composition is exposed to a source of energy is applicable to the polymeric composition and the composition achieves an excited state to cause a first emission of radiation. The first emission can be fluorescence. The first emission is observed by obtaining an initial emission spectrum of the composition in the absence of the analyte. The excited state polymeric composition is then exposed to a medium suspected of containing an analyte. In one embodiment, the excited state composition is a donor species, the analyte is an acceptor species and electronic or energy transfer occurs from the excited state composition to the analyte, providing a route that results in the composition returning to ground state accompanied by a decrease in fluorescence intensity, due to a second emission of radiation. In another embodiment, the excited state composition is an acceptor species and the analyte is a donor species. A difference between the first emission and the second emission provides evidence of the presence of an analyte. The difference can be a change in wavelength values or intensity. Additionally, the difference can be a change in the conductivity. The difference can be caused by an electron transfer reaction between the composition and the analyte.

Specificity for a particular analyte by a polymer is a combination of size exclusion and chemical bonding. For example, more electron-rich polymers display a higher sensitivity to nitroaromatics. Thus, structure-function relationships can be obtained.

Figure 17:
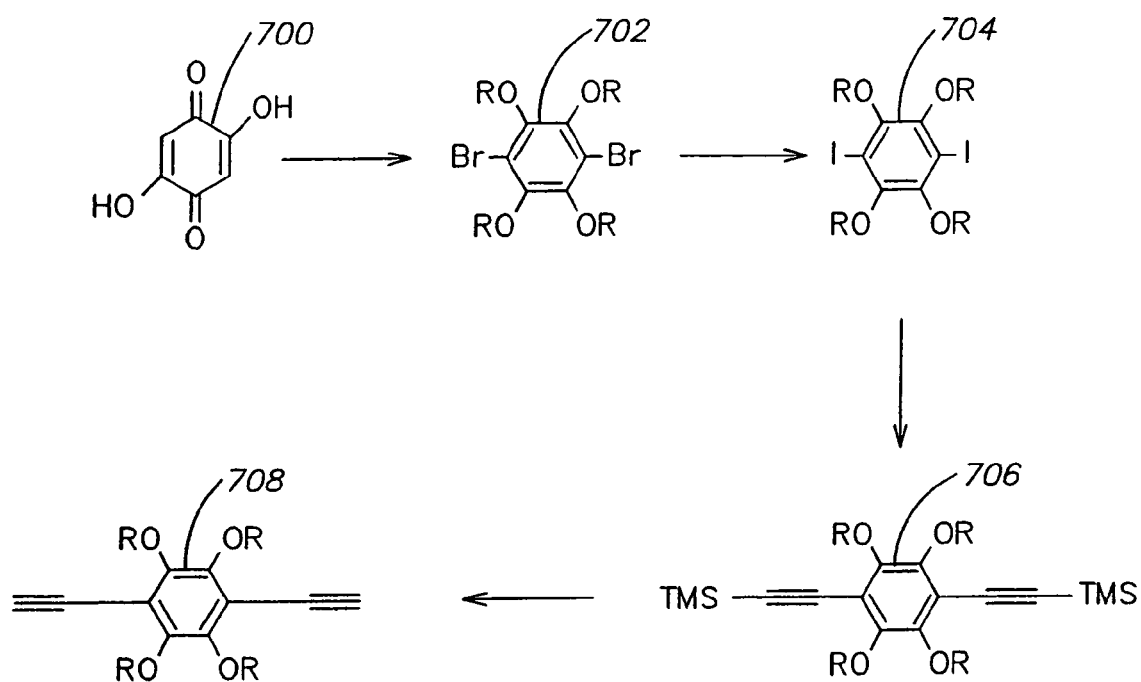
FIG. 17 shows a schematic synthesis of a monomer having acetylene functional groups.
Figure 18D:
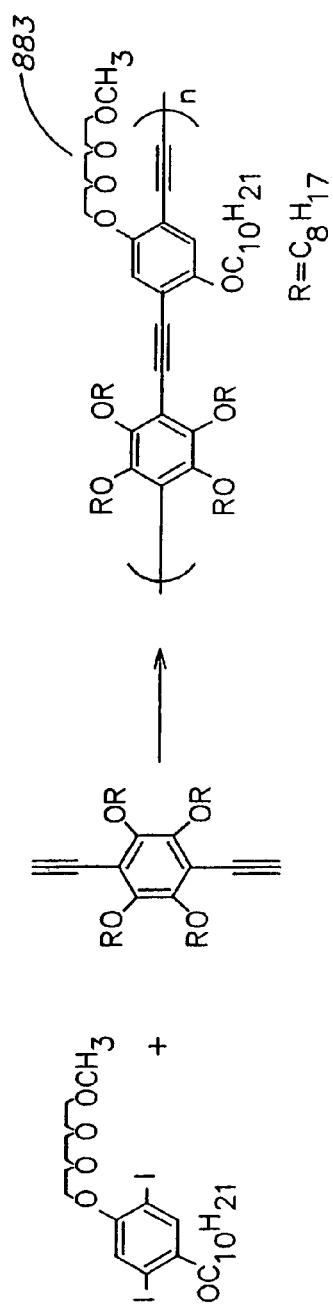
FIG. 18 shows a schematic synthesis for the preparation of acetylene-based polymers.
Figure 18E:
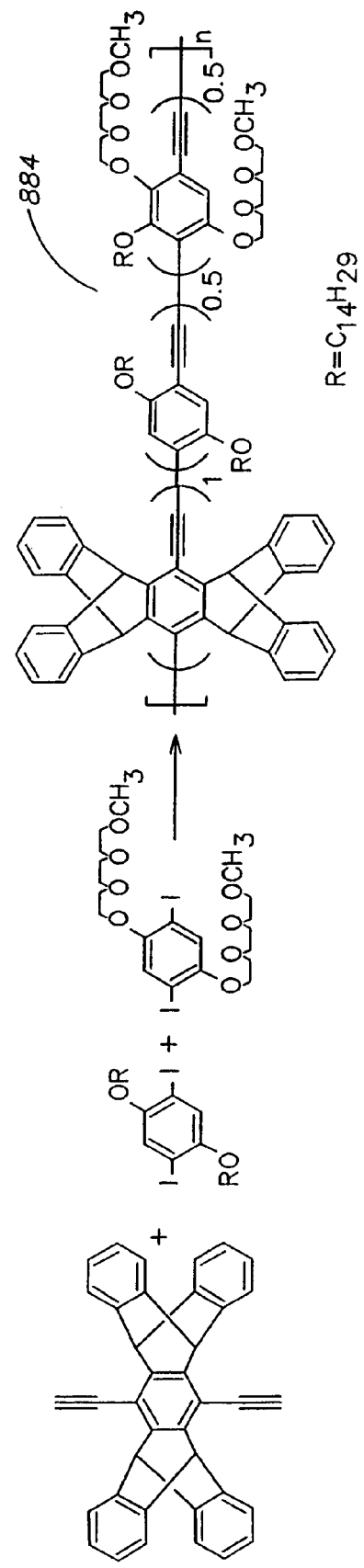

FIG. 17 shows a synthesis of monomer 708 that can be used to form polymers that are quenched more strongly in the presence of an equilibrium vapor pressure of TNT than that of DNT. In FIG. 17, reactant 700 can produce reactant 702 in three steps. By the addition of BuLi in THF followed by the addition of 80% $I_2$, molecule 702 can be transformed to 704. Conjugation can be achieved by the addition of trimethylsilylacetylene to 704 in the presence of 80% $Pd(PPh_3)_2Cl_2$. The TMS groups can be achieved from 706 by the addition of 91% KOH/MEOH to achieve monomer 708. By using monomer 708 for other similar acetylene derivatives, polymers 880-884 can be prepared, as shown in FIG. 18. Polymerization is effected by the addition of a coupling region, such as $Pd(dppf)_2Cl_2$, for polymer 880 and $Pd(PPh_3)_4$, for polymers 881-884. Such selectivity is surprising considering that the vapor pressure of DNT is about 100 times greater than that of TNT. Specific detection of TNT provides the capability to detect explosive devices in the gaseous phase. Examples of explosive devices include land mines.

Figure 6E:
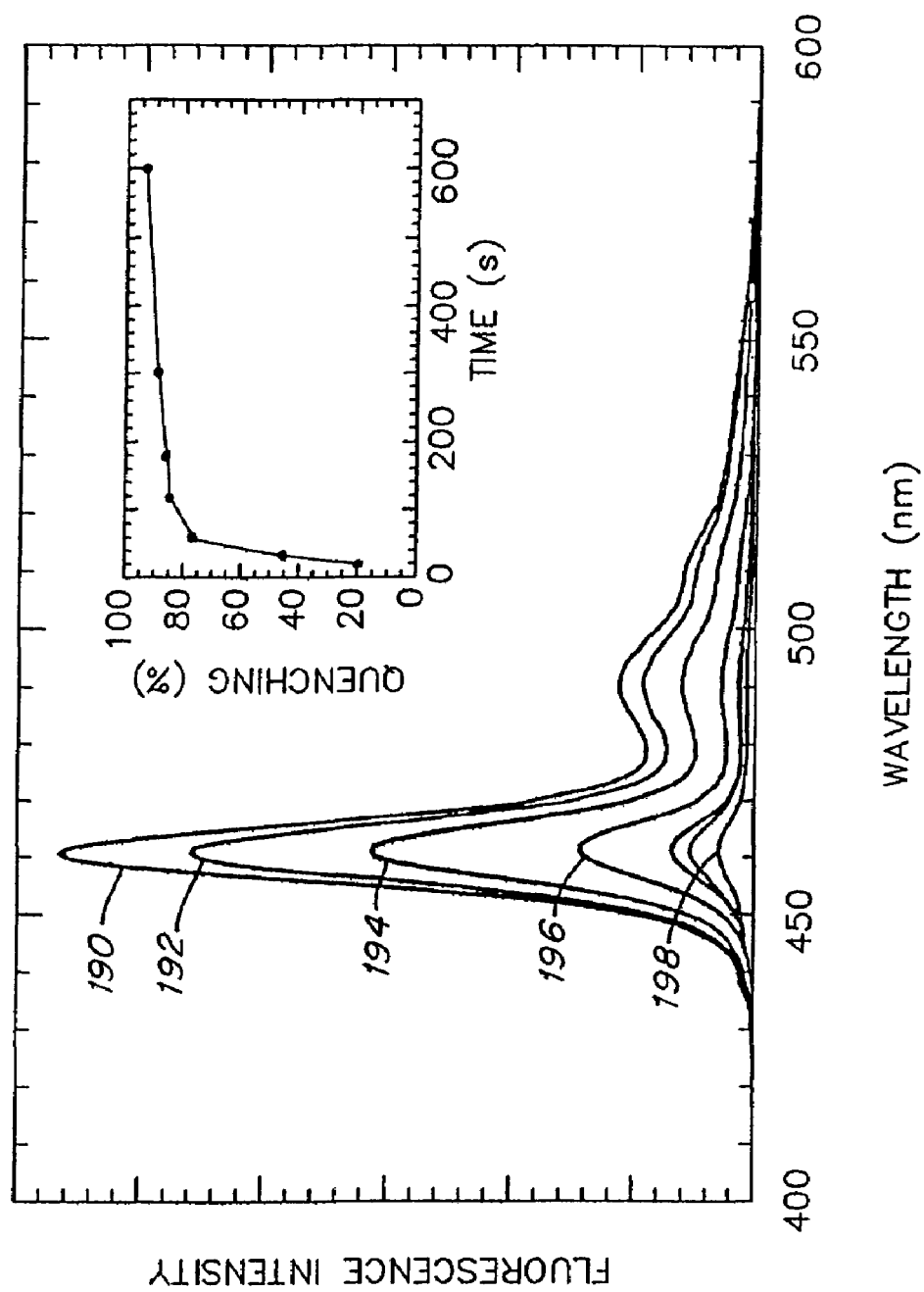
FIG. 6 shows emission spectra over time of (a) polymer A in the absence and presence of dinitrotoluene (DNT) vapor; (b) polymer A in the absence and presence of trinitrotoluene (TNT) vapor; (c) polymer A in the absence and presence of benzoquinone vapor; (d) polymer B in the absence and presence of DNT; (e) polymer A in the absence and presence of TNT and an inset shows a plot of percent quenching versus time.

FIG. 6 shows emission spectra of polymer A in the absence and in the presence of various analytes. In FIG. 6(*a*), an initial emission spectrum 150 is obtained in the absence of an analyte. The composition is then exposed to an analyte, dinitrotoluene (DNT) vapor, and a decrease in intensity is observed in the maxima of the spectra with time, as denoted by curves 152 (10 s), 154 (30 s), 156 (1 min.) and 158 (3 min.). FIG. 6(*b*) shows a detection of another example of an analyte, trinitrotoluene (TNT) vapor, by polymer A as evidenced a decrease in intensity is observed in the maxima of the spectra over time, as denoted by curves 160 (initial), 162 (10 s), 164 (30 s), 166 (1 min.) and 168 (10 min.). FIG. 6(*c*) shows a detection of another example of an analyte, benzoquinone vapor, by polymer A as evidenced by a decrease in intensity is observed in the maxima of the spectra over time, as denoted by curves 170 (initial), 172 (10 s), 174 (30 s), 176 (1 min.) and 178 (10 min.). FIG. 6(*d*) shows a detection of DNT, by polymer B as evidenced by a decrease in intensity is observed in the maxima of the spectra over time, as denoted by curves 180 (initial), 182 (10 s), 184 (30 s), 186 (1 min.) and 188 (10 min.). FIG. 6(*e*) shows a detection of TNT by polymer A as evidenced by a decrease in intensity is observed in the maxima of the spectra over time, as denoted by curves 190 (initial), 192 (10 s), 194 (30 s), 196 (1 min.) and 198 (10 min.). The inset of FIG. 6(*e*) shows a plot of percent quenching versus time.

FIG. 15 shows a variety of polymers, A-D, that are capable of detecting the presence of TNT vapor. A concentration of the vapor can be much less than about 1 ppb. As shown in FIG. 15, by varying the polymer type, enhanced emission intensities can be achieved and responsiveness can be optimized. For example, polymer type A shows the fastest response time, as indicated by a plateau achieved at a time of less than about 30 seconds.

Figure 16A:
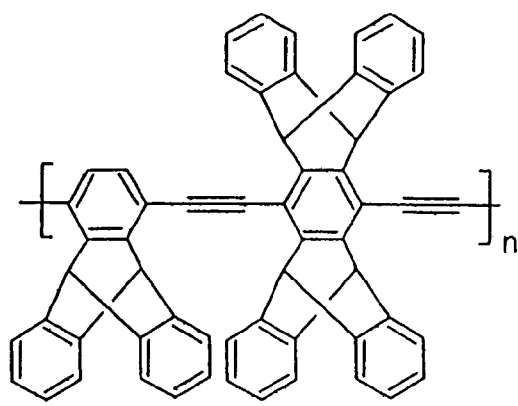
FIG. 16 shows a fluorescence intensity plot displaying a variation in intensities for an "all-iptycene" polymer
Figure 16B:
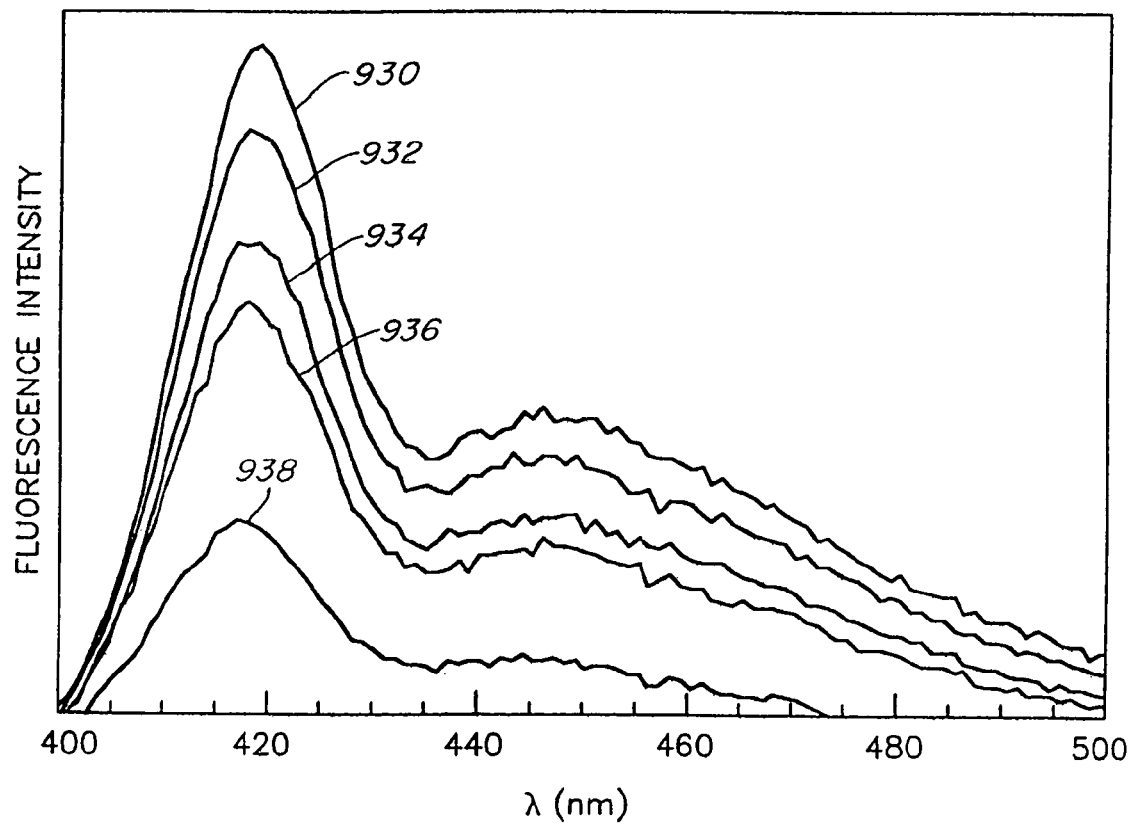

FIG. 16 shows a variation in fluorescence intensities for an "all-iptycene" polymer. The all-iptycene structure provides the polymer with excellent solubility and stability. The all-iptycene polymer is sensitive to TNT detection, and increased detection times provide decreased intensities. Curve 938 corresponds to a detection time of 480 s, curve 936 corresponds to a time of 120 s, curve 934 corresponds to a time of 60 s, curve 932 corresponds to a time of 30 s, and curve 930 corresponds to a time of 0 s.

Figure 19A:
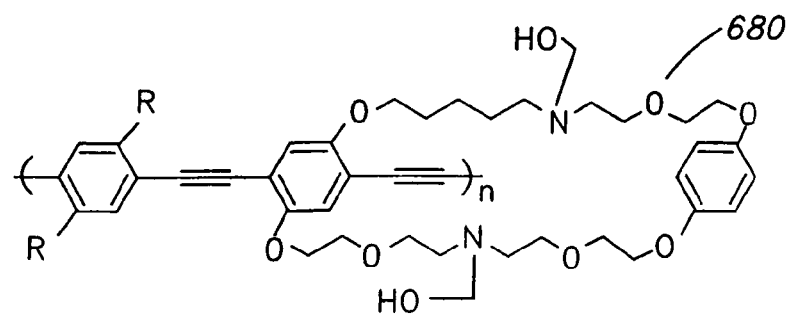
FIG. 19 shows examples of polymer structures that can provide hydrogen-bonding interactions as well as charge-transfer interactions.
Figure 19B:
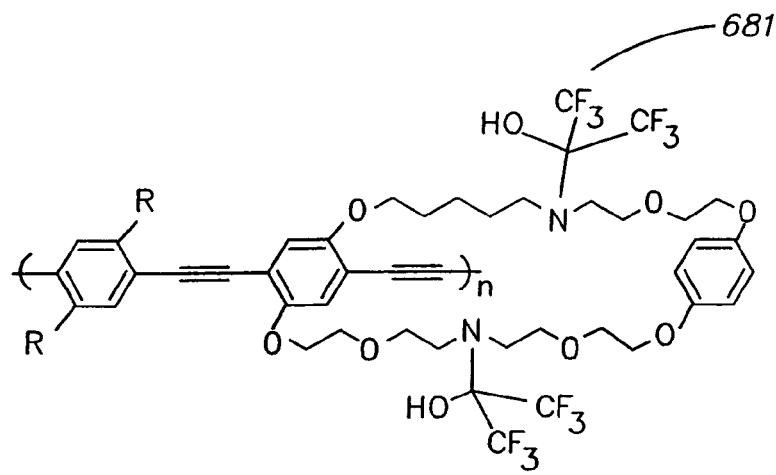
Figure 19C:
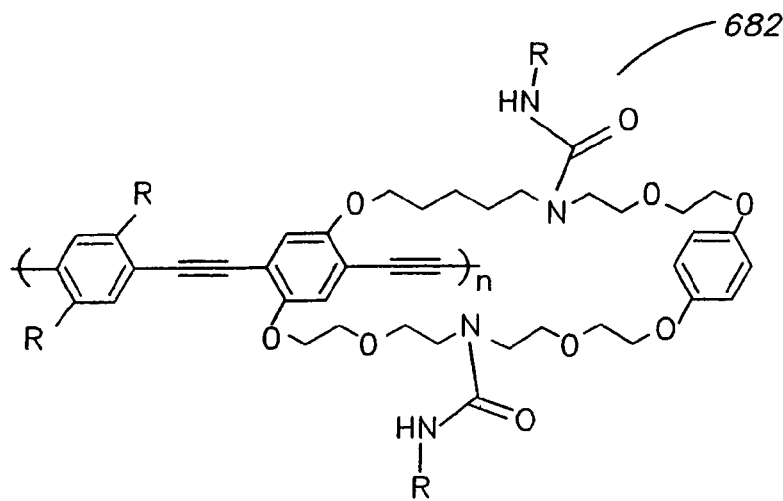
Figure 20A:
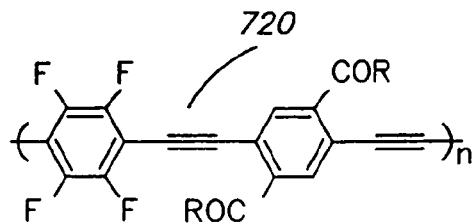
FIG. 20 shows examples of electron-poor polymer structures.
Figure 20B:
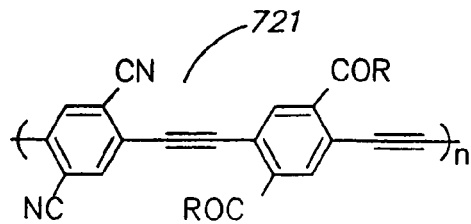
Figure 20C:
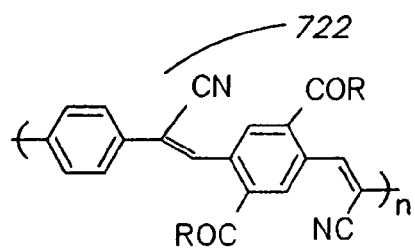
Figure 20D:
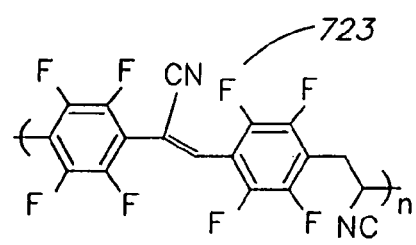
Figure 20E:
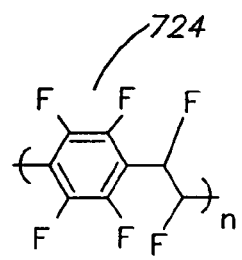
Figure 20F:
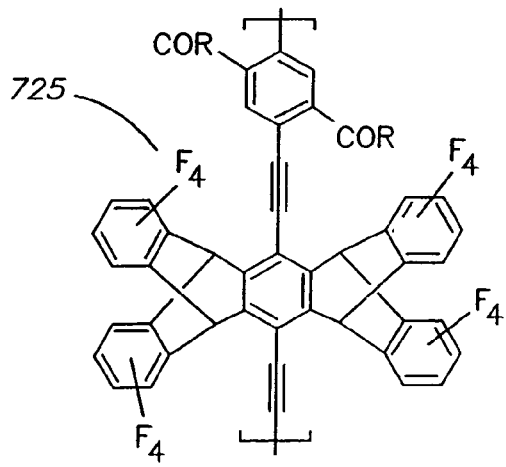

Polymers having hydrogen-bonding capabilities can also be synthesized. Thus, in one embodiment, the invention provides the ability to detect analytes capable of hydrogen-bonding interactions. FIG. 19 shows polymers 680-682 that can provide hydrogen-bonding interactions as well as charge-transfer interactions. Lewis and Bronsted base/acid sites can be used to impart selectivity for specific analytes.

Figure 21A:
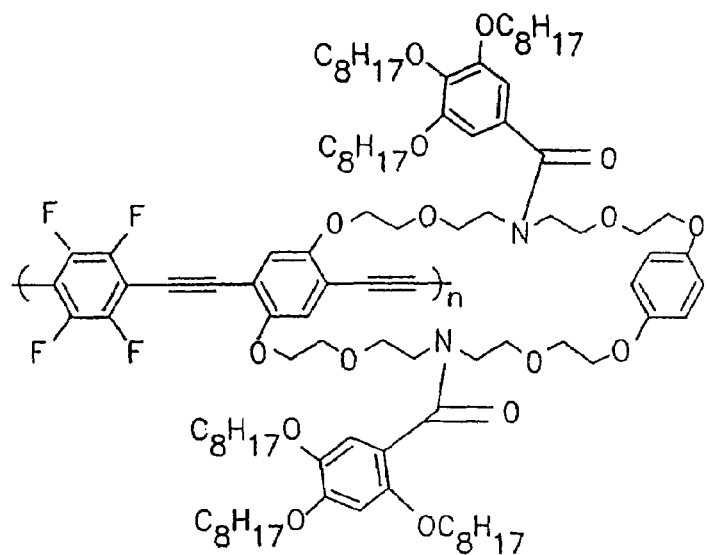
FIG. 21 shows an example of a polymer structure having fluoride groups and displaying spectral data in the presence of TNT.
Figure 21B:
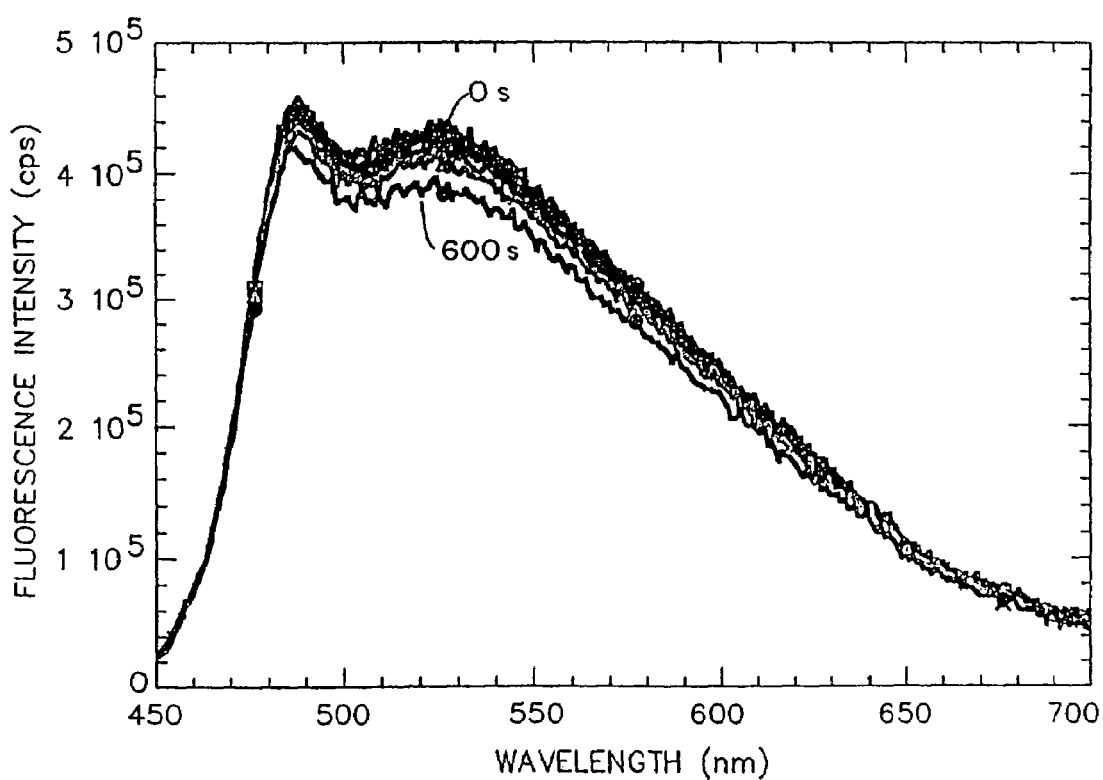
Figure 22A:
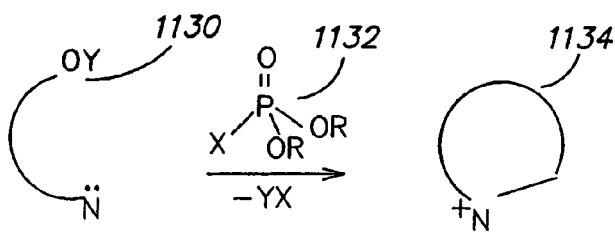
FIG. 22 shows an example of groups that are reactive with phosphate ester groups.
Figure 22B:
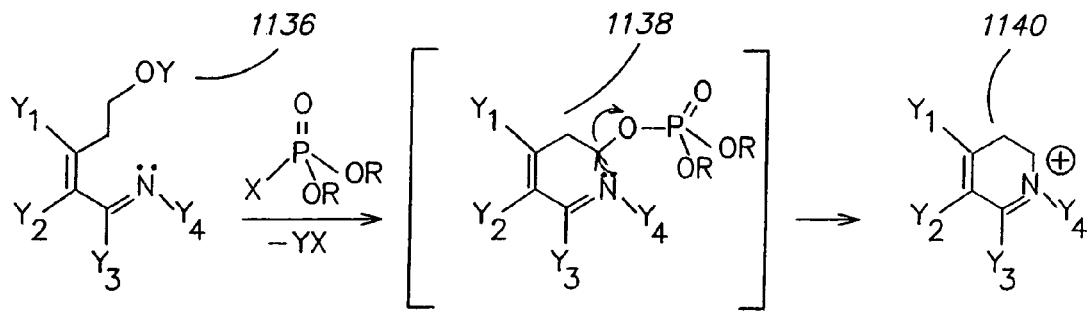
Figure 22C:
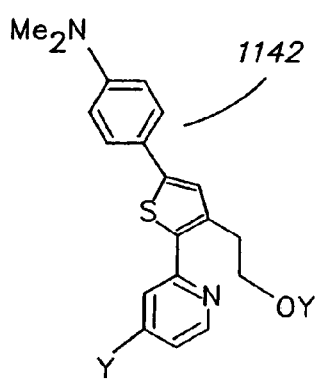
Figure 22D:
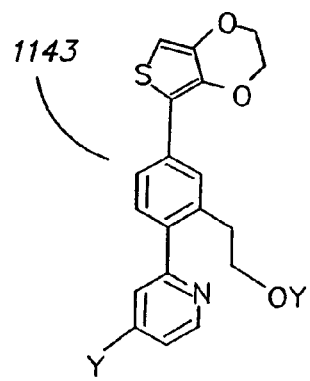
Figure 22E:
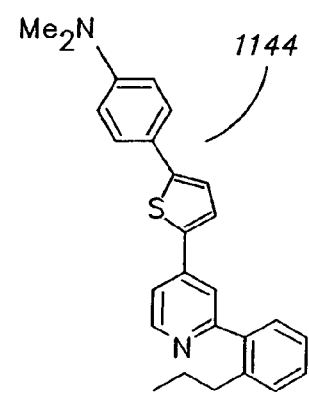
Figure 22F:
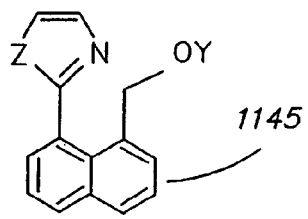
Figure 22G:
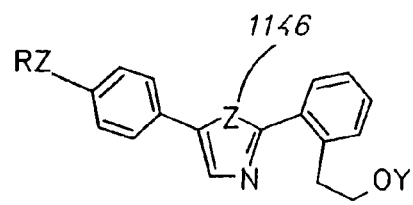

Typically, electron poor polymers can enable quenching by electron-rich analytes and thus, in one embodiment, sensors having specificity for electron-rich analytes are provided. Thus, sensitivity to electron-rich analytes can be achieved by substituting a polymer with groups that increase electron affinity. FIG. 20 shows examples of electron poor polymers 720-725, where electron poor characteristics can be conveyed by groups such as fluoride and cyano groups. FIG. 21 shows an example of a polymer having fluoride groups. This polymer shows that fluorine is particularly effective at producing a polymer that is not readily quenched by TNT. This effect is likely due to the diminished reducing ability of the polymer. As shown in the blot, varying the ejection time from 0 s to 600 s shows very little difference in fluorescence intensities for TNT. Thus, these polymers can function as sensory elements for hydroquinones and other electron-rich aromatics that are of biological or environmental importance. Examples include dioxin, dopamine, aniline, benzene, toluene and phenols.

Figure 7:
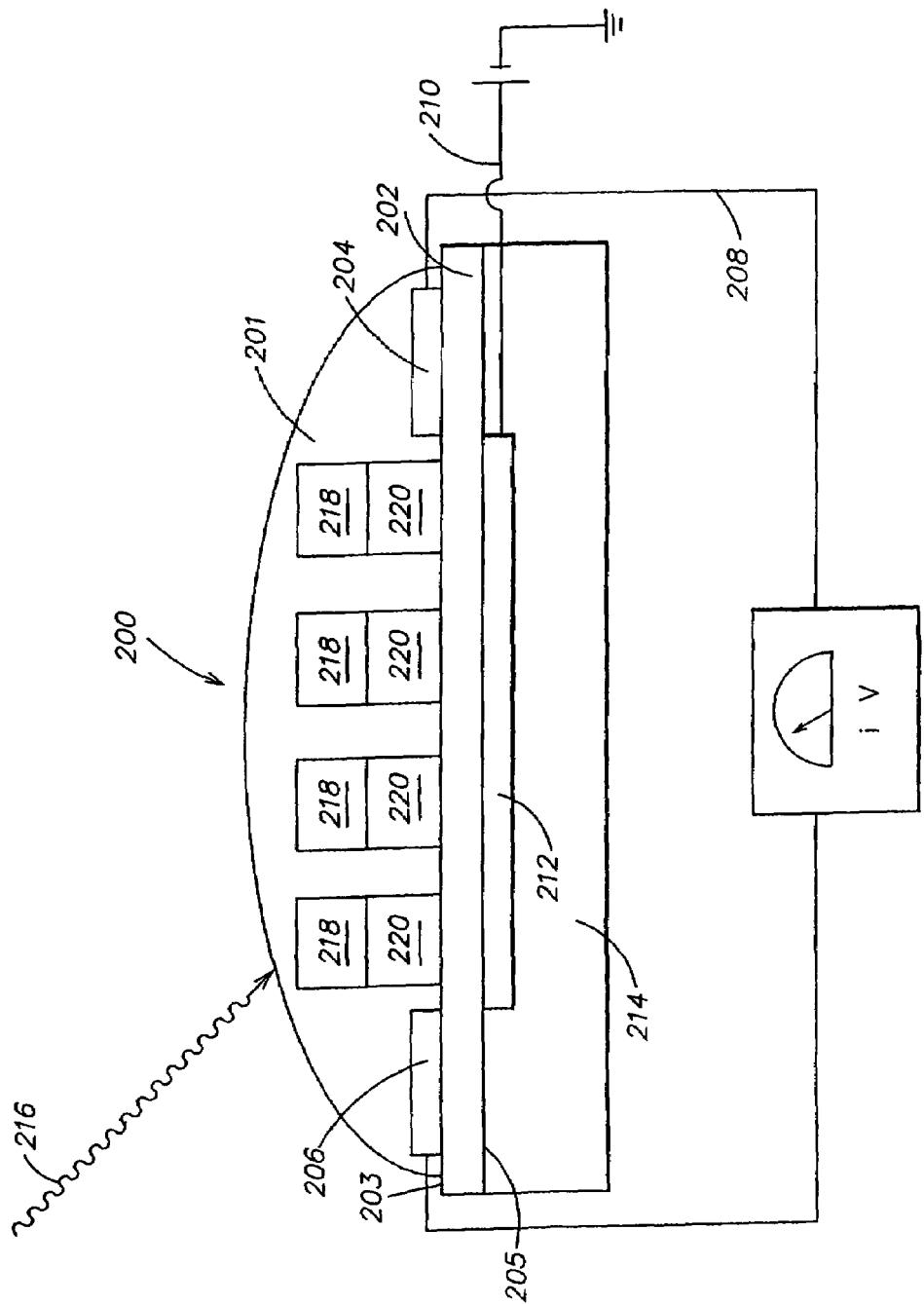
FIG. 7 shows a schematic of a field-effect transistor.

Another aspect of the invention provides a field-effect transistor. One embodiment of a field effect transistor is depicted in FIG. 7. The field-effect transistor 200 includes an insulating medium 202 having a first side 203 and an opposing second side 205. A polymeric article 201 is positioned adjacent the first side 203 of the insulating medium. Preferably the polymeric article has a composition in accordance with those of the invention as defined previously. A first electrode 204 is electrically connected to a first portion of the polymeric article 201 and a second electrode 206 is electrically connected to a second portion of the polymeric article 201. Each electrode 204 and 206 is positioned on the first side 203 of the insulating medium 202. The first electrode 204 is further connected to the second electrode 206 by an electrical circuit 208 external of the polymeric structure. A gate electrode 212 is positioned on the second side 205 of the insulating medium 202 in a region directly below the polymeric structure. The gate electrode 212 is further connected to a voltage source 210. A source of electromagnetic radiation 216 is positioned to apply the electromagnetic radiation to the article. The gate electrode 212 can be supported by a layer 214 such as $SiO_2$ or Si. At least one species, shown as 218, is associated with the article. Exposing the polymeric article to the electromagnetic radiation, results in species 218 being a component of an excited state structure.

Thus, the polymeric article achieves an excited state structure which can accept or donate charge to the species 218 associated with the article. The article also functions to carry the charge 220 to a region between the first and second electrode. In one embodiment, the first and second electrode is a source and drain electrode respectively. In this embodiment, the article injects charge 220 and changes the current between the source and drain electrodes. Prior to exposing the polymeric article to electromagnetic radiation, a current between the source and drain electrodes is a first current. After exposing the polymeric article to electromagnetic radiation, the current between the source and drain electrodes is a second current. Preferably the second current is greater than the first current.

Another embodiment provides an improvement over the first embodiment where the field-effect transistor further comprises a polymeric article which effectively transports charge. The polymers of the invention are effective for achieving high luminescent yields and functioning as a charge-injection polymer. In this embodiment, the field-effect transistor has an insulating medium having a first side and an opposing second side. A first polymeric article is positioned adjacent the first side of the insulating medium. Preferably this first polymeric article is a charge-conducting polymer and can be selected from the group consisting of polythiophene, polypyrrole, polyacetylene, polyphenylene and polyaniline. In another embodiment, the first polymeric article can be any polymer of the invention described previously. First and second electrodes are connected to first and second portions of the first polymeric article respectively. Each electrode is positioned on the first side of the insulating medium. The first electrode is further connected to the second electrode by an electrical circuit external of the first polymeric article. A gate electrode is positioned on the second side of the insulating medium below the first polymeric article, the gate electrode being connected to a voltage source. The invention comprises a second polymeric article positioned adjacent the first polymeric article. The second polymeric article is preferably a charge-injecting polymer having a composition in accordance with those of the invention as described previously. The field-effect transistor further includes a source of electromagnetic radiation applicable to a second polymeric article. At least one species is associated with the second polymeric article. The at least one species, which upon exposing the polymeric article to the electromagnetic radiation, is a component of an excited state structure.

Another aspect of the present invention provides a sensor comprising an article including at least one layer including a polymeric composition. The polymeric composition includes a reporter chromophore and the article further comprises an activation site wherein the reporter chromophore is capable of activation by an analyte at the activation site. An energy migration pathway within the polymeric composition allows energy to be transferred from the pathway to the activation site. Referring back to FIG. 1, polymer 551 can have reporter chromophores 552 positioned on the polymer. Chromophores 552 can also be dispersed within a bulk of the polymer 551. Excitation energy traversing through migration pathway 550 can transfer between various energy states of continually decreasing HOMO-LUMO gap. If chromophore 552 has a HOMO-LUMO gap greater than a HOMO-LUMO gap of at least a portion of the energy migration pathway and more preferably greater than a substantial portion of the energy migration pathway, energy transfer between the pathway 550 and chromophore 552 does not occur and only polymer emission 554 results.

If, however, the chromophore 552 is activated by an analyte, reporter chromophore 556 can result, where a HOMO-LUMO gap is less than a HOMO-LUMO gap of at least a portion of the energy migration pathway 550 and more preferably less than that of a substantial portion of energy migration pathway 550. By this arrangement, energy transfer can occur between polymer 551 and activated chromophore 556 to cause chromophore emission 558.

"Activation" by an analyte results in a reporter chromophore having a lower energy resulting in a decrease in the HOMO-LUMO gap. In one embodiment, activation by an analyte results in a chromophore having a smaller HOMO-LUMO gap than that of at least a portion of the migration pathway and preferably smaller than a substantial portion of the migration pathway. Activation can also be caused when an analyte interacts or reacts with a partner, and the combination of analyte and partner is capable of activating the chromophore.

An example of a sensor that has the arrangement as shown in FIG. 1 is a sensor having a polymer of a first color. Upon activation, the chromophore can have a lower energy (red-shifted) that allows optimal energy transfer from the polymer. The activated chromophores exhibit a second color and the films have the appearance of the second color. Thus, it is an advantageous feature of the present invention that the polymer films can first amplify an emission by channeling all of the emission through a few activated luminescent species. In this way, only a small number of reporter chromophores need to be activated to effect a total change in an appearance of the polymer. Detection of analytes can be visually observed by a color change of the polymer films.

In one embodiment, the invention provides a sensor that is capable of detecting chemical warfare agents, and particularly agents that can be detected in a gaseous or liquid phase. In one embodiment, the sensor is specific for chemical warfare agents and insecticides having reactive phosphate ester groups. An example of a chemical warfare agent that can be detected according to the invention is sarin and an example of an insecticide is parathion.

FIG. 22 shows an example of groups that are reactive with phosphate ester groups found in chemical warfare agents and insecticides. Group 1130, upon reaction with a phosphate ester group 1132 results in cyclization to form group 1134. Typically, reporter chromophores groups 1130 have higher energy absorptions and are less emissive than reporter chromophores having group 1134. In the transformation from a less emissive to a more emissive group, the band gap changes from high to low. A specific example of group 1130 is group 1136 which undergoes cyclization upon reaction with phosphate ester groups through intermediate 1138 to produce the cyclized compound 1140. X can be Cl, F, or CN or other electron-withdrawing substituents; Y can be hydrogen or $SiR_3$; and $Y_1$ and $Y_2$ can be conjugated groups such as aromatic rings. Other examples of groups that are sensitive to phosphate esters are shown as groups 1142-1146, where Y can be hydrogen, an alkyl group or an alkoxy group, preferably methyl and methoxy and hydrogen. Y can also be $SiR_3$, which can provide selectivity to agents having X=fluorine.

Figure 11B:
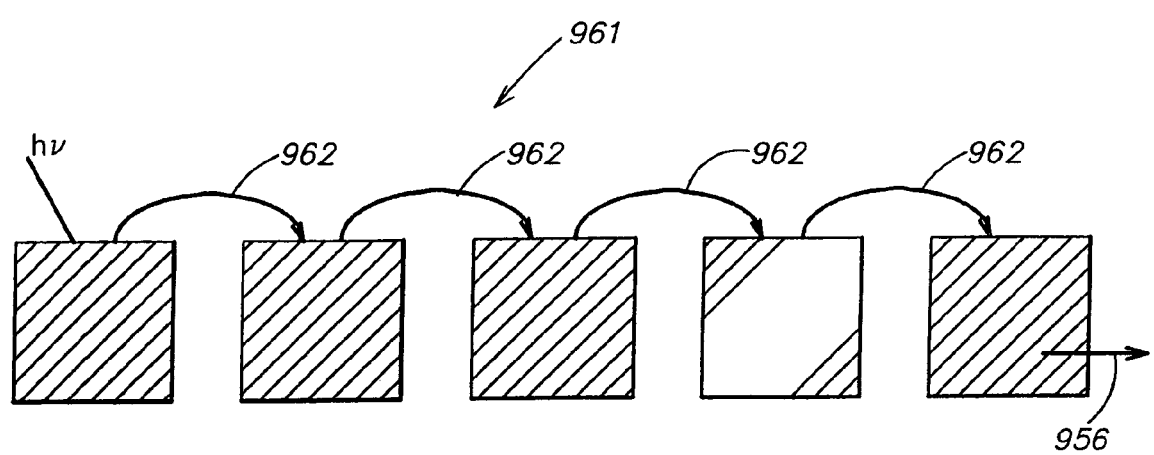
FIG. 11B schematically shows amplified emission of a multi-layer of polymers in series.
Figure 12C:
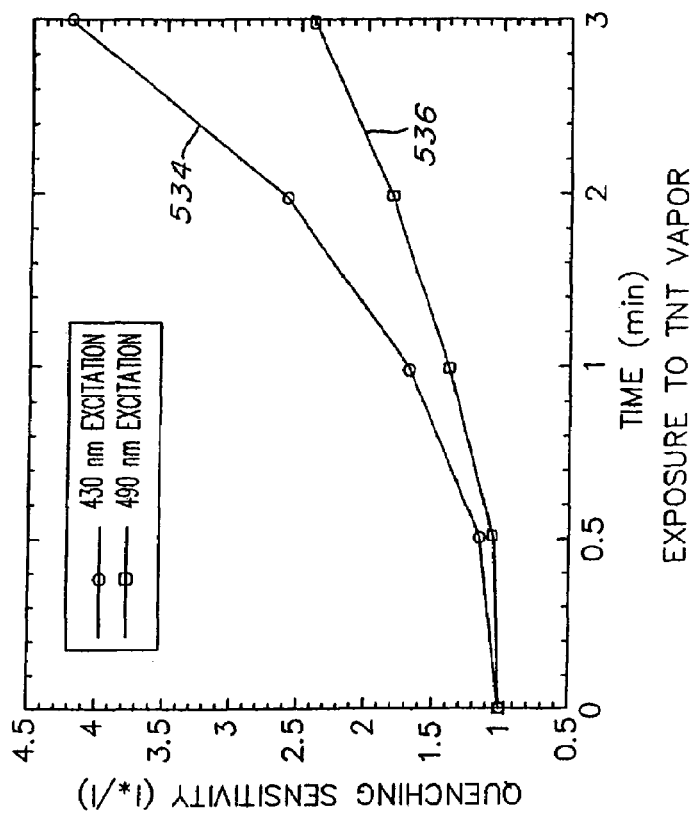
FIG. 12 shows a plot of enhanced sensitivity of the sensor for TNT when a donor polymer is in series with an acceptor polymer.
Figure 12A:
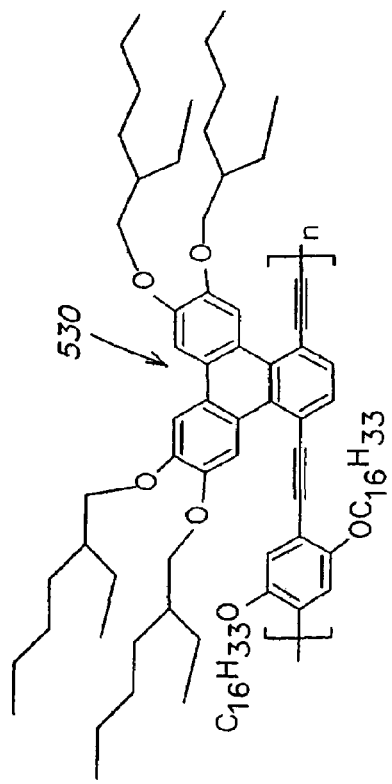
Figure 12B:
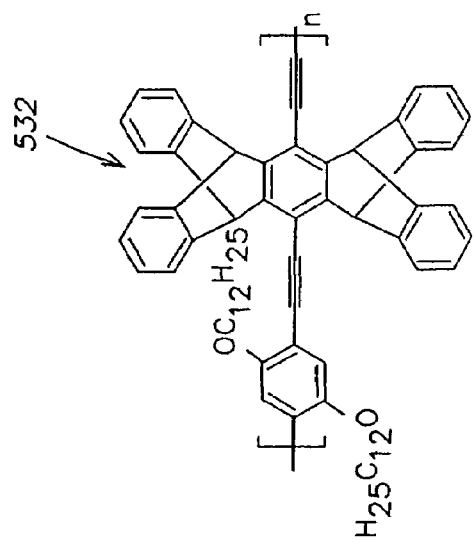
Figure 13:
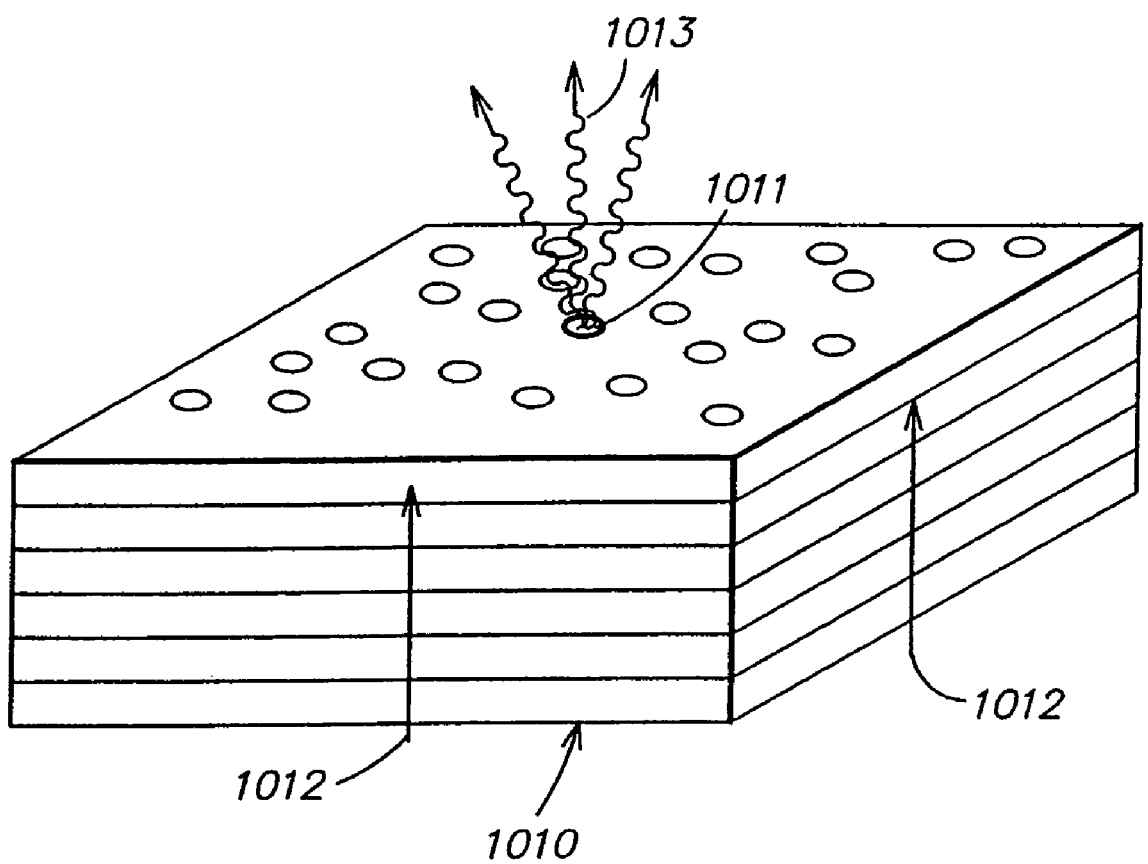
FIG. 13 shows a schematic of a multi-layer sensor having a gradient of energy band gaps and an activated chromophore at a surface of the multi-layer.
Figure 14A:
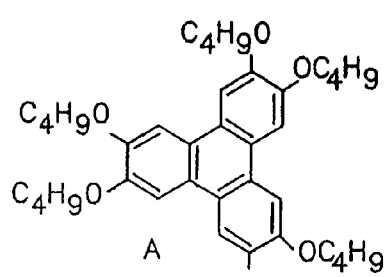
FIG. 14 shows a range of emissions for transporter chromophore A and a variety of polymers B-F.
Figure 14B:
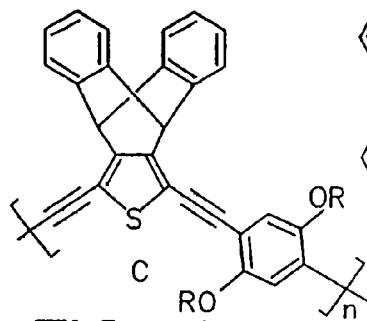
Figure 14C:
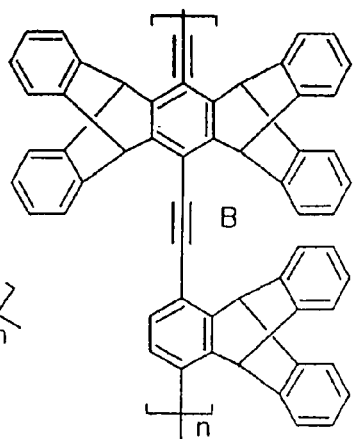
Figure 14D:
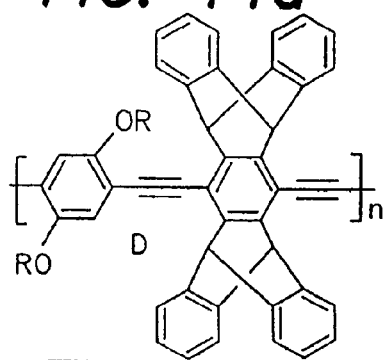
Figure 14E:
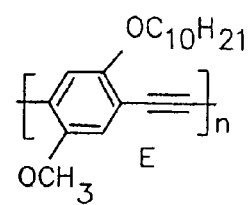
Figure 14F:
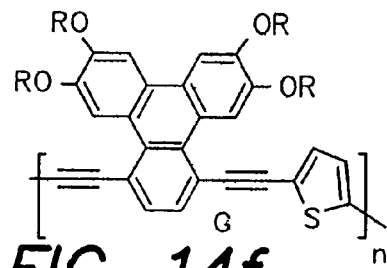
Figure 14G:
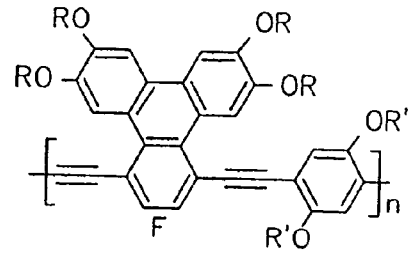
Figure 14H:
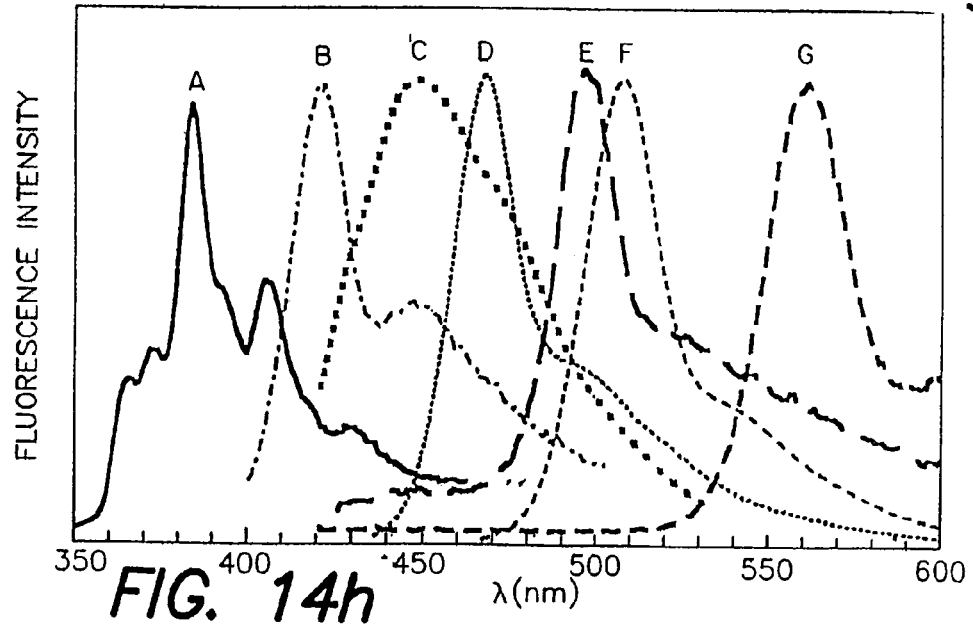
Figure 15A:
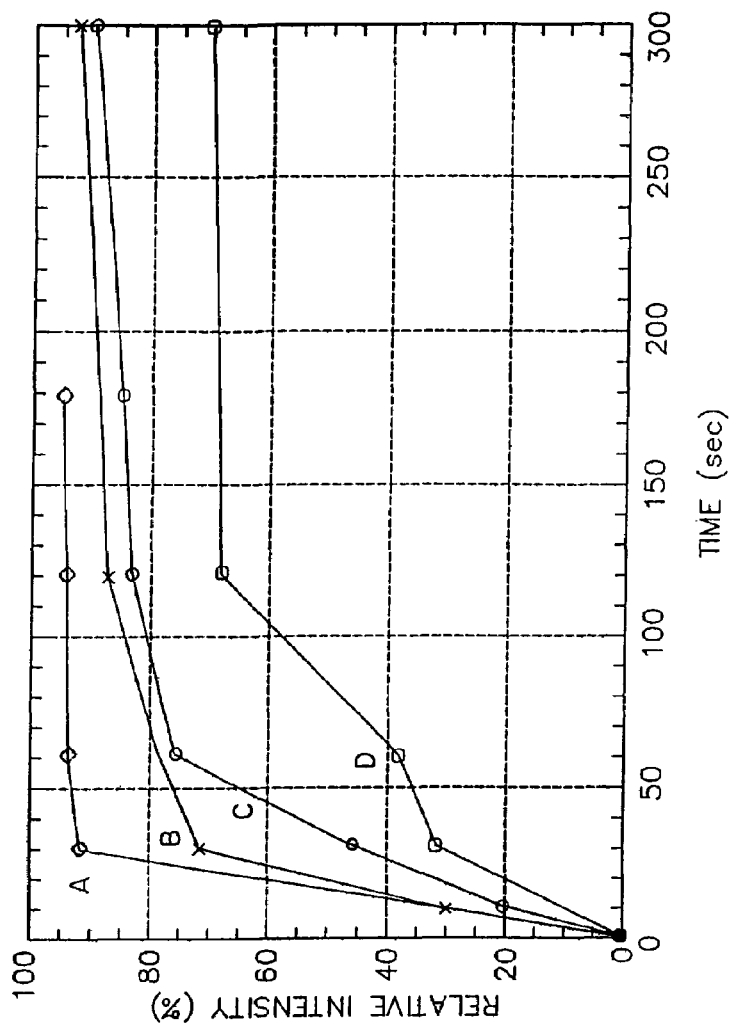
FIG. 15 shows polymers A-D that are capable of detecting the presence of TNT vapor, as indicated by an intensity plot over time.
Figure 15B:
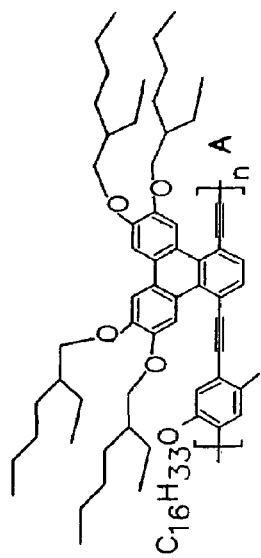
Figure 15C:
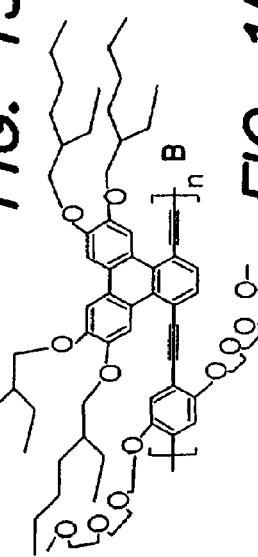
Figure 15D:
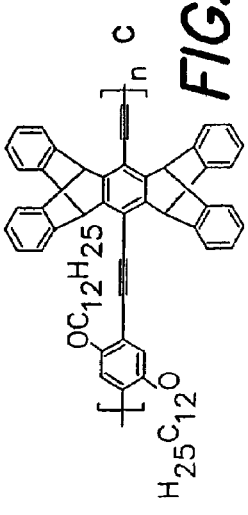
Figure 15E:
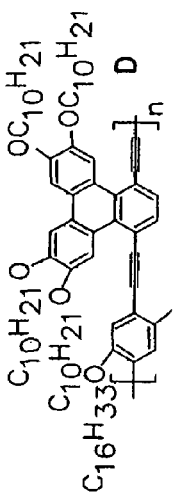

In one embodiment, the article comprises a first layer of a first polymer and a second layer of a second polymer, the first layer being positioned adjacent a second layer. A chromophore is present in the first and second layers. An energy migration pathway is continuous through the first and second layers. This arrangement is similar to placing amplifiers in series. If an emission is initiated in one polymer and collected from another polymer, then a net amplification is the product of the amplification contributed by each of the two different polymers. FIG. 11A shows emission 950 at a first energy for a first polymer 951 and emission 952 at a second energy for a second polymer 953. Article 955 schematically shows polymers 951 and 953 placed in series, i.e. as a double layer, and energy can migrate along pathway 958 to provide amplified emission 954, which is a product of the emissions of polymers 951 and 953 (i.e. emission 950 times emission 952). FIG. 11B shows article 961 having a multi-layer, wherein energy migrates along pathway 962 resulting in enhanced emission 956 which is a product of the emission of each individual polymer. FIG. 12 shows a demonstration of enhanced sensitivity of a sensor for TNT. Polymer 532 is a donor polymer that exhibits a dominant absorbance at 430 nm and polymer 530 is an acceptor polymer having a dominant absorbance at 490 nm. Polymers 530 and 532 are placed in series. By exposing the double layer to a 490 nm excitation (specific for acceptor polymer 530), curve 536 is obtained. By exposing the resulting double layer to a 430 nm excitation (specific for donor polymer 532), energy can be amplified by traveling from a higher energy polymer to a lower energy polymer, and this amplification is demonstrated by the enhanced intensity curve 534. FIG. 13 shows a schematic of a multi-layer sensor 1010, having a gradient of energy band gaps as indicated by arrows 1012. Activated reporter chromophore 1011 emits enhanced intensity 1013.

The band gaps of the polymers can be tailored by varying the molecular structure and providing different substituted groups on the polymers. FIG. 14 shows a transporter chromophore A and a variety of polymers B-F and their resulting emissions. From FIG. 14, this class of polymers shows a range of emissions from approximately 380 nm to approximately 560 nm.

The polymer can be a homo-polymer or a co-polymer such as a random co-polymer or a block co-polymer. In one embodiment, the polymer is a block co-polymer. An advantageous feature of block co-polymers is that the effect of a multi-layer can be mimicked. Each block will have different band gap components and by nature of the chemical structure of a block co-polymer, each gap component is segregated. Thus, amplified emissions can be achieved with block co-polymers. Thus, a broad scope of structures can be produced. Band gaps, amplifications and selectivities for analytes can be achieved by modification or incorporation of different polymer types. The polymer compositions can vary continuously to give a tapered block structure and the polymers can be synthesized by either step growth or chain growth methods.

Figure 24:
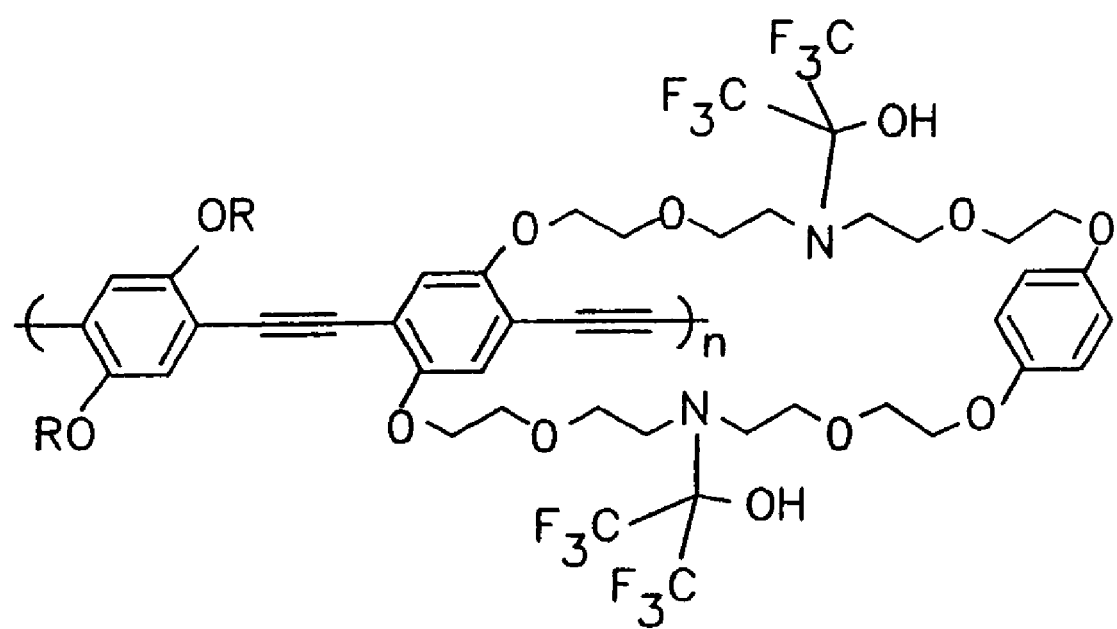
FIG. 24 shows an example of a polymer structure substituted with fluorinated alcohol groups for hydrogen bonding nitro groups.

Another aspect of the present invention provides a polymer capable of emission, wherein the emission is variable and sensitive to a dielectric constant of a surrounding medium. FIG. 24 shows an example of a polymer substituted with fluorinated alcohol groups for hydrogen bonding with weak hydrogen bonded acceptors such as nitro groups. Chromophores having such fluorinated alcohol groups can experience an emission sensitive to dielectric constants and can be used to detect the binding of high explosives such as RDX (hexahydro-1,3,5-trinitro-1,3,5-triaxine), PETN (2,2-bis[(nitrooxy)-methyl]-1,3-propanediol dinitrate (ester)) and other nitro-containing species.

Another aspect of the present invention provides a sensor having a reporter chromophore capable of emission, wherein the emission is variable and sensitive to an electric field of a medium surrounding the chromophore. Selective matching of energies involved in the energy migration pathway to a vast array of the activated and unactivated chromophores, as described above, can produce enhanced emissions.

Figure 25A:
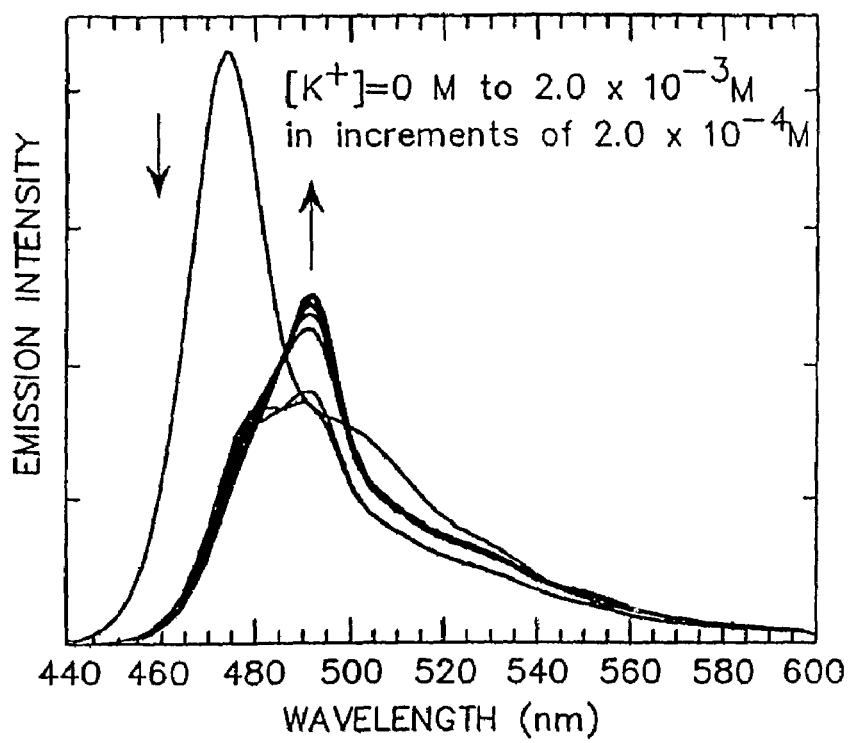
FIG. 25 shows an example of an exciplex structure formed in the presence of a cation and emission intensity data upon binding a cation.
Figure 25B:
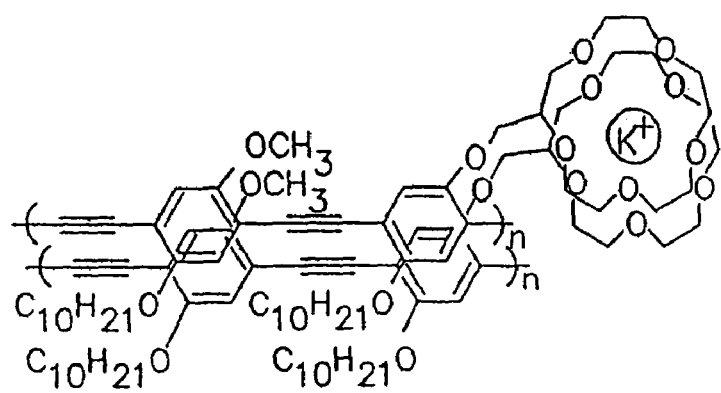
Figure 26:
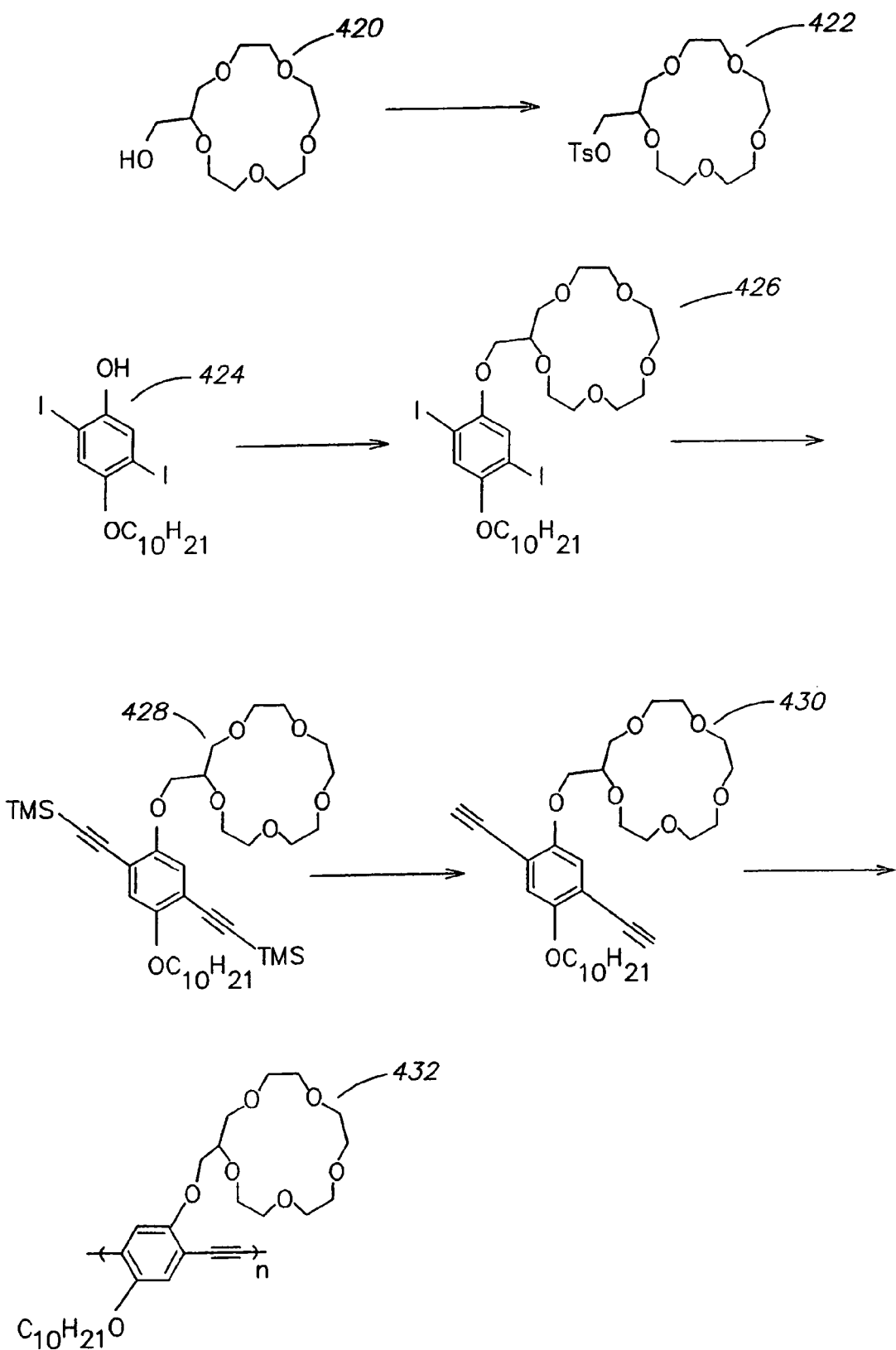
FIG. 26 shows a schematic synthesis of a polymer containing a crown ether.
Figure 27A:
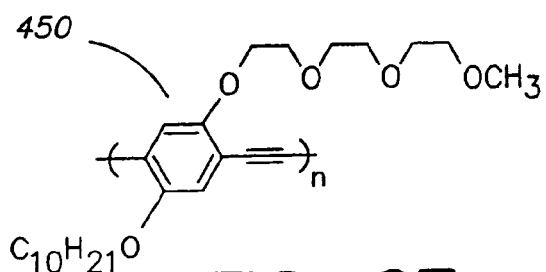
FIG. 27 shows examples of polymer structures having groups capable of binding cations.
Figure 27B:
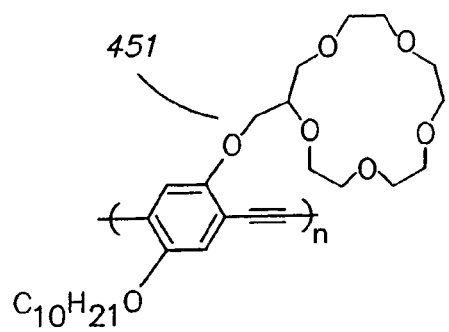
Figure 27C:
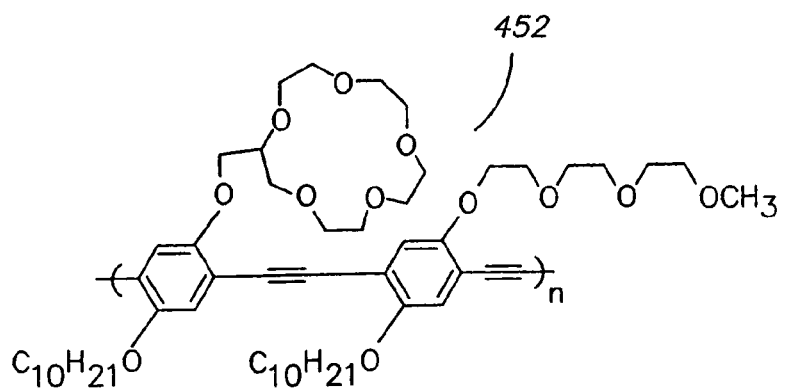
Figure 27D:
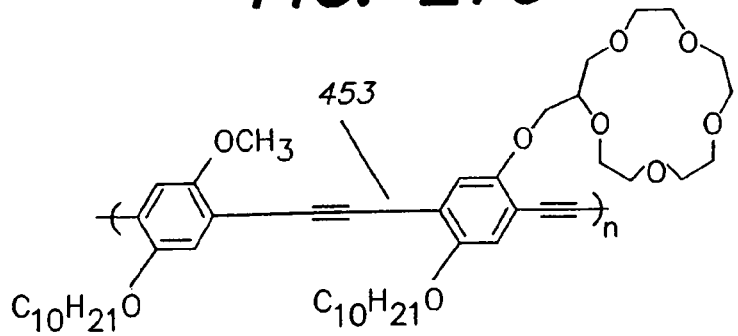
Figure 28A:
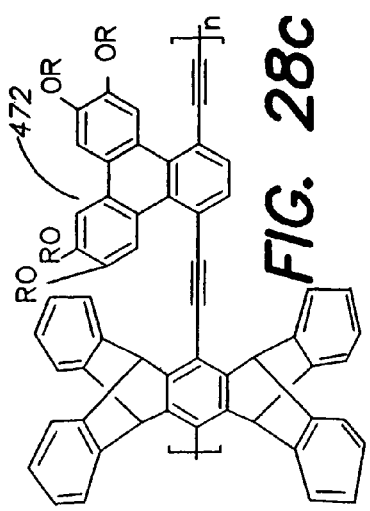
FIG. 28 shows examples of triphenylene-based polymer structures.
Figure 28B:
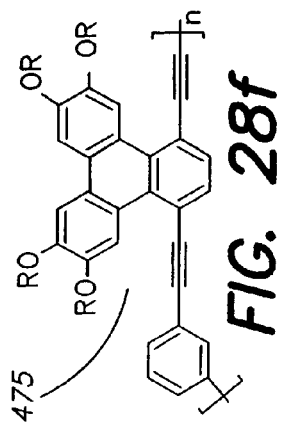
Figure 28C:
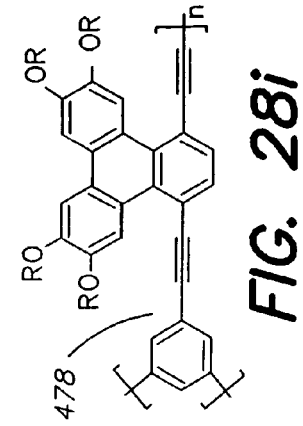
Figure 28D:
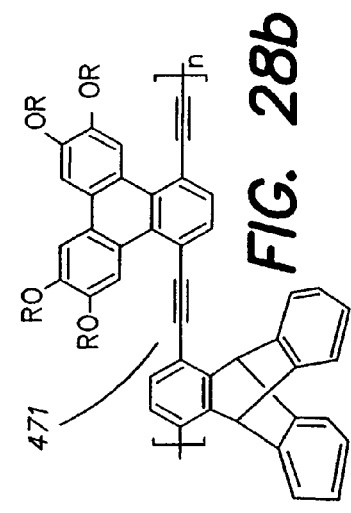
Figure 28E:
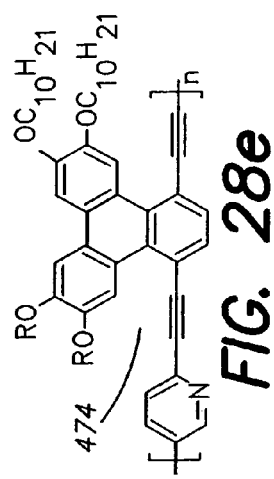
Figure 28F:
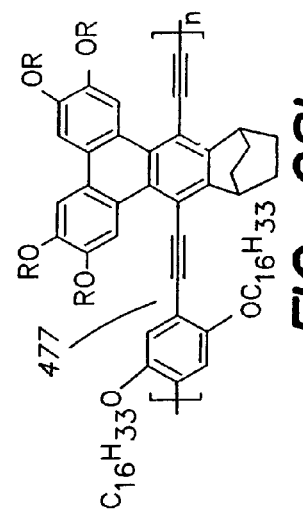
Figure 28G:
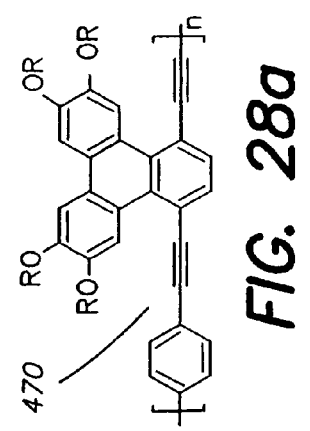
Figure 28H:
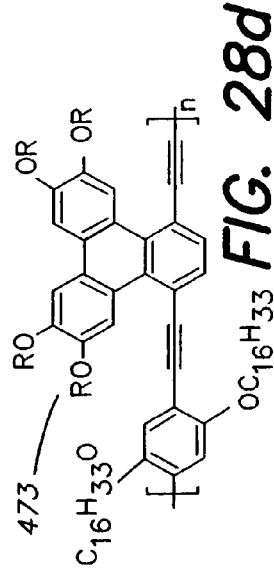
Figure 28I:
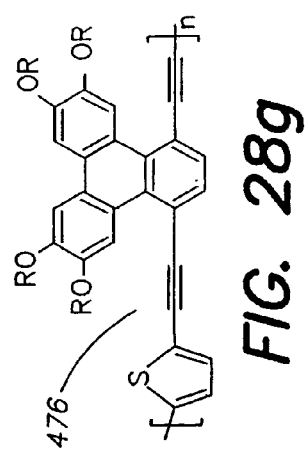

Another embodiment of the present invention provides a formation of excimer and exciplex structures which will provide lower energy chromophores having an emission intensity that can be enhanced by energy migration. Exciplex structures can be used as a detector for cations. Referring to FIG. 25, a polymer can include a group that is capable of binding a cation, such as a crown ether. Cation bonding is enhanced when two crown ethers are used for binding. This arrangement results in increased interaction between the polymer backbones and possibly π-stacking interactions can occur. FIG. 25 shows a fluorescence spectra of a crown ether containing polymer before and after addition of potassium salts. A new band (indicated by the upward arrow) is the result of an excimer induced by potassium ions. Crown ethers of various sizes, as is well known in the art, can be used to selectively bind cations of different sizes. FIG. 26 shows a schematic for the synthesis of a polymer containing a crown ether, and FIG. 27 shows polymers 450-453 that incorporate groups capable of binding cations. Other mechanisms for the formation of exciplexes include the binding of aromatic analytes.

The function and advantage of these and other embodiments of the present invention will be more fully understood from the examples below. The following examples are intended to illustrate the benefits of the present invention, but do not exemplify the full scope of the invention.

EXAMPLE 1

Synthesis of Poly(phenyleneethynylene)s Linked to Polystyrene Resin Beads

All manipulations were performed under a nitrogen atmosphere using standard Schlenk techniques or a Inovative Technologies dry box. Tetrahydrofuran was distilled from sodium benzophenone under nitrogen. Toluene and diisopropylamine were distilled from sodium under nitrogen and then degassed. NMR spectra were recorded on a Varian VXR-500 spectrometer at 500 ($^1$H), 125 ($^{13}$C) MHz using CDCl$_3$ as solvent. The chemical shifts are reported in ppm relative to TMS. Infrared spectra were collected as Nujol mulls on a Mattson Galaxy 3000 spectrometer, using KBr cells. Elemental analyses were performed by Desert Analytics. The molecular weights of polymers were determined using a Hewlett Packard series 1100 HPLC instrument equipped with a Plgel 5 mm Mixed-C (300×7.5 mm) column and a diode array detector at 245 nm at a flow rate of 1.0 mL/min in THF. The molecular weights were calibrated relative to polystyrene standards purchased from Polysciences, Inc. Polymer thin films were spin cast onto 18×18 mm glass slides. UV-vis spectra were obtained using a Hewlett Packard 8452A diode array spectrophotometer. Fluorescence experiments were performed using a SPEX Fluorolog-t2 fluorometer (model FL112, 450 W xenon lamp) equipped with a model 1935B polarization kit. Polymer thin-film spectra were recorded by front face (22.5°) detection. Time decay of fluorescence was determined by a phase-modulation method, using frequencies between 10 and 310 MHz. The compounds were purchased from Aldrich.

The synthesis of a polymer in accordance with the invention is detailed here. Starting materials diisopropylamine (DIPA) and toluene were distilled from sodium. The compounds 4-iodobenzoic acid, N,N-dimethylaminopyridine (DMAP), diisopropylcarbodiimide (DIC), Pd(PPh$_3$)$_4$, and CuI were purchased from Aldrich. The compounds 2,5-diethynyl-4-decyloxyanisole (10) and 1,4-dihexadecyloxy-2,5-diiodobenzene (20) were prepared according to literature procedures. The pentiptycene monomer (S) was prepared as outlined in Example 2. Aminomethylated polystyrene resin (200-400 mesh, 1.00 mmol/g) and Wang resin (200-400 mesh, 0.96 mmol/g) were purchased from Nova Biochem.

Preparation of 4-Iodo-Benzoic Acid Ethyl Ester. (40) A mixture of 4-iodobenzoic acid (10.0 g, 40.3 mmol), ethanol (100 mL) and concentrated H$_2$SO$_4$ (10 mL) was heated at reflux for 16 h. After cooling, excess solvent was removed from the reaction mixture under reduced pressure. The remaining oil was poured over ice (100 g) and the mixture was neutralized with a saturated solution of NaHCO$_3$. This mixture was extracted with hexane (200 mL). The hexane solution was washed with water (2×50 mL), dried over MgSO$_4$, and concentrated under reduced pressure. The remaining oil was distilled (110° C., 0.02 mm Hg) to give 10.06 g of the product as a colorless oil in 90% yield. $^1$H NMR spectra and IR spectra are consistent with those reported in the literature.

Phenyliodide Functionalized Wang Resin. (E) Wang resin (0.200 g), 4-iodobenzoic acid (0.0952 g, 0.384 mmol), and DMAP (0.0235 g, 0.192 mmol) were placed in a 100 mL reaction vessel. The vessel was evacuated and refilled with Ar three times. Then, DMF (15 mL) was added followed by DIC (75 mL, 0.48 mmol) and the resulting mixture was shaken for 48 h. The solution was removed by filtration and the resin was washed with DMF (3×20 mL) and CH$_2$Cl$_2$ (3×20 mL). The resin was then dried under vacuum at 60° C. for 3 h.

Polymerization of Poly(phenyleneethynylene) on Phenyliodide Functionalized Resin. (F) A schematic of the polymerization is shown in FIG. 8(a). A 100 mL reaction vessel was charged with the phenyliodide functionalized Wang resin (0.050 g), 10 (0.055 g, 0.176 mmol), and 20 (0.159 g, 0.176 mmol). The flask was evacuated and refilled with Ar three times. In a dry box Pd(PPh$_3$)$_4$ (6.8 mg, 0.0059 mmol) and CuI (2.2 mg, 0.012 mmol) were added to the flask. DIPA (1.0 mL) followed by toluene (2.5 mL) were added to the reaction mixture. The solution rapidly became fluorescent yellow. The reaction mixture was heated at 60° C. for 16 h. The solution was then removed by filtration and the resin was washed with toluene (3×20 mL) and CHCl$_3$ (3×20 mL). The final washings were colorless. The highly fluorescent yellow resin beads were then dried under vacuum at 60° C. for 3 h. Emission (solid film, λ, nm): 485, 515.

The polymer that was rinsed away from the resin beads was precipitated into acetone (300 mL) and washed with methanol and hexane. UV-Vis (CHCl$_3$, λ, nm): 319, 454. Emission (CHCl$_3$, λ, nm): 477, 504.

Polymerization of Pentiptycene-derived Poly(phenyleneethynylene) on Phenyliodide Functionalized Resin. (G) A 100 mL reaction vessel was charged with the phenyliodide functionalized Wang resin (0.050 g), S (0.053 g, 0.111 mmol), and 20 (0.100 g, 0.123 mmol). The flask was evacuated and refilled with Ar three times. In a dry box Pd(PPh$_3$)$_4$ (4 mg, 0.004 mmol) and CuI (1 mg, 0.007 mmol) were added to the flask. DIPA (1.0 mL) followed by toluene (2.5 mL) were added to the reaction mixture. The reaction mixture was heated at 60° C. for 48 h. The solution was then removed by filtration and the resin was washed with toluene (3×20 mL) and CHCl$_3$ (3×20 mL). The final washings were colorless. The highly fluorescent yellow resin beads were then dried under vacuum at 60° C. for 3 h. Emission (solid film, λ, nm): 456, 479.

Ethyl Ester End Functionalized Poly(phenyleneethynylene). (H) A schematic of the polymerization is shown in FIG. 8(b). A 25 mL Schlenk flask was charged with 10 (0.180 g, 0.222 mmol), 20 (0.076 g, 0.24 mmol), and 40 (0.0123 g; 0.044 mmol). The flask was purged with Ar and then charged with Pd(PPh$_3$)$_4$ (13 mg, 0.011 mmol) and CuI (2.1 mg, 0.011 mmol). DIPA (1.0 mL) and toluene (2.5 mL) were added and the reaction mixture was heated at 60° C. for 14 h. The reaction mixture was added dropwise to vigorously stirred acetone (200 mL). The polymer was collected on a filter and washed with acetone, methanol, and hexane until the filtrate was no longer colored. The polymer was then dried under vacuum at 60° C. for 3 h to afford H (0.16 g) in 78% yield. UV-Vis (CHCl$_3$, λ, nm): 319, 452. Emission (CHCl$_3$, λ, nm): 476, 504.

Ethyl Ester End Functionalized Pentiptycene-derived poly(phenyleneethynylene). (I) A 25 mL Schlenk flask was charged with 30 (0.080 g, 0.167 mmol), 20 (0.123 g, 0.152 mmol), and 40 (0.0084 g; 0.030 mmol). The flask was purged with Ar and then charged with Pd(PPh$_3$)$_4$ (9 mg, 0.008 mmol) and CuI (1.4 mg, 0.008 mmol). DIPA (1.0 mL) and toluene (2.5 mL) were added and the reaction mixture was heated at 70° C. for 48 h. The reaction mixture was added dropwise to vigorously stirred acetone (300 mL). The polymer was collected on a filter and washed with acetone, methanol, and hexane until the filtrate was no longer colored. The polymer was then dried under vacuum at 60° C. for 3 h to afford I (0.14 g) in 83% yield. UV-Vis (CHCl$_3$, λ, nm): 336, 426. Emission (CHCl$_3$, λ, nm): 454, 482.

End Functionalized poly(phenyleneethynylene) (H) grafted onto aminomethylated polystyrene resin. (J). A schematic of this synthesis is shown in FIG. 8(b) A 25 mL flask was charged with aminomethylated polystyrene resin (0.050 g; 0.050 mmol), end functionalized poly(phenyleneethynylene) (H) (0.030 g), sodium methoxide (3.0 mg; 0.055 mmol), and toluene (7.0 mL). This mixture was heated at reflux for 24 h. The solution was then removed by filtration and the resin was washed with toluene (3×20 mL) and CHCl$_3$ (3×20 mL). The final washings were colorless. The highly fluorescent yellow resin beads were then dried under vacuum at 60° C. for 3 h. Emission (solid film, λ, nm): 462, 500.

End Functionalized Pentiptycene-derived poly(phenyleneethynylene) (I) grafted onto aminomethylated polystyrene resin. (K). A 25 mL flask was charged with aminomethylated polystyrene resin (0.050 g; 0.050 mmol), end functionalized poly(phenyleneethynylene) (I) (0.030 g), sodium methoxide (3.0 mg; 0.055 mmol), and toluene (7.0 mL). This mixture was heated to 110° C. for 24 h. The solution was then removed by filtration and the resin was washed with toluene (3×20 mL) and CHCl$_3$ (3×20 mL). The final washings were colorless. The highly fluorescent yellow resin beads were then dried under vacuum at 60° C. for 3 h.

EXAMPLE 2

Synthesis of Monomers and Polymer A, B, and C

Syntheses of polymer A and B are outlined in FIG. 9(a) and the synthesis of polymer C is shown in FIG. 9(b).

General. All chemicals were of reagent grade. Benzoquinone was recrystallized in hexane before use. Anhydrous toluene and THF were purchased from Aldrich Chemical Co. Inc. NMR ($^1$H and $^{13}$C) spectra were recorded on Bruker AC-250, Varian Unity-300, or Varian VXR-500 Spectrometers, and chemical shifts are reported in ppm relative to TMS in proton spectra and to CHCl$_3$ in carbon spectra. UV-vis spectra were obtained from a Hewlett-Packard 8452A diode array spectrophotometer. Fluorescence studies were conducted with a SPEX Fluorolog-3 fluorometer.

Compounds L and M. To a mixture of anthracene (17.8 g, 0.1 mol) and benzoquinone (5.4 g, 0.05 mol) in a 200 mL round-bottom flask fitted with a condenser was added 75 mL of mesitylene. The mixture was refluxed for 24 h and then the solid was filtered after cooling to room temperature. The hydroquinone solid was digested in 100 mL of hot xylene twice and filtered (16.5 g). The crude hydroquinones (8 g) were dissolved in hot glacial acetic acid (ca 300 mL) and then a solution of 1.5 g of potassium bromate (9 mmol) in 100 mL of hot water was added. A deep orange color and precipitate developed immediately. The solution was boiled for a few minutes and then an additional 100 mL of hot water was added and the heat was removed. The orange quinone solid was collected after the solution was cooled. The quinones were washed with acetic acid and then with water. The crude quinones were dissolved in chloroform (ca. 120 mL) and washed with sodium bicarbonate and brine. The organic, layer was separated and dried (MgSO$_4$). The dark-colored impurities were removed by filtering the chloroform solution through a thin layer of silica gel. The resulting orange solution was adsorbed onto ca. 50 g of silica gel. The resulting yellow silica gel solid mixture was chromatographed using hexane/ethyl acetate (5:1) as the eluent to obtain 80-95% pure of compound L, which can be further purified by column chromatography using pure chloroform as the eluent. Compound M stays with silica gel and was obtained with 97-100% pure by re-dissolving the silica gel solid mixture in chloroform and then the removal of silica gel and chloroform solvent. The overall yields for L and M were 13% and 39%, respectively. Compound L: (mp=294.0° C., lit=292-296° C.).

Compounds N, O, and P. A mixture of pentacene (0.96 g, 3.45 mmol) and quinone (1.27 g, 4.49 mmol) in 3 mL of toluene was refluxed for 3 days and then cooled. The resulting yellow solid (1.87 g) was filtered and washed with hexane. The solid was placed in a round-bottom flask and ca. 80 mL of glacial acetic acid was added and then the solution was heated to reflux and then 5-10 drops of HBr (48%) was added. The color of solution faded in a short period of time. The solution was cooled after 30 min and then any undissolved solid was filtered off. The filtrate was then reheated again and potassium bromate (0.3 g in 20 mL hot water) was added. The solution was boiled for a few minutes and then 10 mL more of hot water was added and the heat was removed. The orange quinone solid was collected and washed with acetic acid and water. Column chromatography using pure chloroform as eluent allowed the separation of P from the mixture of N and O, which can be separated by another column chromatography using a mixed solvent of chloroform and hexane (2:1).

Compounds Q and R. A general procedure is illustrated by the synthesis of Q. Under an atmosphere of argon, one equivalent of n-butyllithium (2.5 mmol) in hexane was added dropwise to a solution of (trimethylsilyl)acetylene (0.35 mL, 2.5 mmol) in THF at 0° C. The mixture was then kept at 0° C. for another 40 min before it was transferred to a solution of quinone M (0.46 g, 1 mmol) in THF at 0° C. The mixture was warmed up to room temperature and stirred overnight. The reaction was quenched with 1 mL of 10% HCl and then subjected to a CHCl$_3$/H$_2$O workup. The solvent was removed and hexane was then added to the residue. The resulting white solid (0.59 g, 90%, 0.90 mmol), which is a mixture of the trans and cis isomers, was collected by filtration. This crude solid was dissolved in 10 mL acetone and then a solution of tin(II) chloride dihydrate (0.51 g, 2.25 mmol) in 50% of acetic acid (10 mL) was added dropwise. This mixture was stirred at room temperature for another 24 h and the resulting solid product was filtered. The solid was then dissolved in $CHCl_3$ and washed with water, sodium bicarbonate and then dried ($MgSO_4$). The $CHCl_3$ was removed in vacuo and the residue was washed with hexane to remove the yellow impurities. The resulting white solid was collected (yield 85%).

Compounds S and T. The deprotection of trimethylsilyl group was carried out by dissolving compounds Q or R in a mixture of KOH (two tablets in 1 mL H2O), THF, and MeOH and stirring at room temperature for 5 h. The resulting solid product was filtered and washed with water and then dried in vacuo.

Polymers A, B, and C. A general procedure is illustrated by the synthesis of polymer A. Under an atmosphere of argon, diisopropylamine/toluene (2:3, 2.5 mL) solvent was added to a 25 mL Schlenk flask containing compound S (40 mg, 0.084 mmol), 1,4-bis(tetradecanyloxyl)-2,5-diiodobenzene (63 mg, 0.084 mmol), CuI (10 mg, 0.053 mmol), and $Pd(Ph_3)_4$ (10 mg, 0.0086 mmol). This mixture was heated at 65° C. for three days and then subjected to a $CHCl_3/H_2O$ workup. The combined organic phase was washed with $NH_4Cl$, water and then dried ($MgSO_4$). The solvent was removed in vacuo, and the residue was reprecipitate in methanol three times. The polymer was a yellow solid (76 mg, 75%).

EXAMPLE 3

Synthesis of the Monomer 1,4-Dinaphthyl-2,5-diacetylidebenzene (DD

An overall scheme is depicted in FIG. 10(*b*).

1,4-Dibromo-2,5-dinaphthylbenzene (AA). Adapted from literature procedure reported by M. Goldfinger et al. A 100 ml Schlenk flask was charged with 1,4-dibromo-2,5-diiodobenzene (0.93 g, 1.91 mmol), naphthalene boronic acid (0.72 g, 4.19 mmol), triphenylphosphine (0.075 g, 0.29 mmol), palladium tetrakistriphenylphosphine (0.022 g, 0.019 mmol), and KOH (2.2 g, 39 mmol). To this mixture, 5 mL deionized $H_2O$ and 20 mL nitrobenzene were introduced via syringes. The resulting mixture was initially purged with a rapid stream of Argon, then was evacuated and refilled with argon five times before it was heated to 90° C. in an oil bath. After maintaining at this temperature for 24 hrs, the solvent was removed by distillation under high vacuum. The residue was transferred into a filtration funnel and successively washed with 100 mL $H_2O$, 20 mL acetone and 20 mL cold chloroform. Drying of the rinsed solids under vacuum afforded an off-white powder (0.65 g, 70%).

1,4-Diiodo-2,5-dinaphthylbenzene (BB): At –78° C., AA (0.3 g, 0.61 mmol) was poured into a Schlenk flask containing t-BuLi (3 mL, 1.7M in hexanes) and 15 mL THF. The resulting mixture was allowed to warm up to –40° C. and stirred at this temperature for 1 hr. At this temperature, $I_2$ (1.5 g, 5.9 mmol) crystals were added in one portion under strong argon flow. The deep red solution was stirred at room temperature for four hours before it was quenched by adding dilute sodium hydrosulfite solution. The solvent was removed under vacuum and the residual solid was washed with water, acetone, and chloroform sequentially to give a pale white powder (0.16 g, 50%).

1,4-Dinaphthyl-2,5-di((trimethylsilyl)ethynyl)benzene (CC): Under an argon atmosphere, BB (0.14 g, 0.24 mmol), $Pd(PPh_3)_2Cl_2$ (8.5 mg, 0.012 mmol), and CuI (0.005 g, 0.024 mmol) were mixed in 1 mL $HN(iPr)_2$ and 5 mL toluene. Trimethylsilylacetylene (0.071 g, 0.72 mmol) was then introduced into the mixture via a syringe. The resulting brown solution was heated to 70° C. for two hours before it was cooled down and filtered to remove insoluble iodium salts. The filtrate was concentrated, loaded onto a silica gel column and eluted with the mixture of hexanes and chloroform (10:1) to give a light yellow solid (0.1 g, 80%).

1,4-Dinaphthyl-2,5-diacetylidebenzene (DD): A solution of potassium hydroxide (150 mg, 2.67 mmol) in 2 mL $H_2O$ and 8 mL MeOH was added dropwise to a solution of 3 in 16 mL THF under magnetic stirring. After the clear solution was stirred at room temperature overnight the solvent was removed under vacuum. The residue was dissolved in $CHCl_3$, washed with $H_2O$ and concentrated. Trituration of the solid with acetone, filtration of the precipitate, and drying the product under high vacuum gave a essentially pure off-white solid (0.041 g, 54%).

EXAMPLE 4

Polymer Synthesis from Monomer DD

A schematic of this synthesis is shown in FIG. 10(*a*). A Schlenk flask was charged with DD (0.019 g, 0.049 mmol), 1,4-ditetradecyloxy-2,5-diiodobenzene (0.035 g, 0.049 mmol), palladium tetrakistriphenylphosphine (0.0056 g, 0.0048 mmol), CuI (0.001 g, 0.0053 mmol), 1.5 mL toluene, and 1 mL $HN(iPr)_2$. The heterogeneous mixture was initially stirred at room temperature for 20 min then heated to 70° C. for 48 hrs. The resulting brownish fluorescent solution was precipitated in MeOH and the polymer precipitate was isolated by suction filtration. Reprecipitation of the polymer in acetone from chloroform give a brown polymer (0.03 g, 71%).

EXAMPLE 5

Synthesis of Triphenylene-Based Monomers

Figure 30:
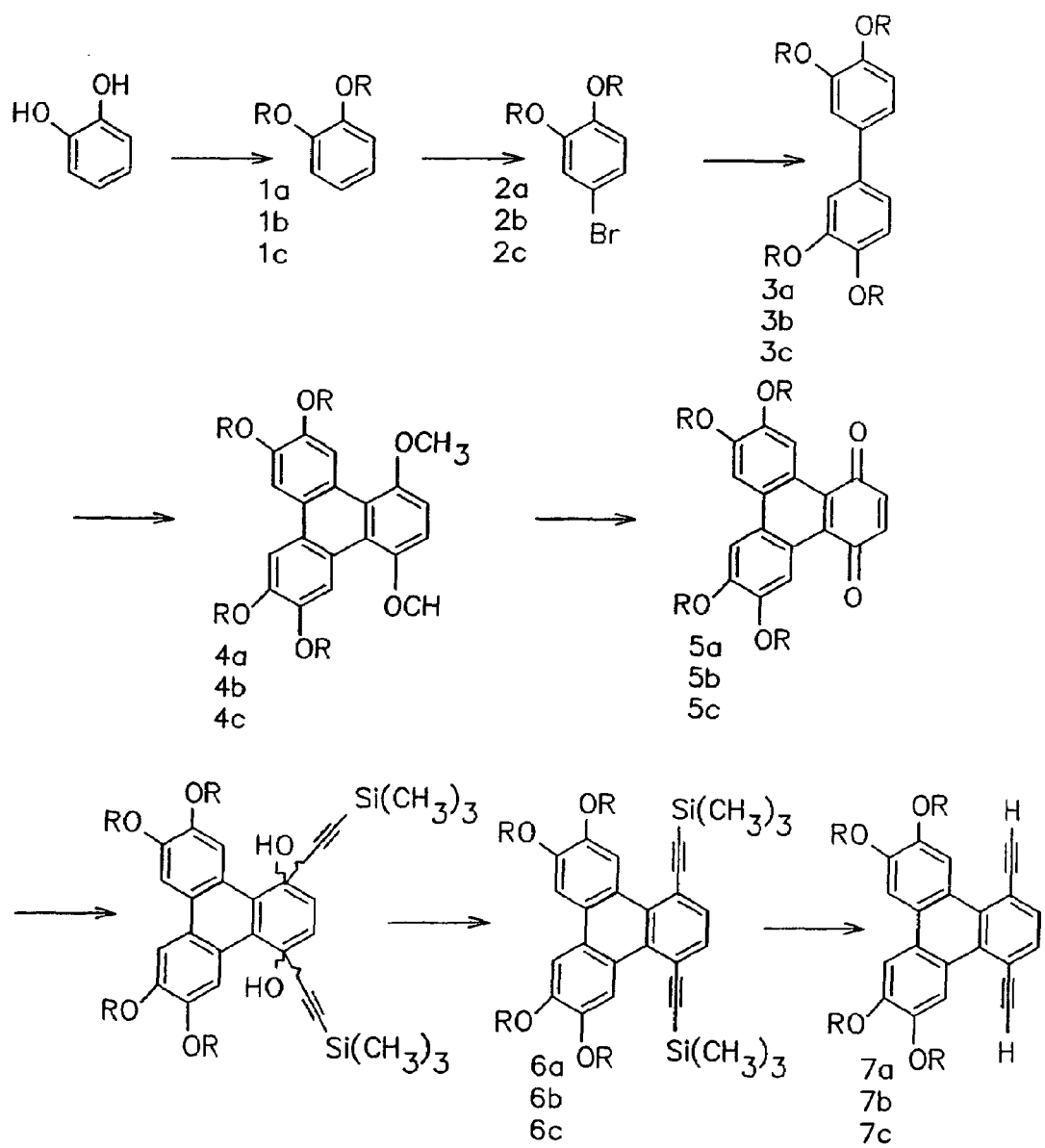
FIG. 30 shows a schematic synthesis of a triphenylene-based monomer.
Figure 31:
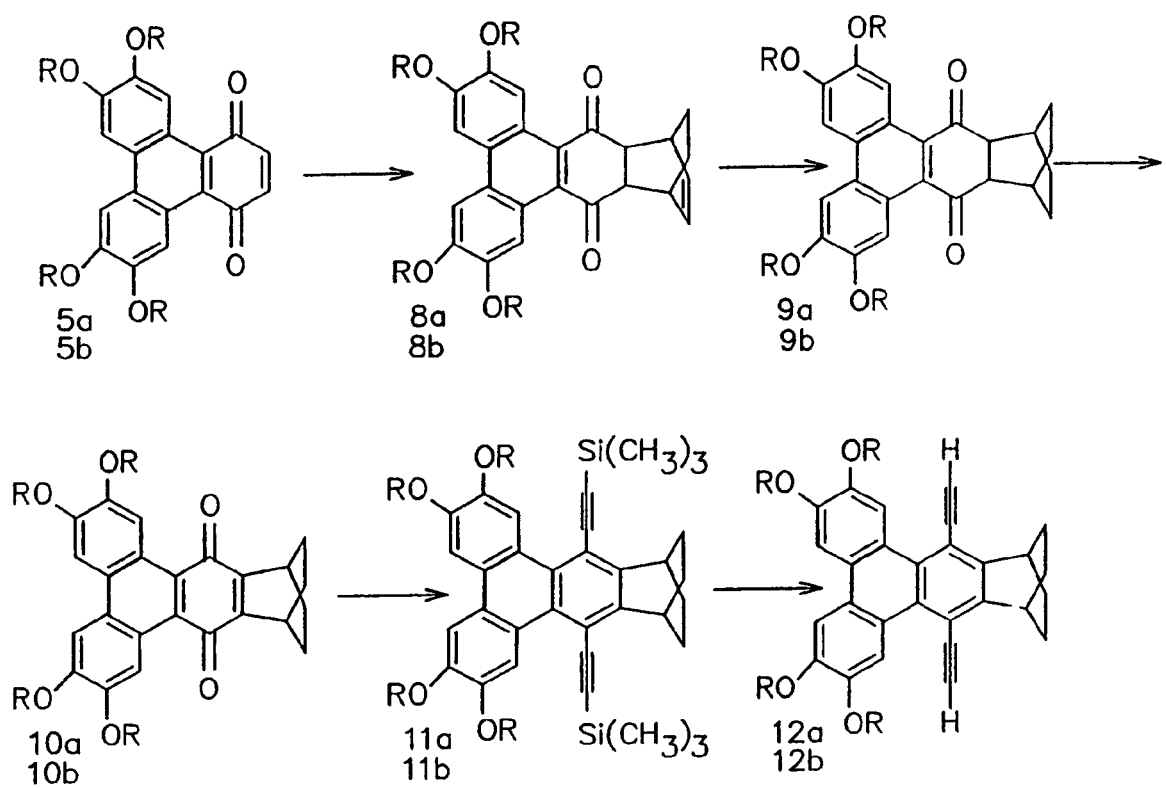
FIG. 31 shows a schematic synthesis of a triphenylene-based monomer.

FIGS. 30 and 31 schematically show the synthesis of triphenylene-based monomers having acetylene polymerization units.

The compound 1,2-didecyloxybenzene (1a) was prepared according to literature procedures.

1,2-di(2-ethylhexyloxy)benzene (1b). In a 2 L flask were combined 2-ethylhexylbromide (127.9 mL, 0.719 mol), KI (21.71 g, 0.131 mol), $K_2CO_3$ (180.8 g, 1.31 mol), and chatechol (36.0 g, 0.327 mol). The flask was purged with $N_2$ for 10 min. and 1 L butanone was added. The mixture was heated at reflux for 22 d. The reaction mixture was then filtered and the solids washed with ether. The filtrate was washed several times with water, dried ($MgSO_4$) and concentrated under reduced pressure. The crude product was distilled (80° C./0.02 mmHg) to give 1,2-di(2-ethylhexyloxy)benzene (1b) as a colorless oil in 79% yield.

1,2-diethoxybenzene (1c). The synthesis of this compound was initiated similarly to the synthesis of 1b. The reaction mixture was stirred at room temperature for 2 d. The reaction mixture was then filtered and the solids were rinsed with ether. The filtrate was washed with dilute aqueous KOH and several times with water. The organic fraction was dried ($MgSO_4$) and concentrated under reduced pressure. The crude product was distilled (80° C./5 mmHg) to give 1,2-diethoxybenzene (1c) as a colorless crystalline solid in 11% yield (mp=40.0-40.5).

4-bromo-1,2-didecyloxybenzene (2a). A CH₃CN solution (100 mL) of NBS (13.67 g, 76.80 mmol) was added dropwise to a CH₃CN solution (300 mL) of 1a (30.00 g, 76.80 mmol). The mixture was stirred at reflux for 12 h in the absence of light. The reaction mixture was cooled and the solvent was removed under reduced pressure. The residue was extracted with ether, washed with a saturated NaHCO₃ solution and water. After drying with MgSO₄ the solvent was removed under reduced pressure. Crystallization from THF/MeOH afforded colorless crystals of 4-bromo-1,2-didecyloxybenzene (2a) in 93% yield (mp 39.5-40° C.).

4-bromo-1,2-di(2-ethylhexyloxy)benzene (2b). Solid NBS (26.21 g, 0.147 mol) was added to an ice cold CH₂Cl₂ solution (250 mL) of 1b under N₂ in the absence of light. Just enough DMF was added (30 mL) to dissolve the NBS. The reaction mixture was allowed to warm to room temperature and then stirred for 12 h. The mixture was then poured into water. The organic layer was washed with a saturated LiCl solution and water. After drying with MgSO4 the solvent was removed under reduced pressure. The remaining oil was distilled (160° C./0.01 mmHg) to yield 4-bromo-1,2-di(2-ethylhexyloxy)benzene (2b) in 96% yield as a colorless oil.

4-bromo-1,2-diethoxybenzene (2c). Compound 4-bromo-1,2-diethoxybenzene (2c) was prepared according to the procedure for the synthesis of 2b. The crude product was distilled (75° C./0.03 mmHg) to give 2c as a colorless oil in 86% yield.

3,3',4,4'-tetrakisdecyloxybiphenyl (3a). A hexane solution of ″BuLi (1.57 M, 1.02 mL) was added dropwise to a THF solution (50 mL) of 2a which had been precooled to −30° C. Once the addition was complete the reaction mixture was allowed to warm to room temperature. After stirring for an additional 12 h the reaction mixture was poured into water and extracted with ether. The ether layer was washed with water and dried with MgSO₄. The solvent was removed under reduced pressure. The residue was crystallized from a THF/MeOH mixture at −15° C. to give colorless crystals of 3,3',4,4'-tetrakisdecyloxybiphenyl (3a) in 38% yield (mp 85-86° C.).

3,3',4,4'-tetrakis(2-ethylhexyl)biphenyl (3b). A THF solution (500 mL) of 2b (46.32 g, 0.112 mol) was cooled to −60° C., and a hexane solution of ″BuLi (143 mL, 1.57 M, 0.224 mol) was added. The mixture was allowed to warm to 0° C. over 1 h and then stir at that temperature for 1 h. The solution was then cooled to −60° C. and CuCl₂ (30.12 g, 0.224 mol) was added. The mixture was allowed to warm to room temperature over 1 h and was then heated at reflux for 12 h. The reaction mixture was cooled to room temperature and poured into dilute HCl. This mixture was extracted twice with ether. The combined organic fractions were washed with water, dried with MgSO4, and filtered through a short plug of silica Solvent was removed under reduced pressure and the remaining oil was purified by column chromatography using a 2% ether/98% hexane solvent mixture to afford 3b (RF=0.26) as a slightly yellow oil in 51% yield.

3,3',4,4'-tetraethoxybiphenyl (3c). Compound 3c was prepared by the same method described for 3b using 2c as starting material. The crude product was crystallized from THF/MeOH to afford 3c as colorless plates in 66% yield (mp=140-141° C.).

1,4-dimethoxy-6,7,10,11-tetrakis(decyloxy)triphenylene (4a). Solid 3a (5.50 g, 7.06 mmol) was added to an ice cold suspension of anhydrous FeCl₃ (9.16 g, 56.5 mmol) in dry CH₂Cl₂ (250 mL). Within 2 min 1,4-dimethoxybenzene (3.90 g, 28.2 mmol) was added to the green reaction mixture. The reaction mixture was allowed to warm slowly to room temperature and then stir for an additional 12 h. The reaction mixture was quenched with anhydrous MeOH (30 mL). The volume of the mixture was reduced to 50 mL under reduced pressure and MeOH (200 mL) was added to the resulting oil. The slightly violet product was called on a frit and washed with MeOH. The product was further purified by column chromatography using a 50% CH₂Cl₂/50% hexane solvent mixture to afford 4a (RF=0.24) as a colorless solid in 84% yield (mp 69-70° C.).

1,4-dimethoxy-6,7,10,11-tetrakis(2-ethylhexyloxy)triphenylene (4b). The reaction to produce 4b was initiated as described for 4a. After quenching the reaction with anhydrous MeOH the volume of the mixture was reduced under reduced pressure. The remaining mixture was poured into water and extracter twice with ether. The ether fractions were washed with water, dried with MgSO₄, and concentrated under reduced pressure. The remaining solid was purified by column chromatography on silica gel (1:3 CH₂Cl₂/hexane) to afford 4b as a colorless waxy solid in 28% yield (mp=54-56° C.).

1,4-dimethoxy-6,7,10,11-tetraethoxytriphenylene (4c). Compound 4c was prepared according to the procedure for the synthesis of 4b. The product was crystallized from THF/MeOH at −15° C. to afford colorless needles in 30% yield (mp 157-157.5° C.).

6,7,10,11-tetrakis(decyloxy)triphenylene-1,4-dione (5a). An aqueous solution (1 mL) of (NH₄)₂Ce(NO₃)₆ (0.035 g, 0.064 mmol) was added dropwise to a THF solution (5 mL) of 4a (0.029 g, 0.032 mmol). The reaction mixture immediately turned deep red. After 6 h the reaction mixture was poured into ether and washed with a saturated solution of NaHCO₃ and water. The organic layer was dried with MgSO₄ and the solvent removed under reduced pressure. The crude product was purified by column chromatography on silica gel (1:1 CH₂Cl₂/hexane) to afford 5a as a deep red solid in 80% yield (mp 86-87° C.).

6,7,10,11-tetrakis(2-ethylhexyloxy)triphenylene-1,4-dione (5b). Compound 5b was prepared by the method described for 5a in 55% yield (mp=105-107° C.).

6,7,10,11-tetraethoxytriphenylene-1,4-dione (5c). Compound 5c was prepared by the method described for 5a in 58% yield (mp 188-190° C.).

6,7,10,11-tetrakis(decyloxy)-1,4-di(2-trimethylsilylacetylene)triphenylene (6a). A hexane solution of ″BuLi (2.77 mL, 1.57 M, 4.35 mmol) was added to a THF solution (15 mL) of trimethylsilylacetylene (0.615 mL, 4.35 mmol) which had been precooled to −78° C. The mixture was allowed to warm to −10° C. and stirred at that temperature for 30 min. The solution was then cooled to −78° C. and a THF solution (10 mL) of 5a was added dropwise. During the addition the red color of the quinone dissipated. After the addition was complete the reaction mixture was allowed to warm to room temperature and then stirred for an additional 12 h. The reaction mixture was then poured into ether and enough dilute HCl was added to make the solution slightly acidic. The organic layer was then quickly washed with several portions of water and dried with MgSO₄. The solvent was removed under reduced pressure and the remaining light brown oil was dissolved in acetone (50 mL). To this solution was added dropwise a solution of SnCl₂·2 H₂O (0.851 g, 3.77 mmol) in 50% HOAc (10 mL). After 12 h the reaction mixture was poured into ether and washed with water, a saturated solution of NaHCO₃ and again water. The organic layer was dried with MgSO₄ and the solvent was removed under reduced pressure. The product was purified by column chromatography on silica gel (1:3 CH₂Cl₂/hexane) to afford 6a as a viscous yellow oil in 38% yield.

6,7,10,11-tetrakis(2-ethylhexyloxy)triphenylene-1,4-di(2-trimethylsilyl) acetylene (6b). Compound 6b was prepared by the method described for 6a using 5b as starting material. Compound 6b was obtained as a yellow oil in 97% yield.

Compound 6c was prepared by the method described for 6a using 5c as starting material. (6c: R=ethyl)

6,7,10,11-tetrakis(decyloxy)-1,4-ethynyltriphenylene (7a). An aqueous solution (1 mL) of KOH (0.30 g) was added to a 1:1 THF/MeOH solution (20 mL) of 6a (0.477 g, 0.475 mmol). The reaction mixture was allowed to stir for 12 h. It was then poured into ether and washed with water. The organic layer was dried with $MgSO_4$ and the solvent removed under reduced pressure. The product was purified by flash chromatography on silica gel using a 1:3 $CH_2Cl_2$/hexane solvent mixture. Compound 7a was obtained as a colorless solid in 81% yield (mp 68-69° C.).

6,7,10,11-tetrakis(2-ethylhexyloxy)-1,4-ethynyltriphenylene (7b). Compound 7b was prepared by the method described for 7a using 6b as starting material. Compound 7b was obtained as a yellow oil in 89% yield.

Compound 7c was prepared by the method described for 7a using 6c as starting material. (7c: R=ethyl)

(10a). Compound 5a (0.516 g, 0.584 mmol) was dissolved in 1,3-cyclohexadiene (10 mL). The mixture was heated to 80° C. for 12 h. The excess 1,3-cyclohexadiene was then removed under reduced pressure. The remaining viscous oil was transferred to a hydrogenation vessel (50 mL capacity) along with $CH_2Cl_2$ (10 mL) and 10% Pd on carbon (10 mg). This mixture was degassed and then shaken under $H_2$ (40 psi) for 24 h. The reaction mixture was then filtered through a short plug of silica and evaporated to dryness. The remaining solid was added to glacial acetic acid (40 mL) and heated to 100° C. Two drops of concentrated HBr were added causing the solution to turn dark red. After 5 min an aqueous solution (10 mL) of $KBrO_3$ (0.016 g, 0.096 mmol) was added and the mixture was heated for an additional 10 min. The solution was allowed to cool and then extracted with two portions of $CH_2Cl_2$. The combined organic fractions were washed with water, dried with $MgSO_4$, and evaporated to dryness. The crude product was purified by column chromatography on silica gel using a 1:9 ether/hexane solvent mixture affording 10a (R=n-Decyl) in 54% yield. By this method, the reaction proceeds through intermediates 8a and 9a.

(10b). Compound 10b (R=2-ethylhexyl) was prepared by the method described for 10a using 5b as starting material. The reaction proceeds through intermediates 8b and 9b. Compound 10b was obtained as a dark red viscous oil in 84% yield.

(12a). Compound 11a (R=n-Decyl) was prepared by the method described for 6a using 10a as starting material. Compound 11a was purified by column chromatography on silica gel using a 1:49 ether/hexane solvent mixture. The product was then converted to the diacetylene (12a: R=n-Decyl) by the method described for 7a. The crude diacetylene was purified by column chromatography on silica gel using a 1:19 ether/hexane solvent mixture to afford 12a as a light orange solid in an overall 53% yield (mp 48.5-49.5° C.).

Compound 11b was prepared by the method described for 6a using 10b as starting material. (11b: R=2-ethylhexyl)

(12b). Compound 12b (R=2-ethylhexyl) was prepared by the method described for 12a using 10b as starting material. Compound 12b was obtained as a light yellow oil in an overall 56% yield from 10b.

1,4-diiodo-2,3,5,6-tetraalkoxybenzene:
To the solution of dibromotetraoctoxybenzene (3 g, 4.0 mmol) in 20 ml THF, n-Buli (10 ml, 16 mmol) was added via a syringe at −78° C. The solution was allowed to warm up slowly to 0° C. and stirred at this temperature for 40 min. Then I2 crstals were poured into the solution in two portions. After the purple solution was stirred at room temperature overnight, the excess I2 was removed by washing with 10% NaOH solution. The resulting colorless solution was dried with MgSO4 and concentrated under vaccum to give a cotton-like solid (3 g, 91%).

1,4-Bis-[(trimethylsilyl)ethynyl]-2,3,5,6-tetraalkoxybenzene:
Under an argon atomsphere, 1,4-diiodo-2,3,5,6-tetraalkoxybenzene (1 g, 1.19 mmol), $Pd(PPh_3)_2Cl_2$ (41 mg, 0.058 mmol), and CuI (22 mg, 0.12 mmol) were mixed in 10 mL $HN(^iPr)_2$ and 5 mL toluene. Trimethylsilylacetylene (0.42 ml, 2.97 mmol) was then introduced into the mixture via a syringe. The resulting brown solution was heated to 70° C. for two hours before it was cooled down and filtered to remove insoluble iodium salts. The filtrate was concentrated, loaded onto a silica gel column and eluted with the mixture of hexanes and chloroform (10:1) to give a light yellow oil (0.78 g, 83%).

2,3,5,6-Tetraalkoxy-1,4-diacetylidebenzene:
A solution of potassium hydroxide (150 mg, 2.67 mmol) in 2 mL $H_2O$ and 8 mL MeOH was added dropwise to a solution of the yellow oil above in 16 mL THF under magnetic stirring. After the solution was stirred at room temperature overnight, the solvent was removed under vaccum. The residue was dissolved in $CHCl_3$, washed with $H_2O$ and concentrated. The resulting green solid was chromatographed on a silica gel column with the mixture of hexanes and chlorform to afford a off-white solid (0.52 g, 85%).

FIG. 32 shows examples of triphenylene-based polymers that can be prepared by the monomers described above using standard palladium-catalyzed techniques.

Those skilled in the art would readily appreciate that all parameters listed herein are meant to be exemplary and that actual parameters will depend upon the specific application for which the methods and apparatus of the present invention are used. It is, therefore, to be understood that the foregoing embodiments are presented by way of example only and that, within the scope of the appended claims and equivalents thereto, the invention may be practiced otherwise than as specifically described.

What is claimed is:

1. A method for detecting the presence of an analyte, comprising:
   providing an article comprising a polymer having an energy migration pathway and a chromophore;
   exposing the article to a source of energy to form an excitation energy;
   allowing the excitation energy to travel through the migration pathway and to transfer to the chromophore, causing a first emission that is different than an emission resulting from a polymer free of an energy migration pathway;
   exposing the article to a medium containing an analyte and to the source of the excitation energy to cause a second emission of radiation from the article; and
   detecting a difference between the first emission and the second emission.

2. A method as in claim 1, wherein the pathway includes a HOMO-LUMO gap that continually decreases in a direction along the energy migration pathway to the chromophore.

3. A method as in claim 1, wherein the article comprises at least one layer of a polymer including a chromophore.

4. A method as in claim 3, wherein the article comprises multiple layers, each layer comprising a polymer including a chromophore and the energy migration pathway being continuous throughout the multiple layers.

5. A method for detecting the presence of an analyte, comprising:
- providing an article comprising a polymer having an energy migration pathway, the polymer having reduced π-stacking;
- exposing the article to a source of energy to form an excitation energy;
- allowing the excitation energy to travel through the migration pathway to cause a first emission that is greater than an emission resulting from a polymer free of an energy migration pathway;
- exposing the article to a medium containing an analyte and to the source of the excitation energy to cause a second emission of radiation from the article; and
- detecting a difference between the first emission and the second emission.

6. A method as in claim 5, wherein the polymer having reduced π-stacking has a backbone separated from adjacent backbone at a distance of at least about 4.5 Å.

7. A method as in claim 5, wherein the polymer having reduced π-stacking has a backbone separated from adjacent backbone at a distance of at least about 5.0 Å.

8. A method for detecting the presence of an analyte, comprising:
- providing an article comprising a polymer having an energy migration pathway, wherein the polymer exhibits a quantum yield at least about 0.05 times that of a quantum yield of the polymer in solution;
- exposing the article to a source of energy to form an excitation energy;
- allowing the excitation energy to travel through the migration pathway to cause a first emission from the polymer that is different than an emission resulting from a polymer free of an energy migration pathway;
- exposing the article to a medium containing an analyte and to the source of the excitation energy to cause a second emission of radiation from the article; and
- detecting a difference between the first emission and the second emission.

9. A method for detecting the presence of an analyte, comprising: providing an article comprising a polymer having an energy migration pathway, wherein the polymer exhibits a quantum yield at least about 0.05 times that of a quantum yield of the polymer in solution;
- exposing the article to a source of excitation energy to cause a first emission of radiation from the article;
- exposing the article to a medium containing an analyte and to the source of the excitation energy to cause a second emission of radiation from the article; and
- detecting a difference between the first emission and the second emission.

* * * * *